US011882838B2

(12) United States Patent
Franco

(10) Patent No.: US 11,882,838 B2
(45) Date of Patent: Jan. 30, 2024

(54) BACTERIAL INOCULANTS

(71) Applicant: The Flinders University of South Australia, Bedford Park (AU)

(72) Inventor: Christopher Milton Mathew Franco, Stonyfell (AU)

(73) Assignee: The Flinders University of South Australia, Bedford Park (AU)

( * ) Notice: Subject to any disclaimer, the term of this patent is extended or adjusted under 35 U.S.C. 154(b) by 832 days.

(21) Appl. No.: 16/608,421

(22) PCT Filed: Apr. 27, 2018

(86) PCT No.: PCT/AU2018/050387
§ 371 (c)(1),
(2) Date: Oct. 25, 2019

(87) PCT Pub. No.: WO2018/195603
PCT Pub. Date: Nov. 1, 2018

(65) Prior Publication Data
US 2020/0045979 A1 Feb. 13, 2020

Related U.S. Application Data

(60) Provisional application No. 62/568,763, filed on Oct. 5, 2017.

(30) Foreign Application Priority Data

Apr. 27, 2017 (AU) .................................. 2017901523

(51) Int. Cl.
*A01N 63/10* (2020.01)
*C12N 1/20* (2006.01)
*C12R 1/465* (2006.01)

(52) U.S. Cl.
CPC .............. *A01N 63/10* (2020.01); *C12N 1/20* (2013.01); *C12N 1/205* (2021.05); *C12R 2001/465* (2021.05)

(58) Field of Classification Search
None
See application file for complete search history.

(56) References Cited

U.S. PATENT DOCUMENTS

| | | |
|---|---|---|
| 2,200,532 A | 5/1940 | Bond |
| 4,642,131 A | 2/1987 | Hoitink |
| 4,940,834 A | 7/1990 | Hurley et al. |
| 5,041,290 A | 8/1991 | Gindrat et al. |
| 5,113,619 A | 5/1992 | Leps et al. |
| 5,229,291 A | 7/1993 | Nielsen et al. |
| 5,292,507 A | 3/1994 | Charley |
| 5,300,127 A | 4/1994 | Williams |
| 5,415,672 A | 5/1995 | Fahey et al. |
| 5,730,973 A | 3/1998 | Morales et al. |
| 5,919,447 A | 7/1999 | Marrone et al. |
| 5,989,543 A | 11/1999 | Davide et al. |
| 5,994,117 A | 11/1999 | Bacon et al. |
| 6,072,107 A | 6/2000 | Latch et al. |
| 6,077,505 A | 6/2000 | Parke et al. |
| 6,337,431 B1 | 1/2002 | Tricoli et al. |
| 6,495,133 B1 | 12/2002 | Xue |
| 6,602,500 B1* | 8/2003 | Kharbanda ............ C07K 14/32 424/93.46 |
| 6,681,186 B1 | 1/2004 | Denisov et al. |
| 6,689,880 B2 | 2/2004 | Chen et al. |
| 6,823,623 B2 | 11/2004 | Minato et al. |
| 7,037,879 B2 | 5/2006 | Imada et al. |
| 7,080,034 B1 | 7/2006 | Reams |
| 7,084,331 B2 | 8/2006 | Isawa et al. |
| 7,335,816 B2 | 2/2008 | Kraus et al. |
| 7,341,868 B2 | 3/2008 | Chopade et al. |
| 7,435,411 B2 | 10/2008 | Park et al. |
| 7,485,451 B2 | 2/2009 | VanderGheynst et al. |
| 7,555,990 B2 | 7/2009 | Beaujot |
| 7,632,985 B2 | 12/2009 | Malven et al. |
| 7,763,420 B2 | 7/2010 | Stritzker et al. |
| 7,906,313 B2 | 3/2011 | Henson et al. |
| 7,977,550 B2 | 7/2011 | West et al. |
| 8,019,694 B2 | 9/2011 | Fell et al. |
| 8,143,045 B2 | 3/2012 | Miasnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |
| 9,113,636 B2 | 8/2015 | von Maltzahn et al. |
| 9,277,751 B2 | 3/2016 | Sword |

(Continued)

FOREIGN PATENT DOCUMENTS

| | | |
|---|---|---|
| AU | 2015201322 | 4/2015 |
| CA | 1041788 A | 11/1978 |

(Continued)

OTHER PUBLICATIONS

Jin et al. Accession GU328691, deposited Mar. 30, 2011.*
Jin et al Microbiologia (2011)80(1):117-124.*
Janda et al (Journal of Clinical Microbiology (2007) 45(9):2761-2764).*
Petti. Clinical Infectious Diseases (2007)44:1108-114.*
Rasmussen, S., et al., "Grass-endophyte interactions: a note on the role of monosaccharide transport in the Neotyphodium lolii—Lolium perenne symbiosis," New Phytologist, 2012, pp. 7-12, vol. 196.

(Continued)

Primary Examiner — Medina A Ibrahim
(74) Attorney, Agent, or Firm — K&L Gates LLP

(57) ABSTRACT

The present disclosure relates to bacterial inoculants, and methods for their use, to control a fungal root disease in a plant and promote plant growth in water limited conditions. In particular strains of *Paenibacillus* and *Streptomyces* are disclosed.

16 Claims, 3 Drawing Sheets
Specification includes a Sequence Listing.

(56) References Cited

U.S. PATENT DOCUMENTS

| | | |
|---|---|---|
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 | 8/2018 | von Maltzahn et al. |
| 10,076,120 B2 | 9/2018 | von Maltzahn et al. |
| 10,104,862 B2 | 10/2018 | Vujanovic et al. |
| 10,136,646 B2 | 11/2018 | Von Maltzahn et al. |
| 10,212,912 B2 | 2/2019 | Vujanovic et al. |
| 10,306,890 B2 | 6/2019 | Mitter et al. |
| 10,362,787 B2 | 7/2019 | Mitter et al. |
| 10,499,652 B2 | 12/2019 | von Maltzahn et al. |
| 10,499,653 B2 | 12/2019 | von Maltzahn et al. |
| 10,499,654 B2 | 12/2019 | von Maltzahn et al. |
| 10,640,783 B2 | 5/2020 | Riley |
| 10,645,938 B2 | 5/2020 | Riley |
| 10,667,523 B2 | 6/2020 | Ambrose et al. |
| 10,750,711 B2 | 8/2020 | Djonovic et al. |
| 10,932,469 B2 | 3/2021 | Mitter et al. |
| 11,119,086 B2 | 9/2021 | Mitter et al. |
| 11,151,379 B2 | 10/2021 | Freitag et al. |
| 2001/0032162 A1 | 10/2001 | Alsberg et al. |
| 2002/0059091 A1 | 5/2002 | Hay et al. |
| 2002/0120555 A1 | 8/2002 | Lerner |
| 2002/0142917 A1 | 10/2002 | Triplett et al. |
| 2002/0147670 A1 | 10/2002 | Lange |
| 2003/0050901 A1 | 3/2003 | Jester et al. |
| 2003/0195822 A1 | 10/2003 | Tatge et al. |
| 2003/0236738 A1 | 12/2003 | Lange et al. |
| 2005/0008619 A1 | 1/2005 | Park et al. |
| 2005/0070435 A1 | 3/2005 | Chopade et al. |
| 2005/0072047 A1 | 4/2005 | Conkling et al. |
| 2006/0046246 A1 | 3/2006 | Zeng et al. |
| 2006/0178269 A1 | 8/2006 | Medina-Vega |
| 2006/0185207 A1 | 8/2006 | Mitcheltree |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2009/0300781 A1 | 12/2009 | Bancroft et al. |
| 2010/0064392 A1 | 3/2010 | Yang et al. |
| 2010/0095396 A1 | 4/2010 | Voeste et al. |
| 2010/0114753 A1 | 5/2010 | Osmanski et al. |
| 2010/0130365 A1 | 5/2010 | Notten et al. |
| 2010/0205690 A1 | 8/2010 | Blasing et al. |
| 2010/0227357 A1 | 9/2010 | Redman et al. |
| 2011/0033436 A1 | 2/2011 | Chen et al. |
| 2011/0182862 A1 | 7/2011 | Green et al. |
| 2011/0195406 A1 | 8/2011 | Sorenson et al. |
| 2012/0108431 A1 | 5/2012 | Williams et al. |
| 2012/0116943 A1 | 5/2012 | Abramson |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0134629 A1 | 5/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0218568 A1 | 8/2015 | Jones et al. |
| 2015/0230478 A1 | 8/2015 | Vujanovic et al. |
| 2015/0242970 A1 | 8/2015 | Avey et al. |
| 2015/0282490 A1 | 10/2015 | Wachendorff-Neumann et al. |
| 2015/0289518 A1 | 10/2015 | Andersch et al. |
| 2015/0296802 A1 | 10/2015 | Wachendorff-Neumann et al. |
| 2015/0296803 A1 | 10/2015 | Andersch et al. |
| 2015/0296804 A1 | 10/2015 | Andersch et al. |
| 2015/0305348 A1 | 10/2015 | Andersch et al. |
| 2015/0320050 A1 | 11/2015 | von Maltzahn et al. |
| 2015/0320051 A1 | 11/2015 | Wachendorff-Neumann et al. |
| 2015/0335029 A1 | 11/2015 | Mitter et al. |
| 2015/0342199 A1 | 12/2015 | Carrion Villanovo et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0000091 A1 | 1/2016 | Andersch et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0350855 A1 | 12/2016 | Lerner |
| 2016/0366892 A1 | 12/2016 | Ambrose et al. |
| 2017/0020138 A1 | 1/2017 | Von Maltzahn et al. |
| 2017/0064361 A1 | 3/2017 | Pinca, IV et al. |
| 2017/0161560 A1 | 6/2017 | Itzhaky et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0060771 A1 | 3/2018 | Mangin |
| 2018/0092365 A1 | 4/2018 | Sword |
| 2018/0153174 A1 | 6/2018 | Riley et al. |
| 2018/0177196 A1 | 6/2018 | Sword |
| 2018/0189564 A1 | 7/2018 | Freitag et al. |
| 2018/0213800 A1 | 8/2018 | Djonovic et al. |
| 2018/0249716 A1 | 9/2018 | Riley |
| 2018/0251776 A1 | 9/2018 | Riley |
| 2018/0322426 A1 | 11/2018 | Schmaltz et al. |
| 2019/0130999 A1 | 5/2019 | Oppenheim et al. |
| 2021/0372997 A1 | 12/2021 | Von Maltzahn et al. |

FOREIGN PATENT DOCUMENTS

| | | |
|---|---|---|
| CA | 1229497 A | 11/1987 |
| CA | 2562175 A1 | 4/2008 |
| CA | 2916678 A1 | 12/2014 |
| CA | 2960032 A1 | 3/2015 |
| CA | 2935218 A1 | 7/2015 |
| CA | 2953466 A1 | 12/2015 |
| CA | 2953697 A1 | 12/2015 |
| CN | 1604732 A | 4/2005 |
| CN | 1948459 A | 4/2007 |
| CN | 101311262 A | 11/2008 |
| CN | 101423810 A | 5/2009 |
| CN | 101570738 A | 11/2009 |
| CN | 101693881 A | 4/2010 |
| CN | 102010835 A | 4/2011 |
| CN | 102123596 A | 7/2011 |
| CN | 102168022 A | 8/2011 |
| CN | 102352327 A | 2/2012 |
| CN | 102533601 A | 7/2012 |

(56) References Cited

FOREIGN PATENT DOCUMENTS

| | | |
|---|---|---|
| CN | 103642725 A | 3/2014 |
| CN | 103865837 | 6/2014 |
| CN | 104250616 A | 12/2014 |
| CN | 104388356 A | 3/2015 |
| CN | 104560742 A | 4/2015 |
| CN | 105886428 | 8/2016 |
| CN | 106434493 | 2/2017 |
| EP | 0192342 A2 | 8/1986 |
| EP | 0223662 A1 | 5/1987 |
| EP | 0378000 A2 | 7/1990 |
| EP | 0494802 A1 | 7/1992 |
| EP | 0818135 A1 | 1/1998 |
| EP | 1389767 | 2/2004 |
| EP | 1621632 A1 | 2/2006 |
| EP | 1935245 A1 | 6/2008 |
| EP | 1967057 | 9/2008 |
| EP | 2114118 | 9/2012 |
| EP | 2676536 A1 | 12/2013 |
| EP | 2959779 | 12/2015 |
| EP | 3041338 | 7/2016 |
| EP | 3659414 | 6/2020 |
| JP | 2003300804 A | 10/2003 |
| JP | 2009/072168 A | 4/2009 |
| KR | 20050039979 | 5/2005 |
| KR | 20100114806 A | 10/2010 |
| KR | 101066283 | 9/2011 |
| KR | 101091151 B1 | 12/2011 |
| KR | 20120004958 | 1/2012 |
| KR | 20130023491 A | 3/2013 |
| RU | 2043028 C1 | 9/1995 |
| WO | 1988/009114 | 1/1988 |
| WO | 1994/016076 | 7/1994 |
| WO | 98/35017 | 8/1998 |
| WO | 99/59412 | 11/1999 |
| WO | 2000/029607 A1 | 5/2000 |
| WO | 2001/046774 | 12/2000 |
| WO | 2001/083697 A2 | 11/2001 |
| WO | 2001/083818 A2 | 11/2001 |
| WO | 2002/065836 A2 | 8/2002 |
| WO | 2003/038066 | 5/2003 |
| WO | 2004/046357 A1 | 6/2004 |
| WO | 2005/003328 A1 | 1/2005 |
| WO | 2007/021200 A1 | 2/2007 |
| WO | 2007/107000 A1 | 9/2007 |
| WO | 2008/103422 A2 | 8/2008 |
| WO | 2008/107097 | 9/2008 |
| WO | 2009/012480 A2 | 1/2009 |
| WO | 2009/078710 A1 | 6/2009 |
| WO | 2009/126473 A1 | 10/2009 |
| WO | 2010/109436 A1 | 9/2010 |
| WO | 2010/115156 A2 | 10/2010 |
| WO | 2011/001127 A1 | 1/2011 |
| WO | 2011/011627 A1 | 1/2011 |
| WO | 2011/082455 A1 | 7/2011 |
| WO | 2011/112781 A2 | 9/2011 |
| WO | 2011/117351 A1 | 9/2011 |
| WO | 2012/016140 | 2/2012 |
| WO | 2012/034996 A1 | 3/2012 |
| WO | 2013/016361 A1 | 1/2013 |
| WO | 2013/029112 A1 | 3/2013 |
| WO | 2013/054272 | 4/2013 |
| WO | 2013/090628 A1 | 6/2013 |
| WO | 2013/122473 A1 | 8/2013 |
| WO | 2013/148290 | 10/2013 |
| WO | 2013/177615 A1 | 12/2013 |
| WO | 2013/190082 A1 | 12/2013 |
| WO | 2014/046553 A1 | 3/2014 |
| WO | 2014/079728 | 5/2014 |
| WO | 2014/082950 A1 | 6/2014 |
| WO | 2014/086747 | 6/2014 |
| WO | 2014/086749 | 6/2014 |
| WO | 2014/086750 | 6/2014 |
| WO | 2014/086752 | 6/2014 |
| WO | 2014/086753 | 6/2014 |
| WO | 2014/086756 | 6/2014 |
| WO | 2014/086758 | 6/2014 |
| WO | 2014/086759 | 6/2014 |
| WO | 2014/086764 | 6/2014 |
| WO | 2014/086776 | 6/2014 |
| WO | 2014/121366 A1 | 8/2014 |
| WO | 2014/206953 A1 | 12/2014 |
| WO | 2014/210372 A1 | 12/2014 |
| WO | 2015/035099 A2 | 3/2015 |
| WO | 2015/069938 A1 | 5/2015 |
| WO | 2015/100431 A2 | 7/2015 |
| WO | 2015/100432 A2 | 7/2015 |
| WO | 2015/114552 | 8/2015 |
| WO | 2015/116838 | 8/2015 |
| WO | 2015/192172 A1 | 12/2015 |
| WO | 2015/200852 A2 | 12/2015 |
| WO | 2015/200902 A2 | 12/2015 |
| WO | 2016020371 | 2/2016 |
| WO | WO 2016020371 * | 2/2016 |
| WO | 2016/050726 | 4/2016 |
| WO | 2016/057991 A1 | 4/2016 |
| WO | 2016/090212 A1 | 6/2016 |
| WO | 2016/109758 A2 | 7/2016 |
| WO | 2016/179046 A1 | 11/2016 |
| WO | 2016/179047 A1 | 11/2016 |
| WO | 2016/200987 A1 | 12/2016 |
| WO | 2018094027 | 5/2018 |
| WO | 2018/119419 | 6/2018 |
| WO | 2018102733 A1 | 6/2018 |
| WO | 2018160244 A1 | 9/2018 |
| WO | 2018160245 A1 | 9/2018 |
| WO | 2019/046909 | 3/2019 |
| WO | 2019084380 | 5/2019 |
| WO | 2019113468 | 6/2019 |

OTHER PUBLICATIONS

Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.

Redman, R. S., et al., "Thermotolerance Generated by Plant/Fungal Symbiosis," Science, Nov. 2002, vol. 298, 1 Page (with 4 pages of supplemental material).

Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.

Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.

Result 11 from a search in the GenEmbl database, GenEmbl Record No. EU 977189, Smith et al., "Bioactive endophytes warrant intensified exploration and conservation," PLoS ONE 3(8):E3052, 2008.

Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.

Riess, K., et al., "High genetic diversity at the regional scale and possible speciation in Sebacina epigaea and S. incrustans," BMC Evolutionary Biology, 2013, vol. 13, No. 102, 17 Pages.

Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.

Rodriguez, H., et al., "Expression of a Mineral Phosphate Solubilizing Gene From Erwinia herbicola in Two Rhizobacterial Strains," J Biotechnol., 2001, pp. 155-161, vol. 84.

Rodriguez, R.J., et al., "Stress Tolerance in Plants via Habitat-Adapted Symbiosis," ISME J., 2008, pp. 404-416, vol. 2.

Rodriguez-Navarro, D., et al., "Soybean Interactions with Soil Microbes, Agronomical and Molecular Aspects," Agronomy for Sustainable Development, 2011, pp. 173-190, vol. 31, No. 1.

Roessner, U., et al., "Metabolic Profiling Allows Comprehensive Phenotyping of Genetically or Environmentally Modified Plant Systems," Plant Cell, 2001, pp. 11-29, vol. 13.

(56) References Cited

OTHER PUBLICATIONS

Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.

Rosenblueth, A., et al., "Seed Bacterial Endophytes: Common Genera, Seed-to-Seed Variability and Their Possible Role in Plants," Acta Hort., 2012, pp. 39-48, vol. 938.

Rosenblueth, M., et al., "Bacterial Endophytes and Their Interactions With Host," Molecular Plant-Microbe Interactions, 2006, pp. 827-837, vol. 19, No. 8.

Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.

Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.

Samac, D.A., et al., "Recent Advances in Legume-Microbe Interactions: Recognition, Defense Response, and Symbiosis from a Genomic Perspective," Plant Physiol., 2007, pp. 582-587, vol. 144.

Samways, M.J., et al., "Assessment of the Fungus Cladosporium Oxyspoum (Berk. and Curt.) As a Potential BioControl Agent Against Certain Homoptera," Elsevier Science Publishers B.V., Jan. 1, 1986, pp. 231-239.

Sardi, P, et al., "Isolation of Endophytic Streptomyces Strains from Surface Sterilized Roots," Applied and Environmental Microbiology, 1992, pp. 2691-2693, vol. 58, No. 8.

Sarkar, S., et al., "New report of additional enterobacterial species causing wilt in West Bengal, India," Canadian Journal of Microbiology, 2015, vol. 61, No. 7, pp. 477-486.

Sarwar, M., et al., "Tryptophan Dependent Biosynthesis of Auxins in Soil," Plant Soil, 1992, pp. 207-215, vol. 147.

Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74, No. 1.

Schmieder, R., et al., "Quality Control and Preprocessing of Metagenomic Datasets," Bioinformatics, 2011, pp. 863-864, vol. 27, No. 6.

Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.

Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.

Schwyn, B. et al., "Universal Chemical Assay for the Detection and Determination of Siderophores," Analytical Biochemistry, 1987, pp. 47-56, vol. 160.

Senthilkumar, M., et al., "Biocontrol Potential of Soybean Bacterial Endophytes Against Charcoal Rot Fungus, Rhizoctonia batatiola," Current Microbiology, 2009, vol. 58, pp. 288-293.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Sha, T. et al., "Genetic diversity of the endemic gourmet mushroom Thelephora ganbajun from southwestern China", Microbiology (2008), 154, 3460-3468.

Shankar, M., et al., "Root colonization of a rice growth promoting strain of Enterobacter cloacae," Journal of Basic Microbiology, 2011, pp. 523-530, vol. 51.

Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.

Sharma et al., "Detection and identification of bacteria intimately associated with fungi of the order Sebacinales", Cellular Microbiology, Aug. 5, 2008, pp. 2235-2246, vol. 10, No. 11.

Shiraishi, A., et al., "Nodulation in black locust by the ammaproteobacteria *Pseudomonas* sp. and the Betaproteobacteria *Burkholderia* sp", Systematic and Applied Microbiology, vol. 33, No. 5, Aug. 2010, pp. 269-274.

Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.

Singh, A K., et al., "Uncultured *Actinomyces* sp. Clone Emlact 80 IV (New) 16S Ribosomal RNA Gene, Partial Sequence," NCBI GenBank Accession No. JQ285908. Submitted Dec. 13, 2011, 1 page.

Soares, M. M. C. N., et al., "Screening of Bacterial Strains for Pectinolytic Activity: Characterization of the Polygalacturonase Produced by Bacillus SP," Revista de Microbiolgia, 1999, pp. 299-303, vol. 30.

Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.

Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Genmination of Hordeum brevisubulatum under Temperature and Water Stress Conditions," Acta Agrestia Sinica, 2010, pp. 834-837, vol. 18, No. 6. (English Abstract).

Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by Rhizobium tropici," Arch Microbiol., 2012, pp. 197-206, vol. 194.

Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.

Strobel, G. A., "Endophytes as Sources of Bioactive Products," Microbes and Infection, 2003, pp. 535-544, vol. 5.

Sturz, A. V., et al., "Weeds as a Source of Plant Growth Promoting Rhizobacteria in Agricultural Soils," Can J Microbiol., 2001, pp. 1013-1024, vol. 47, No. 11.

Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.

Surette, M.A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.

Suto, M., et al., "Endophytes as Producers of Xylanase," J Biosci Bioeng., 2002, pp. 88-90, vol. 93, No. 1.

Sword, G., "Fungal Endophytes to Protect Cotton from Insects and Nematodes," Power Point Presentation dated Dec. 7, 2012, 20 Pages.

Sword, G., "Manipulating Fungal Endophytes to Protect Plants from Insects and Nematodes," Power Point Presentation dated Aug. 7, 2013, 48 Pages.

Sword, G., "Natural Enemies—The Forgotten Basis of IPM?," Power Point Presentation dated Sep. 6, 2013, 33 Pages.

(56) References Cited

OTHER PUBLICATIONS

Sword, G., et al., "Field Trials of Potentially Beneficial Fungal Endophytes in Cotton," Power Point Presentation dated Jan. 7, 2013, 17 Pages.
Sword, G., et al., "Manipulating Fungal Endophytes for the Protection of Cotton in the Field," Power Point Presentation dated Jan. 7, 2013.
Taghavi, S., et al., "Genome Sequence of the Plant Growth promoting Endophytic Bacterium *Enterobacter* sp. 638", PLoS Genet., May 2010, vol. 6, Issue 5, e1000943, pp. 1-15.
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Tamura, K., et al., "Estimation of the number of nucleotide substitutions in the control region of mitochondrial DNA in humans and chimpanzees," Molecular Biology and Evolution, 1993, vol. 10, No. 3, pp. 512-526.
Taylor, A.G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in *Spodoptera litura* (Lepidoptera: Noctuidae) Larvae by Endophytic Fungi Nigrospora oryzae and Cladosporium uredinicola,", Annals of the Entomological Society of America, May 1, 2014, pp. 674-679, vol. 107, No. 3.
Theis, K. R., et al., "Uncultured Bacterium Clone GM2GI8201A64RC 16S Ribosomal RNA Gene, Partial Sequence," NCBI GenBank Accession No. JX051943, Submitted May 14, 2012, 1 Page.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving Streptomyces Lydicus WYEC108 and the Pea Plant (*Pisum sativum* )," Applied and Environmental Microbiology, May 2002, pp. 2161-2171, vol. 68, No. 5.
Trichoderma definition, 2016, 6 Pages, [online] [Retrieved on Sep. 16, 2016,] Retrieved from the Internet <URL: https://en.wikipedia.org/wiki/Trichoderma>.
Trotel-Aziz, P., et al., "Characterization of New Bacterial Biocontrol Agents *Acinetobacter, Bacillus, Pantoea and Pseudomonas* spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
U'Ren, J.M., et al., "Host and geographic structure of endophytic and endolichenic fungi at the continental scale," American Journal of Botany, May 1, 2012, pp. 898-914, vol. 99, No. 5.
United States Patent Office, Final Office Action, U.S. Appl. No. 14/614,193, dated Dec. 22, 2016, 13 Pages.
United States Patent Office, Final Office Action, U.S. Appl. No. 14/410,537, dated May 5, 2017, 9 Pages.
United States Patent Office, Final Office Action, U.S. Appl. No. 14/614,193, dated Jul. 18, 2017, 14 Pages.
United States Patent Office, Final Office Action, U.S. Appl. No. 14/614,193, dated May 3, 2018, 10 Pages.
United States Patent Office, Final Office Action, U.S. Appl. No. 14/964,429, dated May 31, 2017, 9 Pages.
United States Patent Office, Final Office Action, U.S. Appl. No. 15/107,973, dated Jan. 26, 2018, 20 Pages.
United States Patent Office, Final Office Action, U.S. Appl. No. 15/034,862, dated Jan. 12, 2018, 14 Pages.
United States Patent Office, Non-Final Office Action, U.S. Appl. No. 14/766,065, dated Oct. 27, 2017, 11 Pages.
United States Patent Office, Non-Final Office Action, U.S. Appl. No. 14/964,429, dated Aug. 9, 2016, 6 Pages.
United States Patent Office, Non-Final Office Action, U.S. Appl. No. 15/034,862, dated May 19, 2017, 8 Pages.
United States Patent Office, Non-Final Office Action, U.S. Appl. No. 15/063,350, dated Nov. 10, 2016, 18 Pages.
United States Patent Office, Non-Final Office Action, U.S. Appl. No. 15/107,973, dated Apr. 10, 2017, 39 Pages.
United States Patent Office, Non-Final Office Action, U.S. Appl. No. 15/212,038, dated Sep. 21, 2016, 10 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
United States Patent Office, Non-Final Office Action, U.S. Appl. No. 15/143,398, dated Sep. 22, 2017, 16 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/107,965, dated Jun. 21, 2018, 27 Pages.
United States Patent Office, Non-Final Office Action, U.S. Appl. No. 15/143,394, dated Sep. 25, 2017, 15 Pages.
United States Patent Office, Non-Final Office Action, U.S. Appl. No. 15/143,398, dated Sep. 22, 2017, 17 Pages.
Usadel, B., et al., "The Plant Transcriptome—From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013, 10 Pages.
Valencia, E., et al., "Mini-review: Brazilian fungi diversity for biomass degradation," Fungal Genetics and Biology, 2013, pp. 9-18, vol. 60.
Van Der Lelie, D., et al., "Poplar and its Bacterial Endophytes: Coexistence and Harmony," Critical Rev Plant Sci., 2009, pp. 346-358, vol. 28.
Verkley, G., et al., "*Paraconiothyrium*, a new genus to accommodate the mycoparasite Coniothyrium minitans, anamorphs of Paraphaeosphaeria, and four new species," Studies in Mycology, 2004,; pp. 323-335, vol. 50.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "Pseudomonas thiveralensis Strain IEHa 16S Ribosomal RNA Gene, Partial Sequence," NCBI GenBankAccession No. GQ169380.1, Submitted May 15, 2009, 1 Page.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report and Written Opinion for PCT/US2017/064292, dated May 11, 2018, 20 Pages.
PCT International Search Report and Written Opinion for PCT/US2017/064361, dated May 11, 2018, 22 Pages.
PCT International Search Report and Written Opinion for PCT/US2018/051467, dated Feb. 4, 2019, 22 pages.
PCT International Search Report and Written Opinion PCT/AU2018/050387, dated Jul. 12, 2018 (Filing date is Apr. 27, 2018).
PCT International Search Report and Written Opinion, Application No. PCT/AU2015/000360, dated Aug. 5, 2015, 12 Pages.
PCT International Search Report and Written Opinion, Application No. PCT/US2014/054160, dated Dec. 9, 2014, 21 Pages.
PCT International Search Report and Written Opinion, Application No. PCT/US2014/072400, dated Jul. 8, 2015, 38 Pages.

(56) References Cited

OTHER PUBLICATIONS

PCT International Search Report and Written Opinion, International Application No. PCT/US2014/064411, dated Mar. 27, 2015, 15 Pages.
PCT International Search Report and Written Opinion, International Application No. PCT/US2014/072399, dated Jun. 26, 2015, 22 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT International Search Report and Written Opinion, PCT Application No. PCT/US2017/064292, dated May 11, 2018, 20 Pages.
PCT International Search Report and Written Opinion, PCT Application No. PCT/US2017/064351, dated Apr. 9, 2018, 25 Pages.
PCT International Search Report and Written Opinion, PCT Application No. PCT/US2017/068255, dated Mar. 19, 2018, 14 Pages.
PCT International Search Report and Written Opinionfor PCT/US2018/051467, dated Mar. 25, 2019 26 pages.
PCT International Search Report, Application No. PCT/US2014/044427, dated Dec. 3, 2014, 9 Pages.
PCT Invitation to Pay Additional Fees, PCT Application No. PCT/US2017/064292, dated Mar. 5, 2018, 15 Pages.
PCT Invitation to Pay Additional Fees, PCT Application No. PCT/US2017/064292, dated Mar. 5, 2018, 15 Pages. (Attached document is dated Mar. 6, 2018 and is 16 pages).
PCT Invitation to Pay Additional Fees, PCT Application No. PCT/CA2013/000091, dated Mar. 27, 2013, 2 Pages.
PCT Invitation to Pay Additional Fees, PCT Application No. PCT/US2014/064411, dated Feb. 5, 2015, 2 Pages.
PCT Invitation to Pay Additional Fees, PCT Application No. PCT/US2014/072399, dated Apr. 14, 2015, 2 Pages.
PCT Invitation to Pay Additional Fees, PCT Application No. PCT/US2014/072400, dated Apr. 16, 2015, 6 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT Invitation to Pay Additional Fees, PCT Application No. PCT/US2015/068206, dated Apr. 12, 2016, 5 Pages.
PCT Invitation to Pay Additional Fees, PCT Application No. PCT/US2017/064351, dated Feb. 9, 2018, 18 Pages.
PCT Invitation to Pay Additional Fees, PCT Application No. PCT/US2017/064361, dated Mar. 7, 2018, 18 Pages.
Pearson, W.R., et al., "Rapid and Sensitive Sequence Comparison With FASTP and FASTA," Methods Enzymol., 2011, pp. 63-98, vol. 183.
Pedraza, R.O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Fernandez, M.A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, [online][Retrieved Aug. 11, 2016] Retrieved from the Internet URL:http://www.philrice.gov.ph/2012-rd-highlights/, 52 Pages.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval *Helicoverpa zea* (Lepidoptera: Noctuidae)," J. Entomol. Sci., 2009, pp. 391-396, vol. 44, No. 4.
Quadt-Hallmann, A, et al., "Bacterial Endophytes in Cotton: Mechanisms of Entering the Plant," Can J Microbiol., 1997, pp. 577-582, vol. 43.
R Core Team, "R: A Language and Environment for Statistical Computing," R Foundation for Statistical Computing, Vienna, Austria, May 2013, ISBN: 3-900051-07-0. Available online at http://www.R-25project.org/, 3604 Pages.
Rae, R., et al., "A subset of naturally isolated Bacillus strains show extreme virulence to the free-living nematodes Caenorhabditis elegans and Pristionchus pacificus", Environmental Microbiology, vol. 12, No. 11, 2010, pp. 3007-3021.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hain, T., et al., "Chitinolytic transgenes from Streptomyces albidoflavus as phytochemicals defences against; herbivorous insects, use in transgenic plants and effect in plant development", International Journal of Systematic Bacteriology, Jan. 1997, vol. 47, No. 1, pp. 202-206.
Hallman, J., et al., "Bacterial Endophytes in Agricultural Crops," Canadian J Microbiol., 1997, pp. 895-914, vol. 43.
Hamayun, M., et al., "Cladosporium sphaerospermum as a new plant growth-promoting endophyte from the roots of *Glycine max*(L.) Merr," World Journal of Microbiology and Biotechnology, Kluwer Academic Publishers, DO, vol. 25, No. 4, Feb. 15, 2009 (Feb. 15, 2009), pp. 627-632.
Hanshew, A., et al., "Characterization of Actinobacteria Associated with Three Ant-Plant Mutualisms", Microbiol Ecology, August, 6, 2014, vol. 69, No. 1, pp. 192-203.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, LE., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P.R., et al., "Dynamics of Seed-Borne Rice Endophytes on Early Plant Growth Stages," PLoS ONE, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).

(56) References Cited

OTHER PUBLICATIONS

Hepler, P. K., et al., "Polarized Cell Growth in Higher Plants," Annu Rev Cell Dev Biol., 2001, pp. 159-187, vol. 17.
Hiatt, E.E., et al., "Tall Fescue Endophyte Detection: Commerical Immunoblot Test Kit Compared with Microscopic Analysis," Crop Science, 1999, pp. 796-799, vol. 39.
Hibbett, D.S., et al., "A Higher-Level Phylogenetic Classification of the Fungi," Mycol Res., 2007, pp. 509-547, vol. 111.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hill, N. S., et al., "Endophyte Survival during Seed Storage: Endophyte-Host Interactions and Heritability," Crop Sci., 2009, pp. 1425-1430, vol. 49.
Hinton, D. M., et al., "Enterobacter cloacae is an endophytic symbiont of corn," Mycopathologia, 1995, pp. 117-125, vol. 129.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., "Fungal Endophytes that Confer Heat and Drought Tolerance to Wheat," Doctoral dissertation, University of Saskatchewan, 2012.
Hubbard, M., et al., "Fungal Endophytes Improve Wheat Seed Germination Under Heat and Drought Stress," Botany, 2012, pp. 137-149, vol. 90.
Hubbard, M., et al., 2011. "Agricultural Potential of Fungal Endophytes of Grasses, Cereals and Wheat," In: Wheat: Genetics, Crops and Food Production. Nova Science Publishers Hauppauge, pp. 333-345.
Humann, J., et al., "Complete genome of the onion pathogen Enterobacter cloacae EcWSU1 ," Standard in Genomic Sciences, Dec. 31, 2011, vol. 5, No. 3, pp. 279-286.
Hung, P.Q., et al., "Isolation and Characterization of Endophytic Bacteria in Soybean (*Glycine* sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year: 2003).
Ikeda, S., et al., "The Genotype of The Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Impullitti, A.E., et al., "Fungal endophyte diversity in soybean", Journal of Applied Microbiolog, vol. 114, No. 5, May 1, 2013, pp. 1500-1506.
International Search Report and Written Opinion for PCT/EP2013/062976, dated Dec. 22, 2014, 9 Pages.
International Search Report and Written Opinion, Application No. PCT/US2014/054160, dated Dec. 9, 2014, 21 Pages.
International Search Report and Written Opinion, Application No. PCT/US2014/072400, dated Jul. 8, 2015, 38 Pages.
International Search Report and Written Opinion, International Application No. PCT/US2014/064411, dated Mar. 27, 2015, 15 Pages.
International Search Report and Written Opinion, International Application No. PCT/US2014/072399, dated Jun. 26, 2015, 22 Pages.
Invitation to Pay Additional Fees, PCT Application No. PCT/CA2013/000091, dated Mar. 27, 2013, 2 Pages.
Invitation to Pay Additional Fees, PCT Application No. PCT/US2014/064411, dated Feb. 5, 2015, 2 Pages.
Invitation to Pay Additional Fees, PCT Application No. PCT/US2014/072400, dated Apr. 16, 2015, 6 Pages.
Invitation to Pay Additional Fees, PCT Application No. PCT/US2015/038110, dated Sep. 22, 2015, 8 Pages.
Invitation to Pay Additional Fees, PCT Application No. PCT/US2015/038187, dated Oct. 14, 2015, 5 Pages.
Iverson, C., et al, "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter* genomospecies I", BMC Evolutionary Biology 2007, Apr. 17, 2017, 11 pages.
Jalgaonwala, R., et al., "A Review on Microbiol Endophytes from Plants: A Treasure Search for Biologically Active Metabolites," Global Journal of Research on Medicinal Plants & Indigenous Medicine, 2014, pp. 263-277, vol. 3, No. 6.
Janda, J.M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Joe, M.M. et al., "Development of alginate-based aggregate inoculants of *Methylobacterium* sp. and Azospirillum brasilense tested under in vitro conditions to promote plant growth," Journal of Applied Microbiology 2013, 116 (2):408-423, XP055225426, Nov. 22, 2013.
Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.
Johnston-Monje, D., et al., "Conservation and Diversity of Seed Associated Endophytes in *Zea* Across Boundaries of Evolution, Ethnography and Ecology," PLoS ONE, 2011, vol. 6, No. 6, 22 Pages.
Johnston-Monje, D., et al., "Plant and Endophyte Relationships: Nutrient Management," Comprehensive Biotechnol., 2011, pp. 713-727, vol. 4.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013, 17 Pages.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.
Kasana, R. C., et al., "A Rapid and Easy Method for the Detection of Microbial Cellulases on Agar Plates Using Gram's Iodine," Curr Microbiol., 2008, pp. 503-507, vol. 57.
Khan, A.L., et al., "Salinity Stress Resistance Offered by Endophytic Fungal Interaction Between Penicillium minioluteum LHL09 and *Glycine max*. L," J. Microbiol. Biotechnol., 2011, pp. 893-902, vol. 21, No. 9.
Kim, M., et al., "Towards a taxonomic coherence between average nucleotide identity and 16S rRNA gene sequence similarity for

(56) References Cited

OTHER PUBLICATIONS species demarcation of prokaryotes", Int J Systematic Evolutionary Microbiol., 2014, vol. 64, pp. 346-351.

Klaubauf, S., et al., "Molecular diversity of fungal communities in agricultural soils from Lower Austria," Fungal Diversity, Aug. 13, 2010, pp. 65-75, vol. 44, No. 1.

Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.

Kruger, M., et al., "DNA-Based Species Level Detection of Glomeromycota: One PCR Primer Set for All Arbuscular Mycorrhizal Fungi," New Phytol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Kuklinsky-Sobral, J., et al., "Isolation and characterization of soybean-associated bacteria and their potential for plant growth promotion," Environmental Microbiology, 2004, pp. 1244-1251, vol. 6, No. 12.

Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.

Kumar, S., et al., "MEGA7: Molecular Evolutionary Genetics Analysis version 7.0 for bigger datasets," Molecular Biology and Evolution, Mar. 22, 2016, vol. 33, pp. 1870-1874.

Kusari, S., et al. "Chemical ecology of endophytic fungi: origins of secondary metabolites," Cell Press, Chem & Biol, vol. 19, pp. 792-798, 2012.

Labeda, D.P., et al., "Phylogenetic study of the species within the family Streptomycetaceae," Antonie van Leeuwenhoek, 2012, vol. 101, pp. 73-104, Springer.

Langille, M.G.I. et al., "Predictive functional profiling of microbial communities using 16S rRNA marker; gene sequences," Nature Biotechnology, 2013, vol. 31, No. 9, pp. 814-821.

Lanver, D., et al., "Sho1 and Msb2-Related Proteins Regulate Appressorium Development in the Smut Fungus Ustilago aydis," Plant Cell, 2010, pp. 2085-2101, vol. 22.

Laus, M. C., et al., "Role of Cellulose Fibrils and Exopolysaccharides of Rhizobium leguminosarum in Attachment to and Infection of Vicia sativa Root Hairs," Mol Plant Microbe Internet., 2005, pp. 533-538, vol. 16, No. 6.

Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.

Le, X.H., et al., "Isolation and characterisation of endophytic actinobacteria and their effect on the early growth and hodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.

Lee, J., et al., "*Streptomyces koyangensis* sp. nov., a novel actinomycete that produces 4-phenyl-3-butenoic acid," Int J Syst Evol Microbial. Jan. 2005;55(Pt 1):257-62. (Year: 2005).

Lehman, S.G., "Treat Cotton Seed," Research and Farming III, Progr. Rept., 1945, 3, 5, 16 Pages.

Lehman, S.G., "Treat Cotton Seed," Review of Applied Mycology, 1945, 24, 369, 16 Pages.

Leonard, C. A., et al., "Random Mutagenesis of the Aspergillus oryzae Genome Results in Fungal Antibacterial Activity," Int J Microbiol., 2013, vol. 2013, Article ID 901697, 6 Pages.

Li, H. M., et al., "Expression of a Novel Chitinase by the Fungal Endophyte in Poa ampla," Mycologia, 2004, pp. 626-536, vol. 96, No. 3.

Li, H., et al., "Endophytes and their role in phytoremediation," Fungal Diversity, 2012, pp. 11-18, vol. 54.

Li, M., et al., "ATP Modulates the Growth of Specific Microbial Strains", Current Microbiology, May 30, 2010, vol. 62, No. 1, pp. 84-89.

Li, Q., "Agrobacterium tumefaciens Strain TA-AT-10 16S Ribosomal RNA Gene, Partial Sequence: GenBank: KF673157.1," Submitted Dec. 16, 2013.

Lind, A., et al., "Drivers of genetic diversity in secondary metabolic gene clusters within a fungal species", PLOS Biology, Nov. 17, 2017, 26 pages.

Liu, D., et al., "Osmotin Overexpression in Potato Delays Development of Disease Symptoms," Proc Natl Acad Sci USA, 1994, pp. 1888-1892, vol. 91.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.

Liu, Y., et al., "Phylogenetic relationships among ascomycetes: evidence from an RNA polymerase II subunit," Mol. Biol. Evol. 1999. Vol. 16, No. 12, pp. 1799-1808.

Liu, Y., et al., "Study on Diversity of Endophytic Bacterial Communities in Seeds of Hybrid Maize and their Parental Lines," Arch Microbiol., 2012, pp. 1001-1012, vol. 194.

Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.

Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.

Lorck, H., "Production of Hydrocyanic Acid by Bacteria," Physiol Plant, 1948, pp. 142-146, vol. 1.

Lugtenberg, B., et al., "Plant-Growth-Promoting Rhizobacteria," Ann. Rev. Microbiol., 2009, pp. 541-556, vol. 63.

Lundberg, D.S., et al., "Defining the Core *Arabidopsis thaliana*Root Microbiome," Nature, 2012, pp. 86-90, vol. 188, No. 7409.

Lundberg, D.S., et al., "Practical Innovations for High-Throughput Amplicon Sequencing," Nat Methods, 2013, pp. 999-1002, vol. 10, No. 10.

Ma, Y., et al., "Plant Growth Promoting Rhizobacteria and Endophytes Accelerate Phytoremediation of Metalliferous Soils," Biotechnology Advances, 2011, pp. 248-258, vol. 29.

Madi, L. et al., "Aggregation in Azospirillum brasilense Cd: Conditions and Factors Involved in Cell-to-Cell Adhesion," Plant Soil, 1989, pp. 89-98, vol. 115.

Mandyam, K., et al., "Mutualism-parasitism paradigm synthesized from results of root-endophyte models", Frontiers in Microbiology, vol. 5, Jan. 12, 2015, pp. 1-14.

Mannisto, M.K., et al., "Characterization of Psychrotolerant Heterotrophic Bacteria From Finnish Lapland," Syst Appl Microbiol., 2006, pp. 229-243, vol. 29.

Mano, H., et al., "Culturable Surface and Endophytic Bacterial Flora of the Maturing Seeds of Rice Plants (*Oryza saliva*) Cultivated in a Paddy Field," Microbes Environ., 2006, vol. 21, No. 2.

Manoharan, M. J. et al., "Survival of flocculated cells in alginate and its inoculatin effect on growth and yield of maize under water deficit conditions," Ep J of Soil Biology, Gauthier-Villars, Montrouge, FR, vol. 50, Mar. 7, 2012, pp. 198-206, XP028421147.

Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.

Mao, W., et al., "Seed Treatment with a Fungal or a Bacterial Antagonist for Reducing Corn Damping-off Caused by Species of Pythium and Fusarium," Plant Disease, 1997, pp. 450-454, vol. 81, No. 5.

Marasco, R., et al., "A Drought Resistance-Promoting Microbiome is Selected by Root System Under Desert Farming," PLoS ONE, 2012, vol. 7, No. 10, 14 Pages.

(56) References Cited

OTHER PUBLICATIONS

Sato, I., et al., "Suppressive Potential of Paenibacillus Strains Isolated from the Tomato Phyllosphere against Fusarium Crown and Root Rot of Tomato", Microbes Environ, vol. 29, No. 2, 168-177, 2014.

Soe, K.M, et al., "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).

Ngom, A et al., "A novel symbiotic nitrogen-fixing member of the Ochrobactrum clade isolated from root nodues of Acacia mangium". J. Gen. Appl. Microbiol. (2004) 50: 17-27.

Trujillo, M.E et al., "Nodulation of Lupinus albus by strins of *Ochrobactrum lupini* sp. nov." Appl. Environ Microbiol Mar. 2005; 71(3): 1318-1327.

Bal, H.B et al., "Isolation of ACC deaminase producting PGPR from rice rhizosphere and evaluating their plant growth promoting activity under salt stress". Plant Soil (2013) 366: 93-105 doi: 10/1007/s11104-012-1402-5.

Chakraborty et al., "Evaluation of Ochrobactrum anthropi TRS-2 and its talcbased formulation for enhancement of growth of tea plants and management of brown root rot disease." Journal of Applied Microbiology, 2009, 107(2):625-634 DOI:10.1111/j.1365-2672.2009.04242.x <https://doi.org/10.1111/j.1365-2672.2009.04242.x.

Sulistiyani, et al., "Population and Diversity of Endophytic Bacteria Associated with Medicinal Plan Curumma zedoaria ", Microbiology Indonesia 8.2 (2014):4.

Bevivino, A., et al., "Characerization of free-living maize rhizosphere populatin of Burkholderia cepacia: effect of seed treatment on disease suppresssion and growth promotion of maize", FEMS Microbiology Ecology 27 (1998) 225-237.

Ciccillo, F., et al., Effects of two different application methods of Burkholderia ambifaria MCI 7 on plant growth and rhizospheric bacterial diversity.

Estrada, P., et al., "A N2-fixing endophytic *Burkholderia* sp. associated with maize plants culitvated in Mexico", Canadian Journal of Microbiology (2002), vol. 48(4), pp. 528-536.

Sharma, V.K., et al., "Enhancement of verticillium wilt resistance in tomato transplants by in vitro co-culture of seedlings with a plant growth promoting rhizobacterium (*Pseudomonas* sp. strain PsJN)", Canadian Journal of Microbiology (1998), vol. 44(6), pp. 285-294.

Grady, E., et al., "Current knowledge and perspectives of Paenibacillus: a review" Microb Cell Fact (2016) 15:203.

Li, J., et al., "Antitumour and antimicrobial activities of endophytic stretomycetes from pharmaceutical plants in rainforest", Lett Appl Microbiol. Dec. 2008; 47(6): 574-80. (Year: 2008).

Hamayun, M., et al., "Gibberellin production and plant growth promotion from pure cultures of *Cladosporium* sp. MH-6 isolated from cucumber (*Cucumis sativus* L.)", Mycologia, 102 (5), 2010, pp. 989-995.

Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.

Kim, S., et al., "Physiological and proteomic analyses of Korean F1 maize (*Zea mays* L.) hybrids under water-deficit stress during flowering", Appl. Biol. Chem. (2019) 62:32.

Halligan, B., et al., "Cloning of the murine cDNA encoding VDJP, a protein homologous to the large subunit of replication factor C and bacterial DNA ligases", Gene (1995) 217-222.

Arend, J., et al., "Hydroquinone: O-glucosytransferase from cultivated Rauvolfia cells: enrichment and partial amino acid sequences", Phytochemistry (2000) 53:187-193.

Enchev, R., et al., "Protein neddylation: beyond cullin-RING ligases", (Nature Reviews: Molecular Cell Biology (2015) 16:30-44.

Bais, H., et al., "The Role of Root Exudates in Rhizosphere Interactions with Plants and Other Organisms", Annual Review. Plant Biol. (2006) 57:233-266.

Goepfert, S., et al., "Molecular Identification and Characterization of the *Arabidopsis* D3,5, D2,4-Dienoyl-Coenzyme A Isomerase, a Peroxisomal Enzyme Participating in the b-Oxidation Cycle of Unsaturated Fatty Acids1", Plant Physiology (2005) 138:1947-1956.

Thomas, P., et al: "Endophytic Bacteria Associated with Growing Shoot Tips of Banana (*Musa* sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007 /S00248-009-9559-Z.

Database Geneseq [Online] Sep. 30, 2010 (Sep. 30, 2010), "Cellulomonas fermentans 16s rRNA gene SEQ ID:39.", retrieved from EBI accession No. GSN:AWL84299 Database accession No. AWL84299; & JP 2009 072168 A (Univ of Occupational & Environ) Apr. 9, 2009 (Apr. 9, 2009).

European Patent Office, Partial European Search Report, European Patent Application No. 20171870.7, dated Nov. 20. 2020, 18 Pages.

European Patent Office, European Search Report, European Patent Application No. 20171870.7, dated Mar. 1, 2021, 15 Pages.

GenBank Accession NR_041978, dated Aug. 8, 2011. (Year: 2011).

GenBank Accession AF394537, dated Jul. 2, 2002. (Year: 2002).

Andreolli, M., et al., "Endophytic Burkholderia fungorum DBT1 can improve phytoremediation efficiency of polycyclic aromatic hyrocarbons", Chemosphere, Pergamon Press, Oxford, GB, vol. 92, No. 6, May 21, 2013, pp. 688-694.

Extended European Search Report for EP 20202875.9, dated Apr. 19, 2021, 16 pages.

Douglas, G., et al., "PICRUSt2 for prediction of metagenome functions", Nature Biotechnology, vol. 38, No. 6, Jun. 1, 2020, pp. 685-688.

Kemp, N., et al., "Sarocladium zeae is a systemic endophyte of wheat and an effective biocontrol agent against Fusarium head blight", Biological Control, vol. 149, Publication No. 104329, 10 pages (2020).

Wicklow, D., et al., "A protective endophyte of maize: Acremonium zeae antibiotics inhibitory to Aspergillus flavus and Fasarium verticillioides", Mycol. Res. 109 (5):610-618 (May 2005).

Pan, J., et al., "Effects of host plant environment and Ustilago maydis infection on the fungal endophyte community of maize (*Zea mays*)", New Phytologist, vol. 178, pp. 147-156 (2008).

Wicklow, D., et al., "Occurrence of pyrrocidine and dihydroresorcylide production among Acremonium zeae populations from maize grown in different regions", Canadian Journal of Plant Pathology, vol. 30, pp. 425-433 (2008).

European Patent Office, Partial European Search Report, European Patent Application No. 18791606.9, dated Jul. 26, 2021, 16 Pages.

Abaid-Ullah, M., et al., "Plant Growth Promoting Rhizobacteria: An Alternate Way to Improve Yield and Quality of Wheat (*Triticum aestivum*)", International Journal of Agriculture and Biology, vol. 17, No. 1, Jan. 1, 2015, pp. 51-60.

Colla, G., et al., "Coating seeds with endophytic fungi enhances growth, nutrient uptake, yield and grain quality of winter wheat", International Journal of Plant Production, vol. 9, No. 2, Apr. 1, 2015, pp. 171-190.

Larran, S., et al., "Endophytes from wheat as biocontrol agents against tan spot disease", Biological Control, vol. 92, Sep. 11, 2015, pp. 17-23.

European Patent Office, Search Report, European Patent Application No. 17825317.5, dated Oct. 12, 2021, 9 Pages.

Yuan, J., et al., "Roots from distinct plant developmental stages are capable of rapidly selecting their own microbiome without the influence of environmental and soil edaphic factors", Soil Biology and Biochemistry 89 (2015): 206-209.

Frichot, E., et al., "Testing for Associations between loci and environmental gradients using latent factor mixed models", Mol. Biol. Evol. 30:7 1687-1699 (Year: 2013).

Bicego, M., et al., "Investigating Topic Models' Capabilities in Expression Microarray Data Classification", IEEE/transactions on computational biology and bioinformatics, 9:8 1831-1836 (Year: 2012).

(56) References Cited

OTHER PUBLICATIONS

Gerber, G., et al., "Inferring Dynamic Signatures of Microbes in Complex Host Ecosystems", PLOS Computational Biology 8:8 e1002624, 14 pages (Year: 2012).
Holmes, I., et al., "Dirichlet Multinomial Mixtures: Generative Models for Microbial Metagenomics", PLoSONE 7:2, e30126, 15 pages (Year: 2012).
Kim, Y., et al., "Deciphering the human microbiome using next-generation sequencing data and bioinformatics approaches", Methods 79-80, p. 52-59 (Year: 2015).
Anesi, A., et al., "Towards a scientific interpretation of the terrior concept: platicisity of the grape berry metabolome", BMP plant biology 15:191, 17 pages (Year: 2015).
Hill, S.T., The pursuit of hoppiness: propelling hop into the genomic era. Thesis, Oregon State University, 80 pages (Year: 2016).
Li, M., et al., "Persistent homology and the branching topologies of plants", American Journal of Botany, 104:3, 349-353 (Year: 2017).
Schuerger, A., "Microbial Ecology of a Crewed Rover Traverse in the Arctic: Low Microbial Dispersal and Implications for Planetary Protection on Human Mars Missions", Astrobiology, vol. 15, No. 6, 2015, pp. 478-491.
Timmusk, S., "Paenibacillus polymyxa antagonizes oomycete plant pathogens Phytophthora palmivora and Pythium aphanidermatum", Journal of Applied Microbiology, GB, vol. 105, No. 5, Jan. 5, 2009, pp. 1473-1481.
Fatima, Z., "Antifungal activity of plant growth-promoting rhizobacteria isolates against Rhizoctonia solani in wheat", African Journal of Biotechnology, vol. 8(2), pp. 219-225, Jan. 19, 2009, pp. 219-225.
GenBank Accession No. AY148074 published Nov. 30, 2002.
GenBank Accession No. FM998026 published Feb. 10, 2011.
GenBank Accession No. KJ494315 published May 3, 2014.
International Search Report and Written Opinion for PCT/US2022/026051, dated Oct. 28, 2022, 38 pages.
Langner Dos Santos Miriam et al: "Benefits Associated with the Interaction of Endophytic Bacteria and Plants", Brazilian Archives of Biology and Technology, vol. 61, No. 0, Jan. 1, 2018 (Jan. 1, 2018), pp. 18160431-2018.
Database GenBank [Online] NIH; Jan. 29, 2016 (Jan. 29, 2016), Wu JR: "Chitinophaga pinensis strain CSB3-50 16S ribosomal RNA gene", XP055948434, accession No. KU305719 Database accession No. KU305719.1 abstract.
Database Genbank [Online] NIH; Mar. 10, 2017 (Mar. 10, 2017), Shaffer JP et al: "Uncultured bacterium clone EHB-PS0362 16S ribosomal RNA gene", XP055948435, accession No. KU978322 Database accession No. KU978322.1 abstract.
Database GenBank [Online] NIH; Jan. 15, 2019 (Jan. 15, 2019), Hu C. J. et al: "*Chitinophaga* sp. strain N15203 16S ribosomal RNA gene", XP055948438, accession No. MK389338 Database accession No. MK389338.1 abstract.
Database Genbank [Online] NIH; Nov. 26, 2014 (Nov. 26, 2014), Han J. H. et al: "*Chitinophaga* sp. NR 1-07 16S ribosomal RNA gene", XP055948440, accession No. KM253104 Database accession No. KM253104.1 abstract.
Database Genbank [Online] NIH; Sep. 2, 2017 (Sep. 2, 2017), Jiayu T. J.: "*Chitinophaga* sp. strain PRd7 16S ribosomal RNA gene", XP055948441, accession No. KY203972 Database accession No. KY203972.1 abstract.
Database Genbank [Online] NIH; Oct. 1, 2010 (Oct. 1, 2010), Aslam Z. et al: "*Chitinophaga* sp. Z2-YC6856 16S ribosomal RNA gene", XP055948442, accession No. GQ369124 Database accession No. GQ369124.1 abstract.
Database Genbank [Online] NIH; Jun. 10, 2014 (Jun. 10, 2014), Zhang B. G.: "Chitinophaga oryziterrae strain ZBGKL4 16S ribosomal RNA gene", XP055948443, accession No. KJ734873 Database accession No. KJ734873.1 abstract.
Chung, E., et al: *Chitinophaga oryziterrae* sp. nov., isolated from the rhizosphere soil of rice (*Oryza sativa* L.) II, International Journal of Systematic and Evolutionary Microbiology, vol. 62, No. Pt_12, Dec. 1, 2012 (Dec. 1, 2012), pp. 3030-3035.

Proença Diogo Neves et al: "*Chitinophaga costaii* sp. nov., an endophyte of Pinus pinaster, and emended description of Chitinophaga niabensis", International Journal of Systematic and Evolutionary Microbiology, vol. 64, No. Pt_4, Apr. 1, 2014 (Apr. 1, 2014), pp. 1237-1243.
Elad, Y., et al: "Control of Rhizoctonia solani in cotton by seed-coating with *Trichoderma* spp. spores", Plant and Soil, vol. 66, No. 2, Jun. 1, 1982 (Jun. 1, 1982), pp. 279-281.
Harman, G.E., et al: "Trichoderma hamatum effects on seed and seedling disease induced in radish and pea by *Pythium* spp. or Rhizoctonia solani", Phytopathology, Dec. 1, 1980 (Dec. 1, 1980), pp. 1167-1172.
Harman, G.E., et al: "Factors affecting Trichoderma hamatum applied to seeds as a biocontrol agent", Phytopathology, Jun. 1, 1981 (Jun. 1, 1981), pp. 569-572.
Giczey, G., et al: "Homologous transformation of Trichoderma hamatum with an endochitinase encoding gene, resulting in increased levels of chitinase activity", FEMS Microbiology Letters, Jan. 1, 1998 (Jan. 1, 1998), pp. 247-252.
Freitas, R., et al: "Cloning and characterization of a protein elicitor Sml gene from Trichoderma harzianum", Biotechnology Letters, vol. 36, No. 4, Dec. 10, 2013 (Dec. 10, 2013), pp. 783-788.
Database Genbank [Online] NIH; Jan. 1, 2008 (Jan. 1, 2008), Hanada RE et al: "Trichoderma hamatum strain Dis 65G 18S ribosomal RNA gene, partial sequence; internal transcribed spacer 1", XP055973221, Database accession No. EU264000 abstract.
Database Genbank [Online] NIH; Sep. 6, 2013 (Sep. 6, 2013), Samuels G J et al: "Trichoderma hamatum strain Dis 240j actin (act) gene, partial eds", XP055973271, Database accession No. EU856256 abstract.
Database Genbank [Online] NIH; May 23, 2005 (May 23, 2005), Steyaert J M et al: "Trichoderma hamatum alkaline proteinase (prbl) gene, complete eds", XP055973243, Database accession No. AY258899 abstract.
Database Genbank [Online] NIH; Apr. 11, 2019 (Apr. 11, 2019), Chaverri P et al: "Trichoderma hamatum strain GJS 04-207 calmodulin (CAL) gene, partial eds", XP055973272, Database accession No. FJ442285 abstract.
Aerts A et al: "NCBI Reference Sequence: XP_024757499.1: glycoside hydrolase family 18 protein [Trichoderma asperellum CBS 433.97]", Apr. 26, 2018 (Apr. 26, 2018), pp. 1-2, XP055973177,.
Database Genbank [Online] NIH; Jul. 25, 2016 (Jul. 25, 2016), Steyaert J M et al: "Trichoderma hamatum endochitinase (chit42) gene, partial eds", XP055973252, Database accession No. AY258898 abstract.
Database Genbank [Online] NIH; Sep. 25, 1998 (Sep. 25, 1998), Giczey G et al: "endochitinase [*Trichoderma hamatum*]", XP055973364, Database accession No. AAC60385 abstract.
Database Genbank [Online] NIH; Sep. 25, 1998 (Sep. 25, 1998), Giczey G et al: "Trichoderma hamatum endochitinase gene, complete eds", XP055973251, Database accession No. U88560 abstract.
Liu, H.J., et al., "Bacillus subtilis strain A2-9 16S ribosomal RNA gene, partial sequence", Accession No. JF496331, deposited Aug. 2011.
Li, C., et al., "Bacillus subtilis strain B2-1 16S ribosomal RNA gene, partial sequence", Accession No. JN256114, deposited Sep. 2011.
Jiang, L., "Bacillus subtilis strain jllsy 16S ribosomal RNA gene, partial sequence", Accession No. FJ793201, deposited Apr. 2009.
Choi, N.S., et al., "Bacillus licheniformis strain DJ-2 16S ribosomal RNA gene, partial sequence", Accession No. FJ435676, deposited Jan. 2009.
Peng, S., et al., "Bacillus subtilis strain CCM9 16S ribosomal RNA gene, partial sequence", Accession No. HQ536000, deposited Dec. 2010.
Jee, H., et al., "Bacillus subtilis strain R2-1 16S ribosomal RNA gene, partial sequence", Accession No. EU852929, deposited Jul. 2009.
Zhao, Y., et al., "Bacillus amyloliquefaciens strain BGP14 16S ribosomal RNA gene, partial sequence", Accession No. JQ734536, deposited May 2012.

(56) References Cited

OTHER PUBLICATIONS

Allard, G. et al., "Spingo: a rapid species-classifier for microbial amplicon sequences," BMC Bioinformatics, 2015, vol. 16, No. 324, 8 pages.

Anders, S. et al., "Differential expression analysis for sequence count data," Genome Biology, 2010, vol. 11, No. 11, pp. R106.

Ansari, M.A.; Brownbridge, M.; Shah, F.A.; Butt, T.M. Efficacy of entomopathogenic fungi against soil-dwelling life stages of western flower thrips, Frankliniella occidentalis, in plant-growing media. Entomol. Exp. Appl. 2008, 127, 80-87.

Asaff, A.; Cerda-Garcia-Rojas, C.; De la Torre, M. Isolation of dipicolinic acid as an insecticidal toxin from Paecilomyces fumosoroseus. Appl. Microbiol. Biotechnol. 2005, 68, 542-547.

BB-CBI, "*Beauveria bassiana* (white muscardine fungus)," Invasive Species Compendium, 2021, pp. 1-68.

Beris, E.I.; Papachristos, D.P.; Fytrou, A.; Antonatos, S.A.; Kontodimas, D.C. Pathogenicity of three entomopathogenic fungi on pupae and adults of the Mediterranean fruit fly, *Ceratitis capitata* (Diptera: Tephritidae). J. Pest Sci. 2013, 86, 275-284.

Chen, F. et al., "Assessing Performance of Orthology Detection Strategies Applied to Eukaryotic Genomes," PLoS ONE, Apr. 2007, No. 4, pp. e383.

Cole, J.R. et al., "Ribosomal Database Project: data and tools for high throughput rRNA analysis," Nucleic Acids Research, 2014, vol. 42, pp. D633-D642.

Deshpande, V. et al., "Fungal identification using a Bayesian classifier and the Warcup training set of internal transcribed spacer sequences," Mycologia, 2016, vol. 108, No. 1, pp. 1-5.

Djian, C. et al., Acetic acid: A selective nematicidal metabolite from culture filtrates of *Paecilomyces lilacinus* (Thom) Samson and Trichoderma longibrachiatum Rifai. Nematologica 1991, 37, 101-112.

Doster, M.A. et al., "Biocontrol of Aflatoxins in Figs," Proceedings of the Third International Symposium on Fig, 798, 2008, pp. 223-226.

Eberhardt, C. et al., "Proteomic Analysis of Kveim Reagent Identifies Targets of Cellular Immunity in Sarcoidosis," PLOS One, Jan. 23, 2017, vol. 12, No. 1, pp. 1-16.

Edgar, R.C., "UNOISE2: Improved Error-Correction for Illumina 16S and ITS Amplicon Sequncing," BioRxiv, 2016, No. 081257, 21 pages.

Ehteshamul-Haque, S. et al., "Biological control of root rot diseases of okra, sunflower, soybean and mungbean," Pakistan Journal of Botany, vol. 22, No. 2, Jun. 1990, pp. 121-124.

Enright, A.J. et al., "An efficient algorithm for large-scale detection of protein families," Nucleic Acids Research, 2002, vol. 30, No. 7, pp. 1575-1584.

Enright, A.J. et al., "Protein families and Tribes in genome sequence space," Nucleic Acids Research, 2003, vol. 31, No. 15, pp. 4632-4638.

Combined printouts of term definitions from world wide web, performed by mkz Oct. 19, 2022 (Year. 2022).

Sarangi, S., et al., "Agricultural Activity Recognition with Smart-shirt and Crop Protocol", IEEE global humanitarian technology conference, p. 298-305 (Year: 2015).

Peiffer, J., et al., "The Genetic Architecture of Maize Height", Genetics, vol. 196, p. 1337-1356 (Year: 2015).

Kazemian, M., et al., "Improved accuracy of supervised CRM discovery with interpolated Markov models and cross-specieis comparison", Nucleic Acids Research, 2011, vol. 39, No. 22, 9463-9472.

Yeh, J.H., "Protein Remote Homology Detection Based on Latent Topic Vector Model", International conference on Networking and information technology, p. 456-460, (Year: 2010).

Heydari, A., "A Review on Biological Control of Fungal Plant Pathogens Using Microbial Antagonists", Journal of Biological Sciences, vol. 10 (4) 273-290 (Year: 2010).

Sessitsch, A., et al., "Functional Characteristics of an Endophyte Community Colonizing Rice Roots as Revealed by Metagenomic Analysis", MPMP vol. 25, No. 1, 2012, pp. 28-36.

Muhammad, N., et al., "Endophytes in biotechnology and agriculture", E-Cost FA1103 Working Group Meeting in Trento/S. Michele, Italy Nov. 2012. (poster).

Hurek, T., et al., "*Azoarcus* sp. strain BH72 as a model for nitrogen-fixing grass endophytes", Journal of Biotechnology 106 (2003) 169-178.

Engelhard, M., et al., "Preferential occurrence of diazotrophic endophytes, *Azoarcus* spp., in wild rice species and and races of *Oryza sativa* in comparison with moder races", Environmental Microbiology (2000) 2(2), 131-141.

Sessitsch, A., et al., "Endophytic bacterial communities of field-grown potato plants and their plant-growth-promoting and antagonistic abilities", Can. J. Microbiol. 50: 239-249 (2004).

Sessitsch, A., et al., "Cultivation-independent population analysis of bacterial endophytes in three potato varieties based on eubacterial and Actinomycetes-specific PCR of 16S rRNA genes", FEMS Microbiology Ecology 39 (2002) 23-32.

Minamisawa K., et al., "Anaerobic Nitrogen-Fixing Consortia Consisting of Clostridia Isolated from Gramineous Plants", Applied and Environmental Microbiology, May 2004, p. 3096-3102, vol. 70, No. 5.

Seghers, D., et al., "Impact of Agricultural Practices on the *Zea mays* L. Endophytic Community", Applied and Environmental Microbiology, Mar. 2004, p. 1475-1482, vol. 70, No. 3.

Bulgari, D., et al., "Endophytic Bacterial Diversity in Grapevine (*Vitis vinifera* L.) Leaves Described by 16S rRNA Gene Sequence Analysis and Length Beterogeneity-PCR", The Journal of Microbiology, Aug. 2009, p. 393-401, vol. 47, No. 4.

Amann, R., et al., "Single-cell identification in microbial communities by improved fluorescence in situ hybridization techniques", Nature Reviews Microbiology, 6: 339-348 (2008).

Chelius, M.K., et al., "The Diversity of Archaea and Bacteria in Association with the Roots of *Zea mays* L.", Microb Ecol (2001) 41:252-263.

Edwards, U., et al., "Isolation and direct complete nucleotide determination of entire genes. Characterization of a gene coding for 16S ribosomal RNA", Nucleic Acids Research 17: 7843-7853 (1989).

Prischl, M., et al., "Genetically modified Bt maize lines containing cry3Bb1, cry1A105 or cry1Ab2 do not affect the structure and functioning of root-associated endophyte communities", Applied Soil Ecology 54 (2012) 39-48.

Naveed, M., et al., "The endophyte *Enterobacter* sp. FD17: a maize growth enhancer selected based on rigorous testing of plant beneficial traits and colonization characteristics", Biol Fertil Soils (2014) 50:249-262.

Rashid, M., et al., "Inorganic polyphosphate is needed for swimming, swarming, and twitching motilities of Pseudomonas aeruginosa", PNAS vol. 97, No. 9, Apr. 25, 2000, pp. 4885-4890.

Mehta, S., et al., "An Efficient Method for Qualitative Screening of Phosphate-Solubilizing Bacteria", Current Microbiology vol. 43 (2001), pp. 51-56.

Dunn, R., et al., "Home Life: Factors Structuring the Bacterial Diversity Found within and between Homes", PLoS One, vol. 8, Issue 5, May 2013.

Massol-Deya, A., et al., "Bacterial community fingerprinting of amplified 16S and 16-23S ribosomal DNA gene sequences and restriction endonuclease analysis (ARDRA)", Molecular Microbial Ecology Manual 3.3.2: 1-8, 1995.

Extended European Search Report for Application No. 22190659,7, dated Feb. 10, 2023, 8 pages.

U'Ren, Jana M., et al.; "Community Analysis Reveals Close Affinities Between Endophytic and Endolichenic Fungi in Mosses and Lichens", Microbial Ecology, vol. 60, No. 2,Jul. 13, 2010, pp. 340-353.

Shah, S., et al: "Colonization with non-mycorrhizal culturable endophytic fungi enhances orchid growth and indole acetic acid production", BMC Microbiology, vol. 22, No. 1, Jan. 1, 2022, pp. 1-13.

Faria, M.; Wraight, S.P. Biological control of Bemisia tabaci with fungi. Crop Prot. 2001, 20, 767-778.

(56) References Cited

OTHER PUBLICATIONS

Friedman, J. et al., "Regularization Path for Generalized Linear Models via Coordinate Descent," Journal of Statistical Software, 2010, vol. 33, No. 1, pp. 1-22.

Hoy, M.A.; Singh, R.; Rogers, M.E. Evaluations of a novel isolate of Isaria fumosorosea for control of the Asian citrus psyllid, *Diaphorina citri* (Hemiptera: Psyllidae). Fla. Entomol. 2010, 93, 24-32.

Kepenekci, I. et al., "Pathogenicity of the Entomopathogenic Fungus, Purpureocillium Lilacinum TR1 Against the Black Cherry Aphid, *Myzus Cerasi Fabricus* (Hemiptera: Aphididae)," Mun. Ent. Zool., vol. 10, No. 1, Jan. 2015, pp. 53-60.

Koljalg. U. et al., "Towards a unified paradigm for sequence-based identification of fungi," Molecular Ecology, 2013, vol. 22, pp. 5271-5277.

Kozich, J.J. et al., "Development of a Dual-Index Sequencing Strategy and Curation Pipeline for Analyzing Amplicon Sequence Data on the MiSeq Illumina Sequencing Platform," Applied and Environmental Microbiology, Sep. 2013, vol. 79, No. 17, pp. 5112-5120.

Li, W. et al., "Ultrafast clustering algorithms for metagenomic sequence analysis," Briefings in Bioinformatics, Nov. 1, 2012, vol. 13, No. 6., pp. 656-668.

McMurdie, P.J. et al., "Waste Not, Want Not: Why Rarefying Microbiome Data Is Inadmissible," PLOS Computational Biology, 2014, vol. 10, No. 4, pp. e1003531.

Mezeal, I.A.; Mizil, S.N.; Hussin, M.S. Researching biocontrol of Trichoderma viride, Paecilomyces lilacinus in contradiction of effectiveness of fungi insulated as of selected therapeutic herbals. Plant Arch. 2018, 18, 1631-1637.

NCBI, "Purpureocillium lilacinum," Taxonomy ID: 33203, 2021, three pages, [Online] [Retrieved on Feb. 27, 2021] Retrieved from the Internet <URL: https://www.ncbi.nlm.nih.gov/Taxonomy/Browser/wwwtax.cgi?id=33203>.

Needleman, S.B. et al., "A General Method Applicable to the Search for Similarities in the Amino Acid Sequence of Two Proteins," Journal of Molecular Biology, 1970, vol. 28, No. 3, pp. 443-453.

O'Callaghan, M., "Microbial inoculation of seed for improved crop performance: issues and opportunities," Applied Microbiology and Biotechnology, vol. 100, May 2016, pp. 5729-5746.

Pandey, R. K. et al., "Effect of different bioformulations of Paecilomyces lilacinus against root-knot nematode (*Meloidogyne incognita*) infecting tomato (*Solanum esculentum*)," Indian Journal of Agricultural Sciences, vol. 81, No. 3, Mar. 2011, pp. 261-267.

Panyasiri, C.; Attathom, T.; Poehling, H.M. Pathogenicity of entomopathogenic fungi-potential candidates to control Insect pests on tomato under protected cultivation in Thailand. J. Plant Dis. Prot. 2007, 114, 278-287.

Paul, N.C.; Deng, J.X.; Lee, J.H.; Yu, S.H. New records of endophytic Paecilomyces inflatus and Bionectria ochroleuca from chili pepper plants in Korea. Mycobiology 2013, 41, 18-24.

Perveen, Z.; Shahzad, S.A. Comparative study of the efficacy of *Paecilomyces* species against root-knot nematode Meloidogyne incognita. Pak. J. Nematol. 2013, 31, 125-131.

Piatkowski, J.; Krzyzewska, U.; Nawrot, U. Antifungal activity of enthomopathogenic species of the genus Paecilomyces. Mikol. Lek. 2003, 10, 93-99 (with abstract).

Quast, C. et al., "The SILVA ribosomal RNA gene database project: improved data processing and web-based tools," Nucleic Acids Research, 2013, vol. 41, pp. D590-D596.

Raafat, I. et al., "*Nezara viridula* (Hemiptera: Pentatomidae) Cuticle as a Barrier for Beauveria bassiana and *Paecilomyces* sp. Infection," African Entomology, vol. 23, Iss. 1, Mar. 2015, pp. 75-87.

Rajinikanth, R. et al., "Management of nematode induced disease complex in seedlings of cauliflower (*Brsassica oleraceae* var. *botrytis*) using bio-pesticides," Pest Management in Horticultural Ecosystems, vol. 19, No. 2, Dec. 2013, pp. 203-210.

Ratnalikar, K.K. et al., "Biological management of root-rot of cotton caused by Rhizoctonia bataticola," Indian Phytopathol. 44-45, Suppl., XV, 1993, pp. 1-2.

Rideout, J.R. et al., "Subsampled open-reference clustering creates consistent, comprehensive OTU definitions and scales to billions of sequences," PeerJ, 2014, 2:e545.

Roth, A.C.J. et al., "Algorithm of OMA for large-scale orthology inference," BMC Bioinformatics, 2008, vol. 9, pp. 518.

Shenoy, B.D. et al., "Impact of DNA sequence-data on the taxonomy of anamorphic fungi," Fungal Diversity, 2007, vol. 26, No. 10, pp. 1-54.

Shibuya, H. et al., "Transformation of Cinchona Alkaloids into 1-N-Oxide Derivatives by Endophytic *Xylaria* sp. Isolated from Chinchona pubescens," Chem Pharm Bull, 2003, vol. 41, No. 1, pp. 71-74.

Singh, S. et al., "Bio-control activity of Purpureocillium lilacinum strains in managing root-knot disease of tomato caused by Meloidogyne incognita," Biocontrol Science and Technology, vol. 23, No. 12, Sep. 2013, pp. 1469-1489.

Sivakumar, T.; Eswaran, A.; Balabaskar, P. Bioefficacy of antagonists against for the management of *Fusarium oxysporum* f. sp. *lycopersici* and Meloidogyne incognita disease complex of tomato under field condition. Plant Arch. 2008, 8, 373-377 (with copy of abstract).

Smith, T.F. et al., "Identification of Common Molecular Subsequences," Journal of Molecular Biology, 1981, vol. 147, pp. 195-197.

Spurgeon, D.W., "Efficacy of Beauveria bassiana Against *Lygus hesperus* (Hemiptera: Miridae) at Low Temperatures," Journal of Entomological Science, vol. 45, Iss. 3, Jul. 2010, pp. 211-219.

Sword, G. A. et al., "Endophytic fungi alter sucking bug responses to cotton reproductive structures," Insect Science, vol. 24, Mar. 22, 2017, pp. 1003-1014.

Yeo, H.; Pell, J.K.; Alderson, P.G.; Clark, S.J.; Pye, B.J. Laboratory evaluation of temperature effects on the germination and growth of entomopathogenic fungi and on their pathogenicity to two aphid species. Pest Manag. Sci. 2003, 59, 156-165.

Zhang, X-Y. et al., "Diversity and Antimicrobial Activity of Culturable Fungi Isolated from Six Species of the South China Sea Gorgonians, " Microbial Ecology, vol. 64, Apr. 2012, pp. 617-627.

Zhou, W. et al., "A fungal endophyte defensive symbiosis affects plant-nematode interactions in cotton, " Plant Soil, vol. 422, Dec. 21, 2016, pp. 251-266.

Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.

Gaussian process model definition from towarddatascience.com downloaded May 15, 2023 (Year: 2023).

Gaussian process model definition from wikipedia.com, downloaded May 15, 2023 (Year: 2023).

Ghahramani, Z. (2013) Bayesian non-parametrics and the probabilistic approach to modeling. Philosophical transactions of the royal society A, vol. 371, 20110553, 20 pages.

Donahue, J. et al. Adversarial feature learning. arXiv: 1605.09782V7, Apr. 3, 2017.

Buee, et al. ("The rhizosphere zoo: an overview of plant-associated communities of microorganisms, including phages, bacteria, archaea, and fungi, and of some of their structuring factors." (2009): 189-212). (Year: 2009).

Hanapi, et al. ("Biofertilizer: Ingredients for Sustainable Agriculture." Biotechnology Development in Agriculture, Industry and Health: Current Industrial Application and Future Trends 1 (2012): 359-385). (Year: 2012).

Singh ("Screening and characterization of plant growth promoting rhizobacteria (PGPR): An overview." Bulletin of Environmental and Scientific Research 4.1-2 (2015): 1-2). (Year: 2016).

Database accession No. JQ759107, European Nucleotide Archive [Online] EMBL's European Bioinformatics Institute; Mar. 7, 2012, U'ren J M et al: "*Sordariomycetes* sp.genotype 60 isolate AK0688 internal transcribed spacer."

Database accession No. MG917011, European Nucleotide Archive [Online] EMBL's European Bioinformatics Institute; Feb. 21, 2019, Lagarde A. et al: "*Coniochaeta* sp.isolate Gir_07 internal transcribed spacer 1, partial sequence."

(56) References Cited

OTHER PUBLICATIONS

Database accession Nos. MZ267873, MZ267979, MZ267926, MZ267820; European Nucleotide Archive [Online] EMBL's European Bioinformatics Institute; Sep. 11, 2021, Arnold AE: "Coniochaeta nivea isolate LG0013 various submissions.".

Database accession Nos. MZ267874, MZ267980, MZ267927, MZ267821; European Nucleotide Archive [Online] EMBL's European Bioinformatics Institute; Sep. 11, 2021, Arnold AE: "Coniochaeta nivea isolate LG0023."

Kokaew, J. et al; "Coniochaeta ligniaria an endophytic fungus from Baeckea frutescens and its antagonistic effects against plant pathogenic fungi", Thai Journal of Agricultural Science, vol. 44, Jun. 1, 2011, pp. 123-131.

Lagarde A. et al: "Antiproliferative and antibiofilm potentials of endolichenic fungi associated with the lichen Nephroma laevigatum", Journal of Applied Microbiology, vol. 126, No. 4, Jan. 30, 2019, pp. 1044-1058.

Nilsson et al; "Correspondence: Intraspecific ITS Variability in the Kingdom Fungi as Expressed in the International Sequence Databases and Its Implications for Molecular Species Identification", Evolutionary Bioinformatics, Jan. 1, 2008, pp. 193-201.

Trifonova, R. et al; "Interactions of plant-beneficial bacteria with the ascomycete Coniochaeta ligniaria", Journal of Applied Microbiology, vol. 106, No. 6, Jun. 1, 2009, pp. 1859-1866.

Wang, B., et al., "Fungal endophytes of native *Gossypium* species in Australia," Mycological Research, 2007, pp. 347-354, vol. 111, No. 3.

Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.

Wang, Q., el al., "Naive Bayesian Classifier for Rapid Assignment of rRNA Sequences into the New Bacterial Taxonomy," Appl. Environ Microbiol., 2007, pp. 5261-5257, vol. 73, No. 16.

Waqas, M., el al., "Endophytic Fungi Produce Gibberellins and Indoleacetic Acid and Promotes Host-Plant Growth during Stress," Molecules, 2012, pp. 10754-10773, vol. 17.

Weaver, P.F., et al., "Characterization of Rhodopseudomonas capsulata," Arch Microbiol., 1975, pp. 207-216, vol. 105.

Weindling, R., "Relation of dosage to control of cotton seedling diseases by seed treatment," Plant Disease Reporter, 1943, 27, pp. 68-70.

Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.

Whelehan, et al., "Microenupsulalion using vibrating technology," Journal of Microencapsulation 2011, vol. 28(8), pp. 669-688.

White, J. F., et al., "A Proposed Mechanism for Nitrogen Acquisition by Grass Seedlings Through Oxidation of Symbiotic Bacteria," Symbiosis, 2012, pp. 161-171, vol. 57.

Marquez, L. M., et al., "A Virus in a Fungus in a Planl: Three-Way Symbiosis Required for Thermal Tolerance," Science, 2007, pp. 513-515, vol. 315.

Mastretta, C., et al., "Endophytic Bacteria from Seeds of Nicotiana Tabacum Can Reduce Cadmium Phytotoxicity," Intl J Phytoremediation, 2009, pp. 251-267, vol. 11.

Mateos, P. F., et al., "Cell-Associated Pectinolytic and Cellulolytic Enzymes in Rhizobium leguminosarum biovartrifolii," Appl Environ Microbiol., 1992, pp. 816-1822, vol. 58, No. 6.

McDonald, D., et al., "An Improved Greengenes Taxonomy with Explicit Ranks for Ecological and Evolutionary Analyses of Bacteria and Archaea," ISME J., 2012, pp. 610-618, vol. 6.

McGuire, K.L., et al., "Digging the New York City Skyline: Soil Fungal Communities in Green Roofs and City Parks," PLoS One, 2013, vol. 8, No. 3, 13 Pages.

Medina, P., el al., "Rapid Identification of Gelatin and Casein Hydrolysis Using TCA," J Microbiol Melhods, 2007, pp. 391-393, vol. 69.

Mehnaz, S., el al., "Growth Promoting Effects of Corn (*Zea mays*) Bacterial Isolates Under Greenhouse and Field Conditions," Soil Biology and Biochemistry, 2010, pp. 1848-1856, vol. 42.

Mehnaz, S., et al., "Isolation and 16S rRNA sequence analysis of the beneficial bacteria from the rhizosphere of rice," Canada Journal of Microbiology, 2001, pp. 110-117, vol. 47, No. 2.

Mei, C., et al., "The Use of Beneficial Microbial Endophytes for Plant Biomass and Stress Tolerance Improvement," Recent Patents on Biotechnology, 2010, pp. 81-95, vol. 4.

Michel, B. E., et al., "The Osmotic Potential of Polyethylene Glycol 6000," Plant Physiol., 1973, pp. 914-916, vol. 51.

Misk, A., et al., "Biocontrol of chickpea root rot using endophytic actinobacteria", Biocontrol. vol. 56, No. 5, Mar. 12, 2011, pp. 811-822, XP036215297.

Miyoshi-Akiyama, T., et al., "Multilocus Sequence Typing (MLST) for Characterization of Enterobacter cloacae." PLoS ONE, 2013, vol. 8, No. 6, 10 Pages, e66358.

Moe, L. A., "Amino Acids in the Rhizosphere: From Plants to Microbes," American Journal of Botany, 2013, pp. 1692-1705, vol. 100, No. 9.

Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.

Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.

Mundt, J.O., et al., "Bacteria Within Ovules and Seeds," Appl Environ Microbiol., 1976, pp. 694-698, vol. 32, No. 5.

Murali, Gopal, et al., "Microbiome Selection Could Spur Next-Generation Plant Breeding Strategies," Frontiers in Microbiology, vol. 7, Dec. 7, 2016, XP055531064.

Naik, B. S., et al., "Study on the diversity of endophytic communities from rice (*Oryza sativa* L.) and their antagonistic activities in vitro," Microbiological Research, 2009, pp. 290-296, vol. 164.

Nassar, A., et al., "Promotion of plant growth by an auxin-producing isolate of the yeast Williopsis satumus endophytic in maize (*Zea mays* L.) roots", Biology and Fertility of Soils; Cooperatlng Journal of International Society of Soil Science, Springer, Berlin, DE, vol. 42, No. 2, Nov. 1, 2005, pp. 97-108.

Naveed, M., "Maize Endophytes—Diversity, Functionality and Application Potential," University of Natural Resources and Life Sciences, 2013, pp. 1-266 and 81-87; Tables 1-3; Figure 2.

NCBI GenBank: Accession No. JX880250.1, "Enterobacteriaceae bacterium Clero1 16S ribosomal RNA gene, partial equence," NIH, June 24, 2015, 2 Pages, can be retrieved at <URL:https://www.ncbi.nlm.nih.gov/nucleotidelJX880250.1?report=genbank&log$=nuclalign&blast_rank=80 &RID=KWUPBV08015>.

NCBI GenBank: Accession No. XP55670271, "*Enlerobacter* sp. MLBOS 16S ribosomal RNA gene, partial sequence—Nucleotide", Jun. 9, 2012, 1 Page, can be retreived at URL:https://www.ncbi.nlm.nih.gov/nuccore/J Q765415.1/.

NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/K C355340.

NCBI GenBank: Accession No. XP55670279, "Uncultured bacterium clone bb2s4 16S ribosomal RNA gene, partial seque—Nucleotide", May 6, 2005, 1 Page, can be retreived at URL:https://www.ncbi.nlm.nih.gov/nuccore/D Q068880.

NCBI GenBank: CP000653.1 "*Enterobacter* sp. 638, complete genome" ASM1532v1, Apr. 18, 2007, 2 Pages, Can be retrieved at <URL:https://www.ncbi.nlm.nih.gov/assembly/GCA 000016325.1 >.

NCBI GenBank: CP000653.1 "*Enterobacter* sp. 638, complete genome" Jan. 28, 2014, 5 Pages, Can be retrieved at<URL:https://www.ncbi.nlm.nih.gov/nucoore/CP000653.1>.

NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.

NCBI GenBank: EBI accession No. EM STD:JQ759988, "*Dothideomyceles* sp. genotype 226 isolate FL0175 internal tran-

(56) References Cited

OTHER PUBLICATIONS scribed spacer 1, partial sequence; 5.8S ribosomal RNA gene and internal transcribed spacer 2, complete sequence; and 28S ribosomal RNA gene, partial sequence," May 17, 2012, 2 Pages.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI, GenBankAccession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at<URL:https://www.ncbi.nlm.nih.gov/nuccore/KX641980>.
NCBI, GenBankAccession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Nejad, P. et al., "Endophytic Bacteria Induce Growth Promotion and Wilt Disease Suppression in Oilseed Rape and Tomato," Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., el al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin max*) wtth Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima. K.A., et al., "Demonstrating Pathogenicity of Enterobacter cloacae on Macadamia and Identifying Associated Volatiles of Gray Kernel of Macadamia in Hawaii," Plant Disease, Oct. 2007. vol. 91, No. 10, pp. 1221-1228.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
O'Hanlon, K., et al., "Exploring the potential of symbiotic fungal endophytec in cereal disease suppression", Biological Control, vol. 63, No. 2, Sep. 5, 2012, pp. 69-78.
Ogbo, F., et al., "Some Characteristics of a Plant Growth Promoting; iEnterobacter/isp. Isolated from the Roots of Maize", Advances in Microbiology, Jan. 1, 2012, vol. 02, No. 03, pp. 368-374.
Okunishi, S., et al., "Bacterial Flora of Endophytes in the Maturing Seeds of Cultivated Rice (*Oryza saliva*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Orakçi GE et al, "Selection of antagonistic actinomycete isolates as biocontrol agents against root-rot fungi", Fresenius Environmental Bulletin, 2010, 19: 417-424 & GenBank Accession Number GQ475299, Oct. 5, 2009.
Orole, O. O., et al., "Bacterial and fungal endophytes associated with grains and roots of maize," Journal of Ecology and the Natural Environment, 2011, pp. 296-303, vol. 3, No. 9.
Pacovsky, R., "Carbohydrate, protein and amino acid status of Glycine-Glomus-Bradyrhizobium symbioses," Physiologia Pantarium; 75:346-354, 1989).
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
Partida-Martinez, L.P., et al., "The Microbe-Free Plant: Fact or Artifact?" Front Plant Sci., 2011, vol. 2, No. 100, 16 Pages.
PCT International Preliminary Report on Patentability, PCT Application No. PCT/US2016/030292, dated Aug. 2, 2017, 23 Pages.
PCT International Search Report and Wlitten Opinion, PCT Application No. PCT/US2015/068206, dated Jun. 27, 2016, 20 Pages.
PCT International Search Report and Wlitten Opinion, PCT Application No. PCT/US2016/036504, dated Nov. 4, 2016, 18 Pages.
PCT International Search Report and Written Opinion for PCT/AU2018/050387, dated Jul. 12, 2018, 8 pages.
Clark, E. M., et al., "Improved Histochemical Techniques for the Detection of Acremonium coenophilum in Tall Fescue and Methods of in vitro Culture of the Fungus," J Microbiol Methods, 1983, pp. 149-155, vol. 1.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Clay, K., "Effects of fungal endophyles on the seed and seedling biology of Lolium perenne and Festuca arundinacea," Oecologia, 1987, pp. 358-362, vol. 73.
Clough, S. J., et al., "Floral Dip: A Simplified Method for Agrobacterium-mediated Transformation of *Arabidopsis thaliana*," Plant J., 1998, pp. 735-743, vol. 16, No. 6.
Compant, S., et al., "Endophytes of Grapevine: Flowers, Berries, and Seeds: Identification of Cultivable Bacteria, Comparison with Other Plant Parts, and Visualization of Niches of Colonization," Microbial Ecology, 2011, pp. 188-197, vol. 62.
Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.
Conn, V. M., "Effect of Microbial Inoculants on the Indigenous Actinobacterial Endophyte Population in the Roots of Wheats as Determined by Tenninal Restriction Fragment Length Polymorphism," Applied and Environmental Microbiology, 2004, pp. 6407-6413, vol. 70, No. 11.
Coombs, J. T., et al., "Isolation and Identification of Actinobacteria from Surface-Sterilized Wheat Roots," Applied and Environmental Microbiolog,, 2003, pp. 5603-5608, vol. 69, No. 9.
Cottyn, B., et al., "Phenotypic and genetic diversity of rice seed-associated bacteria and their role in pathogenicity and biological control," Journal of Applied Microbiology, 2009, pp. 885-897, vol. 107.
Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycin max* (L) Merril) Against Challenge Inoculation with R. solani," Journal of Applied Science and Research, 2014, pp. 70-84, vol. 2, No. 5.
Danhorn, T., et al., "Biofilm Formation by Plant-Associated Bacteria," Annu Rev Microbiol. 2007, pp. 401-422, vol. 61.
Daniels, R., et al., "Quorum Signal Molecules as Biosurfactants Affecting Swarming in Rhizobium etli," PNAS, 2006, pp. 14965-14970, vol. 103, No. 40.
Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Environmental Microbiology, 2008, pp. 2669-2678, vol. 74, No. 9.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession; No. AY016368 sequence.
Database Geneseq Database accession No. BAP97938 "Pantoea dispersa strain KACC91642P 16S rDNA sequence, SEQ ID 1." Aug. 15, 2013, 1 Page.
DBGET, "Orthology: K14454," 2005, 2 pages, can be retrieved at <URL:http://www.genome.jp/dbget-bin/www.bget?ko:K14454>.
De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.

(56) References Cited

OTHER PUBLICATIONS

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

De Medeiros, L., et al., "Evaluation of Herbicidal Potential of Depsides from Cladosporium uredinicola an Endophytic Fungus found in Guava Fruit," J. Braz. Chem Soc., 2012, vol. 23, No. 8, p. 1551-1557.

De Melo Pereira, G. V., et al. "A Multlphasic Approach for the Identification of Endophytic Bacterial in Strawberry Fruit and their Potential for Plant Growth Promotion," Microb. Ecology, 2012, pp. 405-417, vol. 63, No. 2.

De Santi, M. et al., "A combined morphologic and molecular approach for characterizing fungal microflora from a traditional Italian cheese (*Fossa cheese*)," Inter. Dairy J., 2010, vol. 10, No. 7, pp. 465-471.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichodenna," Trans Brit Mycol Soc, 1971, pp. 25-39, vol. 57, No. 1.

Desiro, A., et al., "Detection of a novel intracellular microbiome hosted in arbuscular mycorrhizal fungi," ISME Journal, 2014, pp. 257-270, vol. 8.

Djordjevic, D., et al., "Microtiter Plate Assay for Assessment of Listeria monocylogenes Biofilm Formation," Annl Environ Microbiol, 2002, pp. 2950-2958, vol. 68, No. 6.

Don, R.H., et al., "Properties of Six Pesticide Degradation Plasmids Isolated From Alcaligenes Paradoxus and Alcaligenes eutrophus," J Bacteriol., 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 2 Pages.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than Blast," Bioinformatics, 2010, pp. 2460-2461, vol. 26, No. 19.

Edgar, R. C., "Uparse: Highly Accurate OTU Sequences From Microbial Amplicon Reads," Nat. Methods, 2013, pp. 996-998, vol. 10, No. 10.

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.

Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.

Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.

El-Shanshoury, A. R., "Growth Promotion of Wheat Seedlings by Streptomyces atroolivaceus," Journal of Agronomy and Crop Science, 1989, pp. 109-114, vol. 163.

Emerson, D., et al., "Identifying and Characterizing Bacteria in an Era of Genomics and Proleomics." BioScience, 2008, pp. 925-936, vol. 58, No. 10.

Endre, G., et al., "A Receptor Kinase Gene Regulating Symbiotic Nodule Development," Nature, 2002, pp. 962-966, vol. 417.

European Patent Office, Communication Pursuant to Article 94(3) EPC for European Patent Application No. 13874703.5, dated Jan. 5, 2018, 4 Pages.

European Patent Office, Communication Pursuant to Article 94(3) EPC for European Patent Application No. 15810847.2, dated Nov. 17, 2017, 17 Pages.

European Patent Office, Communication Pursuant to Article 94(3) EPC for European Patent Application No. 14748326.7, dated Feb. 15, 2018, 7 Pages.

European Patent Office, Communication Pursuant to Article 94(3) EPC for European Patent Application No. 14777213.1, dated Jun. 18, 2018, 4 Pages.

European Patent Office, Examination Report for European Patent Application No. EP 14777213.1, dated Oct. 20, 2017, 12 Pages.

European Patent Office, Examination Report, European Patent Application No. 14748326.7, dated Jul. 19, 2017, 4 Pages.

European Patent Office, Extended European Search Report, European Patent Application No. EP 15809264.3, dated Mar. 12, 2018, 14 Pages.

European Patent Office, Extended European Search Report, European Patent Application No. EP 15812324.0, dated Feb. 21, 2018, 23 Pages.

European Paten Office, Extended European Search Report, European Patent Application No. EP 15876324.3, dated Jun. 12, 2018, 9 Pages.

European Paten Office, Supplementary European Search Report for European Patent Application No. 15810847.2, dated Feb. 28, 2018, 19 Pages.

European Paten Office, Supplementary European Search Report, European Patent Application No. EP 13874703.5, dated Jun. 21, 2016, 3 Pages.

"Sequence Alignment of JQ047949 with Instant SEQ ID No. 2," Search conducted on Jan. 2, 2019, 2 pages.

Abarenkov, K., et al., "PlutoF-A Web Based Workbench for Ecological and Taxonomic Research, with an Online Implementation for Fungal ITS Sequences," Evol Bioinform Online, 2010, pp. 189-196. vol. 6.

Abarenkov, K., et al., "The Unite Database for Molecular Identification of Fungi—Recent Updates and Future Perspectives," New Phvtol., 2010, pp. 281-285, vol. 186.

Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.

Abdellatif, L., et al., "Endophytic hyphal companmentalizalion is required for successful symbiotic Ascomycota association with root cells," Mycological Research, 2009, pp. 782-791, vol. 113.

Abdou, R., et al., "Botryorhodines A-D, antifungal and cytotoxic depsidones from Botryosphaeria rhodina, an endophyte of the medicinal plant Bidens pilosa," Phytochemistry, 2010, vol. 71, pp. 110-116.

Abou-Shanab, R.A., et al: "Characterization of Ni-resistant bacteria in the rhizosphere of the hyperaccumulalor Alyssum murale by 16S rRNA gene sequence analysis", World Journal of Microbiology and Biotechnology, vol. 26, No. 1, Aug. 15, 2009, pp. 101-108.

Adhikari, M., el al., "A New Record of Pseudeurotium bakeri from Crop Field Soil in Korea," The Korean Journal of Mycology, 2016, pp. 145-149, vol. 44.

Ahmad, F., et al., "Screening of Free-Living Rhizospheric Bacteria for Their Multiple Plant Growth Promotinq Activities," Microbiol Res., 2008, pp. 173-181, vol. 163.

Al-Askar AA, "Microbiological studies on the in vitro inhibitory effecl of Streptomyces collinus albescens against some phytopathogenic fungi", African Journal of Microbiology Research, 2012, 6: 3277-3283 & GenBank Accession No. AB184101, May 20, 2008.

Alvarez-Perez, S., et al., "Zooming-in on floral nectar: a first exploration of nectar-associated bacteria in wild plant communities," FEMS Microbiol. Ecol, 2012, vol. 80, No. 3, pp. 591-602.

Amann, R., et al., "The Identification of Microorganisms by Fluorescence in Situ Hybridisation," Curr Opin Biotechnol., 2001, pp. 231-236, vol. 12.

Amatuzzi, R.F., et al., "Potential of endophylic fungi as biocontrol agents of *Duponchelia fovealis* (Zeller) Lepidoptera:Crambidae," Brazilian Journal of Biology, Nov. 9, 2017, 7 Pages.

Amatuzzi, R.F., et al., "Universidade Federal Do Parana," Jan. 1, 2014, 52 Pages. (With English Abstract).

Antony-Badu, S., et al., "Multiple *Streptomyces* species with distinct secondary metabolomes have identical 16S rRNA gene sequences." Scientific Reports 7.1, Sep. 2017, No. 7, 11089, pp. 1-8.

Apel, K., et al., "Reactive Oxygen Species: Metabolism, Oxidative Stress, and Signal Transduction," Annu Rev Plant Biol., 2004, pp. 373-399, vol. 55.

(56) References Cited

OTHER PUBLICATIONS

Ardakani, M.R. et al., "Absorption of N, P, K thorugh triple inoculation of wheat (*Triticum aestivum* L.) by *Azospirillum brasilense, Streptomyces* sp., Glomus intraradicee and manure application," Physiol Mol Biol Plants, 2011, vol. 17, No. 2, pp. 181-192.

Arendt, K. R., et al., "Isolation of endohyphal bacteria from foliar Ascomycota and in vitro establishment of their symbiolic associations," Appl. Environ. Microbiol., 2016, pp. 2943-2949, vol. 82, No. 10.

Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.

Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.

Aveskamp, M., et al., "DNA phylogeny reveals polyphyly of Phoma section Peyronellaea and multiple taxonomic novelties," Mycologia, 2009, vol. 101, No. 3, pp. 363-382.

Azcon, R., et al., "Selective interactions between different species of mycorrhizal fungi and Rhizobium meliloti strains, and their effects on growth, N2-fixation (15N) and nutrition of *Medicago sativa* L.," New Phytol., 1991, vol. 117, pp. 399-404.

Bacon, C. W, et al., "Isolation, In Planta Detection, and Uses of Endophytic Bacteria for Plant Protection," Manual of nvironmenlal Microbiology, 2007, pp. 638-647.

Baker, K. F., et al., "Dynamics of Seed Transmission of Plant Pathogens," Annu Rev. Phytopathol., 1966, pp. 311-334, vol. 4.

Baltruschat, H., el al., "Salt tolerance of baney induced by the root endophyte Piriformospora indica is associated with a strong increase in antioxidants," New Phytologist., 2008, pp. 501-510, vol. 180.

Bandara, WM.M.S., et al., "Interactions among endophytic bacteria and fungi: effects and potentials" Journal of Biosciences, Dec. 2006, vol. 31, No. 5, pp. 645-650.

Barnett, S., et al., "Seleclion of microbes for control of Rhizoctonia root rot on wheat using a high throughput pathosyslem", Biological Control, Jul. 6, 2017, 113: 45-57.

Bashan, Yoav E., et al., "Alginate Beads as Synthetic Inoculant Carriers for Slow Release of Bacteria that Affect Plant Growth," Applied and Environmental Microbiology, pp. 1089-1098, May 1986.

Bashan, Yoav Ed, et al., "Inoculants of plant growth-promoting bacteria for use in agriculture," Biotechnology Advances, Elsevier Publishing, Balking, GB, vol. 16, No. 4, Jul. 1, 1998, pp. 729-770, XP004123985.

Bensch, K., et al., "Species and ecological diversity within the Cladosporium cladosporioides complex (Davidiellaceae, Capnodiales)," Studies in Mycology, 2010, pp. 1-94, vol. 67.

Bentley, S.D., et al, Complete genome sequence of the model actinomycete Streptomyces coelicolor A3(2), Nature. May 9, 2002;417(6885):141-7. (Year: 2002).

Bethlenfalvay, G., et al., "Mycorrhizal fungi effects on nutrient composition and yield of soybean seeds", Journal of Plant Nutrition, vol. 20, pp. 4-5, Apr. 1, 1997, pp. 581-591.

Bing, LA, et al., "Suppression of *Ostrinia nubilalis* (Hübner) (Lepidoptera: Pyralidae) by endophytic *Beauveria bassiana* (Balsamo) Vuillemin", Environmental Entomol, Entomological Society of America, College Park, MD, US, vol. 20, Jan. 1, 1991, pp. 1207-1211.

Block, C. C., et al., "Seed Transmission of Pantoea stewartii in Field and Sweet Corn," Plant Disease, 1998, pp. 775-780, vol. 82.

Bragantia, et al, "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).

Brinkmeyer, R., et al., "Uncuitured Bacterium Clone ARKMP-100 16S Ribosomal RNA Gene, Partial Sequence," NCBI GenBank Accession No. AF468334, Submitted Jan. 14, 2002.

Brodie, E.L., et al., "Uncultured Bacterium Clone BANW722 16S Ribosomal RNA Gene, Partial Sequence," NCBI GenBank Accession No. DQ264636, Submitted Oct. 25, 2005, 1 Page.

Bulgarelli, D., et al., "Structure and Functions of the Bacterial Microbiola of Plants," Annu Rev Plant Biol., 2013, pp. 807-838, vol. 64.

Büttner, D., et al., "Regulation and secretion of Xanthomonas virulence factors," FEMS Microbiology Reviews, 2010, pp. 107-133, vol. 34, No. 2.

Caporaso, J.G.. et al., "Ultra-High-Throughput Microbiol Community Analysis on the Illumina HiSeq and MiSeq Platforms," ISME J., 2012, pp. 1621-1624, vol. 6.

Castillo, D., et al., "Fungal Endophytes: Plant Protective Agents Against Herbivores," Power Point Presentation dated Aug. 4, 2013.

Castillo, D., et al., "Fungal Entomopathogenic Endophytec: Negative Effects on Cotton Aphid Reproduction in Greenhouse and Field Conditions," Power Point Presentation dated Mar. 23, 2013, 21 Pages.

Cavalier-Smith, T., "A Revised Six-Kingdom System of Life," Biol Rev Camb Philos Soc., 1998, pp. 203-266, vol. 73.

Cha, C., et al., "Production of Acyl-Homoserine Lactone Quorum-Sensing Signals by Gram-Negative Plant Associated Bacteria," Mol Plant Microbe Inleract.,1998, pp. 1119-1129, vol. 11, No. 11.

Chagas, F., et al., "A Mixed Culture of Endophytic Fungi Increases Production of Antifungal Polyketides," J. Chem Ecol., Oct. 2013, pp. 1335-1342, vol. 39.

Chaves, J., et al., "Identification and Phylogeny of Streptomyces Based on Gene Sequences", Research Journal of Microbiology, vol. 13, No. 1, Dec. 15, 2017, pp. 13-20, XP055675917.

Chenhua Li , et al., "Change in deep soil microbial communities due to long-term fertilization." Soil Biology and Biochemislry, vol. 75, Mar. 5, 2014, pp. 264-272, XP055530941.

Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 4(9):3214-3222.

Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.

European Patent Office, Supplementary European Search Report, European Patent Application No. 13874703.5, dated Oct. 21, 2016, 16 Pages.

European Patent Office, Supplementary European Search Report, European Patent Application No. 14860187.5, dated May 24, 2017, 9 Pages.

European Patent Office, Supplementary European Search Report, European Patent Application No. 14874589.6, dated Jul. 11, 2017, 9 Pages.

European Patent Office, Supplementary European Search Report, European Patent Application No. ep 15809264.3, dated Dec. 4, 2017, 16 Pages.

European Patent Office, Supplementary European Search Report, European Patent Application No. EP 15812324.0, dated Nov. 2, 2017, 19 Pages.

European Patent Office, Supplementary Partial European Search Report, European Patent Application No. 13874703.5, dated Jun. 21, 2016, 3 Pages.

Faria, D. C., et al., "Endophyllc Bacteria Isolated from Orchid and Their Potential to Promote Plant Growth," World Microbiol Biotechnol., 2013, pp. 217-221, vol. 29.

Fatima Z et al, "Antifungal activity of plant growth-promoting rhizobacteria isolates against Rhizoctonia solani in wheat", African Journal of Biotechnology, 2009, 8: 219-225.

Ferrando, L., et al., "Molecular and Culture-Dependent Analyses Revealed Similarities in the Endophytic Bacterial Community Composition of Leaves from Three Rice (*Oryza saliva*) Varieties," FEMS Microbiol Ecol., 2012, pp. 696-708, vol. 80.

Fiehn, O., et al., "Metabolite Profiling for Plant Functional Genomics," Nature Biotechnol., 2000, pp. 1157-1161. vol. 8.

Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.

Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.

(56) References Cited

OTHER PUBLICATIONS

Fisher, P. J., et al., "Fungal saprobes and pathogens as endophytes of rice (*Oryza sativa* L.)," New Phytol., 1992, pp. 137-143, vol. 120.
Fisher, P.R., et al., "Isolation and Characterization of the Pesticide-Degrading Plasmid pJP1 from Alcaligenes paradoxus," J Bacteriol., 1978, pp. 798-804, vol. 135, No. 3.
Fox, G., et al., "How close is close: 16S rRNA sequence identity may not be sufficient to guarantee species identity." International Journal of Systematic and Evolutionary Microbiology 42.1, 1992, pp. 166-170.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common,"ISME J., 2008, pp. 901-910, vol. 2.
Gabor, J., et al., "Mycorrhizal fungi effects on nutrient composition and yield of soybean seeds," Journal of Plant Nutrition, 20:4-5, 581-591, 1997.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitalion of Major Human Cutaneous Bacterial and Fungal Populations," J Clin Microbiol, 2010, pp. 3575-3581, vol. 48, No. 10.
Carazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007, 1 Page.
Gebhardt, J., et al., "Characterization of a single soybean cDNA encoding cytosollc and glyoxysomal isozymes of aspartate aminostransferase," Plant Molecular Biology, 1998, pp. 99-108, vol 37.
GenBank Accession No. KF951483, Jan. 5, 2014.
GenBank Accession No. KJ152029, May 6, 2015.
GenBank Accession No. KJ162248, Apr. 8, 2014.
GenBank Accession No. KY643705, Feb. 27, 2017.
GenBank: AF034210.1 "Glycine max aspartate aminotransferase glyoxysomal isozyme AAT1 precursor and aspartate aminotransferase cytosolic isozyme AAT2 (AAT) mRNA, complete eds," NCBI, May 26, 1998, 2 Pages, can be retrieved at <URL:https://www.ncbi.nlm.nih.gov/nucoore/AF034210>.
GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
GenBank: NP_001237541.1, "aspartate aminotransferase glyoxysomal isozyme AAT1 precursor [Glycine max]," NCBI, Oct. 29, 2016, 2 Pages, can be retrieved at <URL:https//ww.ncbi.nlm.nih.gov/protein/NP_001237541.1 >.
GenEmbl database, GenEmbl Record No. EU 977189, Jan. 21, 2009, 4 pages, Smith, S.A., et al., "Bioactive endophytes warrant intensified exploration and conservation," PloS ONE 3(8):E3052, 2008.
GenEmbl Database, GenEmbl Record No. JN872548.1, 2 Pages, 2012.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
GenEmbl Database, GenEmbl Record No. KF673660, Sandberg, et al., "Fungal endophytec of aquatic macrophytes: diverse host-generalists characterized by tissue preferences and geographic structure," 2013, 35 Pages.

GenEmbl Database, GenEmbl Record No. KP991588, Huang, et al., "Pervasive effects of wildfire on foliar endophyte communities in montane forest trees," Mar. 2015, 35 Pages.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Giraldo, A., et al., "Phyiogeny of Sarocladium (*Hypocreales*)," Persoonia, 2015, pp. 10-24, vol. 34.
Girard, G., et al., "A novel taxonomic marker that discriminates between morphologically complex actinomycetes", Open Biology, vol. 3, No. 10, Oct. 2013, p. 130073,XP055675916.
Gitaitis, R., et al., "The Epidemiology and Management of Seedborne Bacterial Diseases," Annu Rev Phytopathol., 2007, pp. 371-397, vol. 45.
Gopalakrishnan, S. et al., "Plant growth-promoting activities of *Streptomyces* spp. In sorghum and rice", SpringerPlus, 2/1/574, pp. 1-8, http://www.springerplus.com/content/2/1/574, 2013.
Goudjal, Y., et al., "Biocontrol of Rhizoctonia solani damping-off and promotion of tomato plant growth by endophytic actinomycetes isolated from native plants of Algerian Sahara", Microbiological Research, 2014, vol. 169, No. 1, pp. 59-65.
Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.
Grondona, I., et al., "Tusal®, a commercial biocontrol formulation based on Trichoderma," Bulletin OILB/SROP, 2004, pp. 285-288, vol. 27, No. 8.
Groppe, K., et al., "Interaction between the endophytic fungus Epichloë bromicola and the grass Bromus erectus: effects of endophyte infection, fungal concentration and environment on grass growth and flowering," Mol Ecol., 8:1827-1835, 1999.
Gu, O., et al., "*Glyoomyces sambucus* sp. nov., an endophytic actinomycete islolaled from the stem of Sambucus adnata Wall," International Journal of Systematic and Evolutionary Microbiology, 2007, pp. 1995-1998, vol. 57.
Guo, X., et al., "Red Soils Harbor Diverse Culturable Actinomycetes That Are Promising Sources of Novel Secondary Metaboiites", Applied and Environmental Microbiology, Feb. 27, 2015, vol. 81, No. 9, pp. 3086-3103.
Guo, Y., et al. "A multi locus phylogeny of the Streptomyces griseus 16S rRNA gene clade: use of multilocus sequence analysis for streptomycete systematics", International Journal of Systematic and Evolutionary Microbiology, vol. 58, No. 1, 2008, pp. 149-159, XP055675936.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Visagie, C.M., et al., "Identification and nomenclature of the genus Penicillium," Studies in Mycology, Jun. 2014, pp. 343-371, vol. 78.
Vujanovic, V., et al., "19th International Conference on *Arabidopsis*. Research Proceedings—ICAR13," Jul. 23-27, 2008, 264 Pages, Montreal, QC, Canada.
Vujanovic, V., el al., "A comparative study of endophytic mycobiota in leaves of Acer saccharum in eastern North America," Mycological Progress, May 2002, pp. 147-154, vol. 1, Issue 2.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "Mycovitality—a new concept of plant biotechnology," Canadian Journal Plant Pathol. 2007, vol. 29, p. 451.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci., NRC Research Press, Feb. 6, 2017, pp. 972-981, vol. 97.

(56) References Cited

OTHER PUBLICATIONS

Vujanovic, V., et al., "Viability Testing of Orchid Seed and the Promotion of Colouration and Germination," Annals of Botany, Mar. 17, 2000, pp. 79-86, vol. 86.

Vujanovic, V., et al.,"Orchid seed viability testing by fungal bioassays and molecular phylogeny," Floriculture, ornamental and plant biotechnology, 2006, vol. 63, pp. 563-569.

Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.

Waller, F., et al., "The Endophytic Fungus Piriformospora indica Reprograms Barley to Salt-Stress Tolerance, Disease Resistance, and Higher Yield," PNAS, 2005, pp. 13386-13391, vol. 102, No. 38.

Wiegand, I., et al., "Agar and Broth Dilution Methods to Determine the Minimal Inhibitory Concentration (MIC) of AntiMicrobiol Substances," Nature Protocols, 2008, pp. 163-175, vol. 3, No. 2.

Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings" World J Microbiol Biotechnol., 2014, pp. 835-845, vol. 30.

Xu. Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.

Xue, Q.Y., et al., "Evaluation of the Strains of Acinetobacter and Enterobacter as potential Biocontrol Agents Against Ralstonia Will of Tomato," Biological Control, 2009, vol. 48, pp. 252-258.

Yandigeri, M. S., et al.. "Drought-tolerant endophytic actinobacteria promote growth of wheat (*Triticum aestivum*) under water stress conditions," Plant Growth Regulation, 2012, pp. 411-420, vol. 68.

Yashiro et al., "Effect of Streptomycin Treatment on Bacterial Community Structure in the Apple Phyllosphere," PLOS ONE, May 21, 2012, vol. 7, No. 5, 10 pages.

Yennamalli, R., et al., "Endoglucanases: insights into thermostability for biofuel applications", Biotech Biofuels, 2013, vol. 6, Issue 136, pp. 1-9.

Yezerski, A., et al., "The Effects of the Presence of Stored Product Pests on the Microfauna of a Flour Community," Journal of Applied Microbiology, 2005, pp. 507-515, vol. 98.

You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4, (with English Abstract).

Youssef, Y.A., et al., "Production of Plant Growth Substances by Rhizosphere Myoflora of Broad Bean and Cotton," Biologia Plantarum, 1975, pp. 175-181, vol. 17, No. 3.

Zhang, J., et al. "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50 No. 2, pp. 191-198, GenBank Accession No: JN210900.

Zhang, W., et al., Host range of Exserohilum monoceras, a potential bioherbicide for the control of *Echinochloa* species, Canadian Journal of Botany/ Journal Canadien De Botan, National Research Council, Ottawa, CA. vol. 75, Jan. 1, 1997, pp. 685-692.

Zhang, Y., et al., "BcGs1, a glycoprotein from Botrytis cinerea, elicits defence response and improves disease resistance in host plants. Biochemical and biophysical research communications," Biochemical and Biophysical Research Communications, 2015, vol. 457, No. 4, pp. 627-634.

Zhao, J.H., et al., "Bioactive secondary metabolites from *Nigrospora* sp. LLGLM003, an endophylic fungus of the medicinal plant *Moringa oleifera* Lam." World Journal of Microbiology and Biotechnology, Kluwer Academic Publishers, Feb. 12, 2012, pp. 2107-2112, vol. 28, No. 5.

Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.

Zhou, W., et al., "Effects of the Fungal Endophyte *Paecilomyces* sp. in Cotton on the Roo-Knot Nematode Meloidogyne incognita," poster dated Jan. 7, 2013.

Zhu et al., "*Helminthosporium velutinum and H. aquaticum* sp. nov. from aquatic habitats in Yunnan Province, China." Phytotaxa, 2016, vol. 253, No. 3, pp. 179-190.

Zimmerman, N.B., et al., "Fungal Endophyte Communities Reflect Environmental Stmcturing Across a Hawaiian Landscape," Proc Natl Acad Sci USA, 2012, pp. 13022-13027, vol. 109, No. 32.

Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.

\* cited by examiner

BACTERIAL INOCULANTS

CROSS REFERENCE TO RELATED APPLICATIONS

This application is the National Stage of International Application No. PCT/AU/2018/050387, filed Apr. 27, 2018, which claims priority to Australian Provisional Application No. 2017901523, filed Apr. 27, 2017, and to U.S. Provisional Application No. 62/568,763, filed Oct. 5, 2017, the disclosures of which are incorporated by reference in their entirety.

SEQUENCE LISTING

The instant application contains a Sequence Listing with 4686 sequences which has been submitted via EFS in conjunction with this specification and is hereby incorporated by reference in its entirety. Said ASCII copy is named IFU-6401WOUS Sequence_Listing.txt, and is 35,340,406 bytes in size.

FIELD

The present invention relates to bacterial inoculants, and methods for their use, to control a fungal root disease in a plant and promote plant growth in water limited conditions.

BACKGROUND

Root diseases are a major constraint in cropping systems worldwide. Root diseases are difficult to control with fungicides as they are below ground and management practices often provide only partial reductions in disease.

Two major genera of fungal root rot pathogens are *Rhizoctonia* and *Pythium* which infect multiple crop types in broad acre and horticulture crops. These pathogens infect roots of plants, reducing germination and establishment of emerging seedlings and causing loss of root hairs and breakdown of roots in established plants and thereby reducing the plants access to water and nutrients resulting in reduced growth and yield. In broad acre cereal cropping systems these pathogens are ubiquitous and the increase in minimal or no-till tillage practices has increased the impact of these diseases. Their broad host range means there are few non-host crops to use in rotations to reduce pathogen inoculum and there are no resistant cereal cultivars available.

In dryland cereal cropping systems, *Rhizoctonia* root rot, caused by *Rhizoctonia solani* anastomosis group AG8 is the main fungal root disease, especially in low rainfall zones, causing an estimated yield loss of Aus $77 mil per annum in Australia. *R. oryzae* is also an important root pathogen in cereals. *Pythium* damping off and root rot is caused by a number of *Pythium* species, with *P. irregulare* and *P. ultimum* being the main species infecting cereals with the prevalence and severity of disease increasing in higher rainfall zones causing an estimated yield loss of Aus $11 mil per annum in Australia.

The incidence and severity of *Rhizoctonia* and *Pythium* diseases on crop plants are known to be influenced by soil and plant associated microbes, with numerous reports of bacteria and fungi able to reduce disease under controlled conditions in pots. However, further improved microbial inoculants to control fungal root diseases in valuable crops, such as wheat or canola, are desirable.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DESCRIPTION

Figure 1:
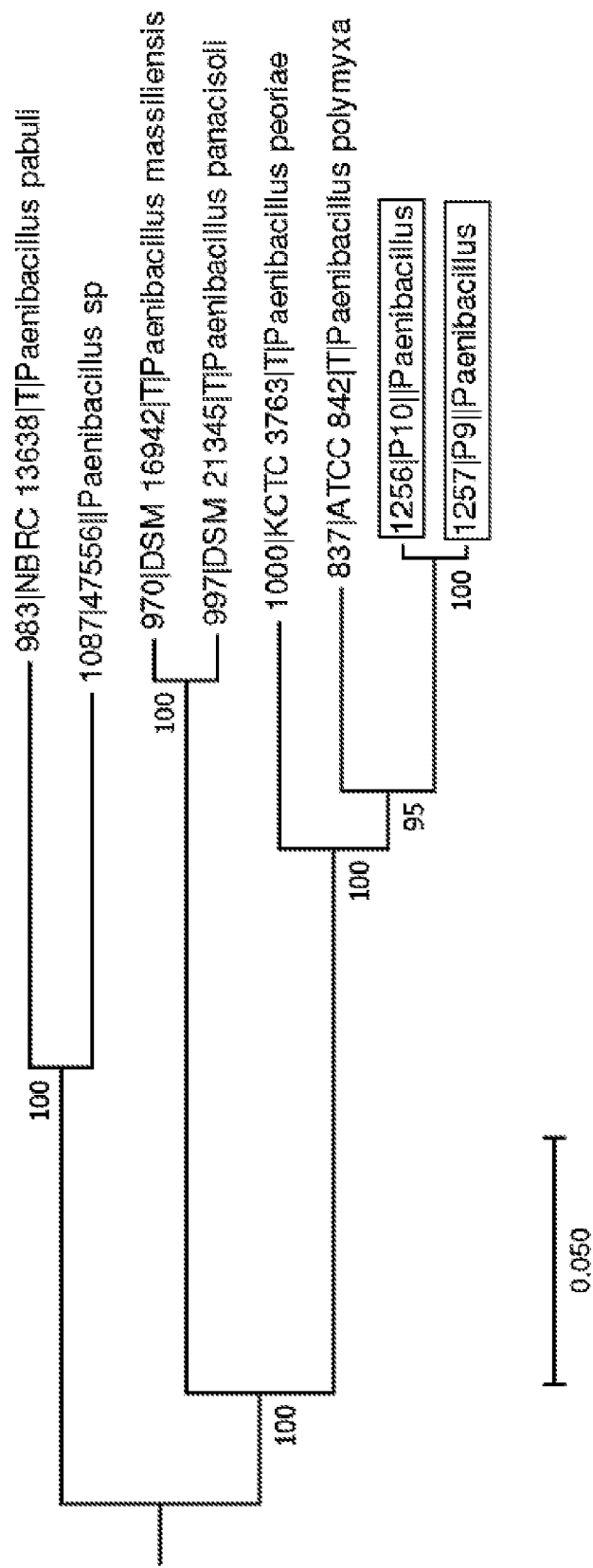
FIG. 1 depicts a phylogenetic tree visualizing the phylogenetic relationship between strain 9.4E (P9), strain 10.6D (P10), and other *Paenibacillus* strains.

Nucleotide and amino acid sequences are referred to herein by a sequence identifier number (SEQ ID NO:). A summary of the sequence identifiers is provided below:

| Sequence Identifier | Description |
| --- | --- |
| SEQ ID NO: 1 | 27f primer nucleotide sequence |
| SEQ ID NO: 2 | 1465r primer nucleotide sequence |
| SEQ ID NO: 3 | *Paenibacillus* sp. 10.6D 16S rRNA gene nucleotide sequence |
| SEQ ID NO: 4 | *Paenibacillus* sp. 9.4E 16S rRNA gene nucleotide sequence |
| SEQ ID NO: 5 | *Streptomyces* sp. HSA1273 16S rRNA gene nucleotide sequence |
| SEQ ID NO: 6 | *Streptomyces* sp. BD141 16S rRNA gene nucleotide sequence |
| SEQ ID NO: 7 | *Paenibacillus* sp. 9.4E atpD gene nucleotide sequence |
| SEQ ID NO: 8 | *Paenibacillus* sp. 9.4E recA gene nucleotide sequence |
| SEQ ID NO: 9 | *Paenibacillus* sp. 9.4E trpB gene nucleotide sequence |
| SEQ ID NO: 10 | *Paenibacillus* sp. 9.4E gyrB gene nucleotide sequence |
| SEQ ID NO: 11 | *Paenibacillus* sp. 10.6D recA gene nucleotide sequence |
| SEQ ID NO: 12 | *Paenibacillus* sp. 10.6D atpD gene nucleotide sequence |
| SEQ ID NO: 13 | *Paenibacillus* sp. 10.6D trp gene nucleotide sequence |
| SEQ ID NO: 14 | *Paenibacillus* sp. 10.6D gyrB gene nucleotide sequence |
| SEQ ID NO: 15,*Paenibacillus* sp. 10.6D full genome sequence 19-75 | |
| SEQ ID NO: 16,*Streptomyces* sp. H0A1273 full genome sequence 76-2592 | |
| SEQ ID NO: 17,*Paenibacillus* sp. 9.4E full genome sequence 2593-2707 | |
| SEQ ID NO: 18,*Streptomyces* sp. BD141 full genome sequence 2708-4686 | |

In this work over 2,000 microbial strains were screened in a multi-tiered screening system to identify strains which can reduce disease when applied to seeds under field cropping conditions. Strains were sequentially screened in a high-throughput plant-pathogen tube system, then pot bioassay systems, characterised, and selected strains assessed in field trials. Field trials were carried out in cereal growers' paddocks with naturally occurring pathogen inoculum.

In a first aspect, the present invention provides a bacterial inoculant for controlling a fungal root disease on a plant.

A "bacterial inoculant" as referred to herein should be understood as any isolated microorganism which may be inoculated onto a plant in order to control a fungal root disease.

An "isolated" bacterial microorganism should be understood to be any bacterial microorganism which has been removed from its native environment and grown or cultured in vitro. In some embodiments, an isolated bacterial microorganism may be substantially purified and thus grown or cultured substantially in the absence of other microorganisms. Alternatively, in some embodiments, the isolated microorganism may be co-cultured with one or more additional microorganisms.

As referred to herein, terms such as "inoculating", "inoculated", "inoculation" and the like should be understood to include any method or process wherein a plant (including without limitation a plant seed, leaf, root) is brought into contact with a bacterial inoculant by human ingenuity such that the bacterial inoculant exists on or in the plant in a manner not found in nature prior to the application of the bacterial inoculant. In some embodiments inoculation may comprise the bacterial inoculant being applied to a wheat seed or canola plant seed. In some embodiments inoculation may comprise the bacterial inoculant being applied to soil in which a wheat or canola plant is growing or in which a wheat or canola seed will be planted. In some embodiments, inoculation may comprise the bacterial inoculant being applied to root and/or shoot tissue of a wheat or canola plant. In some embodiments inoculation may be the mechanical or manual application, artificial inoculation or disposition of a bacterial inoculant onto or into a plant or plant growth medium. A plant growth medium is any composition or environment in which a plant may be grown. In some embodiments, the plant growth medium is soil.

As described later, in some embodiments, the bacterial inoculants contemplated by the present invention are from a specific genus or species, comprise a defining 16S rRNA gene nucleotide sequence, and/or comprise a defined bacterial strain.

As also set out above, the present invention contemplates control of a fungal disease of a plant. In some embodiments, the fungal disease is a root disease of a monocot or dicot plant. In some embodiments, the monocot is a cereal plant. In some embodiments the cereal plant is member of the plant family Poaceae or Gramineae, for example: wheat, rice, corn, barley, millet, sorghum, oat, rye, or related grain producing plant. In some embodiments, the dicot is a member of the plant family Fabaceae or Leguminosae, for example: soybeans, peas, beans, lentils, peanuts, alfalfa, clover, or related plants. In some embodiments, the dicot is a member of the plant family Brassicaceae or Cruciferae, for example: canola, rapeseed, cabbage, cauliflower, kale, radish, mustard, turnip, or related plants.

A "wheat plant", as referred to herein, should be understood to include plants of the genus *Triticum*. In some embodiments, the term "wheat" should be understood to include one or more of diploid wheat, tetraploid wheat and/or hexaploid wheat. In some embodiments, the wheat plant may be a cultivated species of wheat including, for example, *Triticum aestivum, Triticum durum, Triticum monococcum* or *Triticum spelta*. In some embodiments, the term "wheat" refers to wheat of the species *Triticum aestivum*.

A "canola plant", as referred to herein, should be understood to include plants of the genus *Brassica*, particularly *B. napus, B. rapa, B. campestris, B. oleracea, B. montana*, and hybrids thereof. In some embodiments, the term "canola" should be understood to include one or more of rape, rapeseed, oilseed rape, Argentine canola, and colza. In some embodiments, the canola plant may be a cultivated species of canola. In some embodiments, the canola plant may be a species canola of including, for example, *B. napus* subsp. *oleifera, B. napus* subsp. *napus, B. napus* subsp. *napus f. annua, B. napus* subsp. *napus f. napus, Brassica campestris* subsp. *napus*, or *Brassica rapa* subsp. *oleifera*. In some embodiments, the term "canola" refers to canola of the species *Brassica napus* L and subspecies thereof.

As also set out above, the present invention contemplates bacterial inoculants for the control of a fungal disease in a plant. In some embodiments, the fungal disease is a root disease of a monocot or dicot plant. In some embodiments, the present invention contemplates bacterial inoculants for the control of a fungal root disease in a wheat plant or a canola plant.

In some embodiments, "control" of a fungal root disease in a plant may be understood as enhancement of one or more growth parameters in an inoculated plant relative to an uninoculated plant of the same taxon in the presence of the fungal root disease. In some embodiments, the plant is a wheat plant or a canola plant.

In some embodiments, enhancement of a growth parameter will include an increase in the measured value of the growth parameter. For example, an increase in one or more of:

a length and/or mass of a shoot; a length and/or mass of a root; a number and/or mass of seed;

a concentration and/or amount of a nutrient; or a germination rate.

In some embodiments, an "increase" in a growth parameter may include, for example, a 1%, 5%, 10%, 20%, 30%, 40%, 50%, 60%, 70%, 80%, 90%, 100%, 2-fold, 5-fold, 10-fold, 20-fold, 50-fold, 100-fold increase in the growth parameter in an inoculated plant relative to a plant of the same taxon that has not been inoculated. In some embodiments, the plant is grown in the presence of a fungal root disease. In some embodiments, the plant is grown in water limited conditions. In some embodiments, the plant is a wheat plant or a canola plant.

In some embodiments, however, "enhancement" of the growth parameter may include a decrease in the measured value of the growth parameter. For example, a decrease in the concentration and/or amount of a pathogen, disease symptom and/or toxin in the plant, and/or a decrease in the time of germination of a wheat or canola plant seed, may be considered "enhancement" of such growth parameters.

In some embodiments, a "decrease" in a growth parameter may include, for example, a 1%, 5%, 10%, 20%, 30%, 40%, 50%, 60%, 70%, 80%, 90%, 95% or 100% decrease in the growth parameter in an inoculated plant relative to a plant of the same taxon that has not been inoculated. In some embodiments, the plant is grown in the presence of a fungal root disease. In some embodiments, the plant is grown in water limited conditions. In some embodiments, the plant is a wheat plant or a canola plant.

In some embodiments, enhancement of a growth parameter may comprise enhancement within a particular time period. For example, in some embodiments, enhancement of the growth parameter may comprise enhancement over a time period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 days.

As set out above, the present invention contemplates a bacterial inoculant for controlling a fungal root disease on a wheat or canola plant. A "fungal root disease" as referred to herein should be understood as any disease of a plant which infects or damages the roots of the plant and which is caused by a fungus or fungal-like pathogen. A "fungal-like" pathogen should be understood to specifically include Oomycete pathogens such as pathogens of the genus *Pythium*. In some embodiments, the fungal root disease is a disease of a wheat or canola plant.

In some embodiments, the fungal root disease is caused by a pathogen of the genus *Rhizoctonia*. In some embodiments, the pathogen is of the species *Rhizoctonia solani*. In some embodiments, the pathogen is *Rhizoctonia solani* AG8. In some embodiments, the pathogen is of the species *Rhizoctonia oryzae*.

In some embodiments, the bacterial inoculant of the first aspect of the invention includes a microorganism of the genus *Paenibacillus* that is able to at least control a fungal root disease caused by a pathogen of the genus *Rhizoctonia*. In some embodiments, the microorganism of the genus *Paenibacillus* is able to at least control a pathogen of the genus *Rhizoctonia* on or in a wheat or canola plant.

In some embodiments bacterial inoculant of the genus *Paenibacillus* includes a microorganism having a 16S rRNA gene nucleotide sequence which is at least 98% identical to SEQ ID NO: 3. In some embodiments the microorganism comprises a 16S rRNA gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 3.

In some embodiments bacterial inoculant of the genus *Paenibacillus* includes a microorganism having an atpD gene nucleotide sequence which is at least 98% identical to SEQ ID NO: 7. In some embodiments the microorganism comprises an atpD gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 7.

In some embodiments bacterial inoculant of the genus *Paenibacillus* includes a microorganism having a recA gene nucleotide sequence which is at least 98% identical to SEQ ID NO: 8. In some embodiments the microorganism comprises a recA gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 8.

In some embodiments bacterial inoculant of the genus *Paenibacillus* includes a microorganism having a trpB gene nucleotide sequence which is at least 98% identical to SEQ ID NO: 9. In some embodiments the microorganism comprises a trpB gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 9.

In some embodiments bacterial inoculant of the genus *Paenibacillus* includes a microorganism having a gyrB gene nucleotide sequence which is at least 98% identical to SEQ ID NO: 10. In some embodiments the microorganism comprises a gyrB gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 10.

In some embodiments bacterial inoculant of the genus *Paenibacillus* includes a microorganism having a recA gene nucleotide sequence which is at least 98% identical to SEQ ID NO: 11. In some embodiments the microorganism comprises a recA gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 11.

In some embodiments bacterial inoculant of the genus *Paenibacillus* includes a microorganism having an atpD gene nucleotide sequence which is at least 98% identical to SEQ ID NO: 12. In some embodiments the microorganism comprises an atpD gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 12.

In some embodiments bacterial inoculant of the genus *Paenibacillus* includes a microorganism having a trpB gene nucleotide sequence which is at least 98% identical to SEQ ID NO: 13. In some embodiments the microorganism comprises a trpB gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 13.

In some embodiments bacterial inoculant of the genus *Paenibacillus* includes a microorganism having a GyrB gene nucleotide sequence which is at least 98% identical to SEQ ID NO: 14. In some embodiments the microorganism comprises a gyrB gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 14.

When comparing nucleic acid sequences to calculate a percentage identity (in relation to any of the SEQ ID NOS herein, the compared nucleic acid sequences should be compared over a comparison window of, for example, at least 100 nucleotide residues, at least 300 nucleotide residues, at least 600 nucleotide residues, at least 1000 nucleotide residues, at least 1100 nucleotide residues, at least 1200 nucleotide residues, at least 1300 nucleotide residues or at least 1400 nucleotide residues. In some embodiments, the comparison window may comprise the region in each of the compared nucleotide sequences between and including the binding sites of the 27f primer (SEQ ID NO: 1) and the 1465r primer (SEQ ID NO: 2) on the compared nucleotide sequences. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms such as the BLAST family of programs as, for example, disclosed by Altschul et al. (Nucl. Acids Res. 25: 3389-3402, 1997). A detailed discussion of sequence analysis can be found in Unit 19.3 of Ausubel et al. (Current Protocols in Molecular Biology, John Wiley & Sons Inc., Chapter 15,1998).

A number of particularly useful actinobacterial microorganisms of the present invention have been deposited with the National Measurement Institute ('NMI'), 1/153 Bertie Street, Port Melbourne, Victoria, 3207, Australia, in accordance with the provisions of the Budapest Treaty on the International Recognition of the Deposit of Microorganisms for the Purposes of Patent Procedure.

Accordingly, in some embodiments, the bacterial inoculant includes microorganism *Paenibacillus* sp. 10.6D as deposited on 9 Mar. 2017 with the National Measurement Institute under NMI accession number V17/004922; or a mutant or derivative of said deposited microorganism that retains the ability to control a fungal root disease in a wheat or canola plant. In some embodiments, the mutant or derivative retains the ability to control a fungal root disease in a wheat or canola plant, where the root disease is caused by a pathogen of the genus *Rhizoctonia*.

A "mutant or derivative" of the subject deposited microorganisms referred to herein should be understood to encompass, for example, any spontaneous or induced mutant, conjugation progeny or genetically modified form of a deposited strains which retains the ability to enhance one or more growth parameters of a plant. In some embodiments, a mutant or derivative retains the ability to enhance one or more growth parameters of a wheat or canola plant in the presence of the fungal root disease or under water limited conditions. Mutagenisation techniques that may be used to generate derivatives or mutants include, for example, chemical mutagenesis (e.g., EMS mutagenesis), ionising radiation-induced mutagenesis (e.g., X-ray mutagenesis, y-ray mutagenesis and UV mutagenesis), genetic insertion mutagenesis methods (e.g., transposon mutagenesis) and the like.

In some embodiments, the bacterial inoculant of the first aspect of the invention includes a microorganism of the genus *Streptomyces* that is able to at least control a fungal root disease caused by a pathogen of the genus *Rhizoctonia*. In some embodiments, the microorganism of the genus *Streptomyces* is able to at least control a pathogen of the genus *Rhizoctonia* on or in a wheat or canola plant.

In some embodiments bacterial inoculant of the genus *Streptomyces* includes a microorganism having a 16S rRNA gene nucleotide sequence which is at least 98% identical to SEQ ID NO: 5. In some embodiments the microorganism comprises a 16S rRNA gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 5.

In some embodiments, the bacterial inoculant includes microorganism *Streptomyces* sp. HCA1273 as deposited on 9 Mar. 2017 with the National Measurement Institute under NMI accession number V17/004924; or a mutant or derivative of said deposited microorganism that retains the ability to control a fungal root disease in a wheat or canola plant. In some embodiments, the mutant or derivative retains the ability to control a fungal root disease in a wheat or canola plant, where the root disease is caused by a pathogen of the genus *Rhizoctonia*.

In some embodiments, the fungal root disease is caused by a pathogen of the genus *Pythium*. In some embodiments, the pathogen is of the species *Pythium irregulare*. In some embodiments, the pathogen is of the species *Pythium ultimum*.

In some embodiments, the bacterial inoculant of the first aspect of the invention includes a microorganism of the genus *Paenibacillus* that is able to at least control a fungal root disease caused by a pathogen of the genus *Pythium*. In some embodiments, the microorganism of the genus *Paenibacillus* is able to at least control a pathogen of the genus *Pythium* in or on a wheat or canola plant.

In some embodiments bacterial inoculant of the genus *Paenibacillus* includes a microorganism having a 16S rRNA gene nucleotide sequence which is at least 98% identical to SEQ ID NO: 4. In some embodiments the microorganism comprises a 16S rRNA gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 4.

In some embodiments, the bacterial inoculant includes microorganism *Paenibacillus* sp. 9.4E as deposited on 9 Mar. 2017 with the National Measurement Institute under NMI accession number V17/004921; or a mutant or derivative of said deposited microorganism that retains the ability to control a fungal root disease in a wheat or canola plant. In some embodiments, the mutant or derivative retains the ability to control a fungal root disease in a wheat or canola plant, where the root disease is caused by a pathogen of the genus *Pythium*.

In some embodiments, the bacterial inoculant of the first aspect of the invention includes a microorganism of the genus *Streptomyces* that is able to at least control a fungal root disease caused by a pathogen of the genus *Pythium* on a wheat or canola plant. In some embodiments, the microorganism of the genus *Streptomyces* is able to at least control a pathogen of the genus *Pythium* on a wheat or canola plant.

In some embodiments bacterial inoculant of the genus *Streptomyces* includes a microorganism having a 16S rRNA gene nucleotide sequence which is at least 98% identical to SEQ ID NO: 6. In some embodiments the microorganism comprises a 16S rRNA gene nucleotide sequence which is at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to SEQ ID NO: 6.

In some embodiments, bacterial inoculants and methods disclosed herein include a microorganism having a gene, e.g., a 16S rRNA gene, having a nucleotide sequence at least 97%, 98%, 99% or 100% identical to the same gene nucleotide sequence found in one of the genomic sequences found in Table 1. In some embodiments the microorganism comprises a gene having a nucleotide sequence of at least 97%, at least 97.1%, at least 97.2% at least 97.3%, at least 97.4%, at least 97.5%, at least 97.6%, at least 97.7%, at least 97.8%, at least 97.9%, at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to the same gene nucleotide sequence found in one of the genomic sequences found in Table 1.

In some embodiments, the bacterial inoculant includes microorganism *Streptomyces* sp. BD141 as deposited on 9 Mar. 2017 with the National Measurement Institute under NMI accession number V17/004923; or a mutant or derivative of said deposited microorganism that retains the ability to control a fungal root disease in a wheat or canola plant. In some embodiments, the mutant or derivative retains the ability to control a fungal root disease in a wheat or canola plant, where the root disease is caused by a pathogen of the genus *Pythium*.

In a second aspect, the present invention provides an inoculant composition comprising one or more bacterial inoculants as hereinbefore described.

In some embodiments, the inoculant composition further comprises a carrier or additive. The carrier or additives used will depend on the nature of the inoculant composition. For example, the inoculant composition may be in the form of a liquid composition, a solid composition (such as a powder, pellet or granular composition) a seed dressing or the like. In some embodiments, the inoculant composition comprises a seed dressing.

A range of useful carriers or additives would be readily apparent to those of skill in the art and may include, for example: one or more gums (including xanthan gum), clay or peat based carriers, one or more nutrients including carbon or nitrogen sources, one or more antifungal or antibacterial agents, one or more seed coating agents, one or more wetting agents and the like.

The inoculant compositions of the present invention may be adapted to be applied to a plant, for example a wheat or canola plant, in any suitable way. For example, the inoculant composition could be adapted to be applied as a seed coating, applied as a solid or liquid composition to the foliage or roots of a plant, or applied as a solid or liquid composition to soil before, during or after sowing of a plant, for example a wheat or canola plant.

In a third aspect, the present invention provides a method for controlling a fungal root disease on a plant, the method comprising inoculating a plant with a bacterial inoculant or inoculant composition as hereinbefore described.

In some embodiments, the plant is a wheat plant or a canola plant.

In some embodiments, the root disease is caused by a pathogen of the genus *Rhizoctonia*.

In some embodiments, the root disease is caused by a pathogen of the genus *Pythium*.

In some embodiments, the bacterial inoculant or inoculant composition are inoculated onto a seed. In some embodiments, the bacterial inoculant or inoculant composition are inoculated onto a wheat seed or canola seed.

In a fourth aspect, the present invention provides a method for improving growth of a plant under water limited conditions, the method comprising inoculating a plant with a bacterial inoculant or inoculant composition as hereinbefore described.

In some embodiments, the method provides for improving growth of a monocot or dicot plant under water limited conditions. In some embodiments, the monocot is a cereal plant. In some embodiments the cereal plant is member of the plant family Poaceae or Gramineae, for example: wheat, rice, corn, barley, millet, sorghum, oat, rye, or related grain producing plant. In some embodiments, the dicot is a member of the plant family Fabaceae or Leguminosae, for example: soybeans, peas, beans, lentils, peanuts, alfalfa, clover, or related plants. In some embodiments, the dicot is a member of the plant family Brassicaceae or Cruciferae, for example: canola, rapeseed, cabbage, cauliflower, kale, radish, mustard, turnip, or related plants.

Water limited conditions, include but are not limited to, drought conditions and dryland (non-irrigated) environments. In some embodiments, water limited conditions are growth conditions where the amount of water available to the plants is less than the amount necessary to support optimal plant growth. In some embodiments, the water limited condition comprises less than 5%, 10%, 20%, 30%, 40%, 50%, 60%, 70%, 75%, 80%, 85%, 90%, 95%, 97%, less than 100% of the amount necessary to support optimal plant growth. In some embodiments, the amount of water necessary to support optimal plant growth is measured in average or above average yield. In some embodiments, the water limited conditions are the amount of water that result in a reduction in average yield of un-inoculated plants by at least 5%, at least 10%, between 5-15%, about 15%, at least 20%, about 20%, between 20-25%, or at least 25%. In some embodiments, the water limited conditions are a non-irrigated field. In some embodiments, the water limited condition comprises a 1%, 2%, 3%, 4%, 5%, 10%, 20%, 30%, 40%, 50% reduction in rainfall relative to the 1 year, 2, 3, 4, 5 year, 6, 7, 8, 9, 10 year historical average rainfall for the geography. In some embodiments, the water limited conditions are controlled by human endeavor in greenhouse or laboratory assays. A non-limiting example of a laboratory assay conducted in water limited conditions is growth of a plant in an aqueous solution comprising polyethylene glycol (PEG), for example 7.5% PEG 6000.

In a fifth aspect, the present invention provides a bacterial inoculant as described herein with respect to any of the examples.

In a sixth aspect, the present invention provides an inoculant composition as described herein with respect to any of the examples.

In a seventh aspect, the present invention provides a method for controlling a fungal root disease on a wheat or canola plant as described herein with respect to any of the examples.

In an eighth aspect, the present invention provides a method for a method for improving growth of a wheat or canola plant under water limited as described herein with respect to any of the examples.

The present invention is further described with reference to the following non-limiting examples:

EXAMPLE 1

Bacterial Inoculants for Control of Fungal Root Disease in Wheat or Canola

A number of microbial strains were screened in a series of in planta bioassays, characterised and assessed in field trials using naturally occurring pathogen inoculum. Four strains were identified as being of interest, as shown in Table 1.

TABLE 1

Strains identified as beneficial inoculants in grain cropping systems

| Strain Identifier | Alternative name | Full Genome Sequence (SEQ ID NO:) | Genus | Function—crop |
|---|---|---|---|---|
| 10.6D | P10 | SEQ ID NO: 15 | *Paenibacillus* | Rhizoctonia control—wheat or canola |
| HCA1273 | S12 | SEQ ID NO: 16 | *Streptomyces* | Rhizoctonia control—wheat or canola |
| 9.4E | P9 | SEQ ID NO: 17 | *Paenibacillus* | Pythium control—wheat |
| BD141 | S14 | SEQ ID NO: 18 | *Streptomyces* | Pythium control—wheat |

EXAMPLE 2

Identification

DNA of each strain was extracted. Two sections of 16S rRNA were amplified by PCR using primers 27f (agagtttgat cctggctcag, SEQ ID NO: 1) and 1492r (tacggytacc ttgttacgac tt, SEQ ID NO: 2). PCR products were sequenced by Sanger sequencing, two replicate extractions and forward and reverse directions of PCR fragments were sequenced. Sequences were identified using Ezbiocloud (www.ezbiocloud.net). Sequences were aligned with 20 closest matches using ClustalW in Mega7 and phylogeny inferred using Maximum Likelihood Tree and Nearest Neighbour Joining Trees. Results are shown in Tables 2 and 3.

TABLE 2

Identification of 10.6D, 9.4E, HCA1273, BD141

| Strain | Closest matches with type strains | Pairwise similarity % |
|---|---|---|
| 10.6D | *Paenibacillus peoriae* DSM8320$^T$ | 99.63 |
|  | *Paenibacillus kribbensis* AM49$^T$ | 98.90 |
| 9.4E | *Paenibacillus peoriae* DSM8320$^T$ | 98.99 |
|  | *Paenibacillus kribbensis* AM49$^T$ | 98.52 |
| HCA1273 | *Streptomyces prasinosporus* NRRLB12431$^T$ | 98.66 |
|  | *Streptomyces scopiformis* NBRC14215$^T$ | 98.36 |
| BD141 | *Streptomyces cyaneofuscatus* NRRLB2570$^T$ | 99.86 |
|  | *Streptomyces griseus* subsp. *griseus* KCTC9080 | 99.86 |

TABLE 3

16S rRNA sequences of 10.6D, 94.E, HCA1273, BD141, 5' to 3' orientation

| Strain | 16S rRNA sequence |
|---|---|
| 10.6D | GGATGGGCCTGCGGCGCATTAGCTAGTTGGTGGGGTAAAGGCCTACCAAGGCGA<br>CGATGCGTAGCCGACCTGAGAGGGTGATCGGCCACACTGGGACTGAGACACGGC<br>CCAGACTCCTACGGGAGGCAGCAGTAGGGAATCTTCCGCAATGGGCGAAAGCCT<br>GACGGAGCAACGCCGCGTGAGTGATGAAGGTTTTCGGATCGTAAAGCTCTGTTGC<br>CAGGGAAGAACGTCTTGTAGAGTAACTGCTACAAGAGTGACGGTACCTGAGAAG<br>AAAGCCCCGGCTAACTACGTGCCAGCAGCCGCGGTAATACGTAGGGGGCAAGCG<br>TTGTCCGGAATTATTGGGCGTAAAGCGCGCGCAGGCGGCTCTTTAAGTCTGGTGT<br>TTAATCCCGAGGCTCAACTTCGGGTCGCACTGGAAACTGGGGAGCTTGAGTGCAG<br>AAGAGGAGAGTGGAATTCCACGTGTAGCGGTGAAATGCGTAGAGATGTGGAGG<br>AACACCAGTGGCGAAGGCGACTCTCTGGGCTGTAACTGACGCTGAGGCGCGAAA<br>GCGTGGGGAGCAAACAGGATTAGATACCCTGGTAGTCCACGCCGTAAACGATGA<br>ATGCTAGGTGTTAGGGGTTTCGATACCCTTGGTGCCGAAGTTAACACATTAAGCAT<br>TCCGCCTGGGGAGTACGGTCGCAAGACTGAAACTCAAAGGAATTGACGGGGACC<br>CGCACAAGCAGTGGAGTATGTGGTTTAATTCGAAGCAACGCGAAGAACCTTACCA<br>GGTCTTGACATCCCTCTGACCGGTCTAGAGATAGACCTTTCCTTCGGGACAGAGG<br>AGACAGGTGGTGCATGGTTGTCGTCAGCTCGTGTCGTGAGATGTTGGGTTAAGTC<br>CCGCAACGAGCGCAACCCTTATGCTTAGTTGCCAGCAGGTCAAGCTGGGCACTCT<br>AAGCAGACTGCCGGTGACAAACCGGAGGAAGGTGGGGATGACGTCAAATCATCA<br>TGCCCCTTATGACCTGGGCTACACACGTACTACAATGGCCGGTACAACGGGAAGC<br>GAAATCGCGAGGTGGAGCCAATCCTAGAAAAGCCGGTCTCAGTTCGGATTGTAG<br>GCTGCAACTCGCCTACATGAAGTCGGAATTGCTAGTAATCGCGGATCAGCATGCC<br>GCGGTGAATACGTTCCCGGGTCTTGTACACACCGCCCGTCACACCACGAGAGTTT<br>ACAACACCCGAAGTCGGTGG (SEQ ID NO: 3) |
| 9.4E | GGATGGGCCTGCGGCGCATTAGCTAGTTGGTGGGGTAAAGGCCTACCAAGGCGA<br>CGATGCGTAGCCGACCTGAGAGGGTGATCGGCCACACTGGGACTGAGACACGGC<br>CCAGACTCCTACGGGAGGCAGCAGTAGGGAATCTTCCGCAATGGGCGAAAGCCT<br>GACGGAGCAACGCCGCGTGAGTGATGAAGGTTTTCGGATCGTAAAGCTCTGTTGC<br>CAGGGAAGAACGTCTTGTAGAGTAACTGCTACAAGAGTGACGGTACCTGAGAAG |

TABLE 3-continued 16S rRNA sequences of 10.6D, 94.E, HCA1273, BD141, 5' to 3' orientation

| Strain | 16S rRNA sequence |
|---|---|
| | AAAGCCCCGGCTAACTACGTGCCAGCAGCCGCGGTAATACGTAGGGGGCAAGCG<br>TTGTCCGGAATTATTGGGCGTAAAGCGCGCGCAGGCGGCTCTTTAAGTCTGGTGT<br>TTAATCCCGAGGCTCAACTTCGGGTCGCACTGGAAACTGGGGAGCTTGAGTGCAG<br>AAGAGGAGAGTGGAATTCCACGTGTAGCGGTGAAATGCGTAGAGATGTGGAGG<br>AACACCAGTGGCGAAGGCGACTCTCTGGGCTGTAACTGACGCTGAGGCGCGAAA<br>GCGTGGGGAGCAAACAGGATTAGATACCCTGGTAGTCCACGCCGTAAACGATGA<br>ATGCTAGGTGTTAGGGGTTTCGATACCCTTGGTGCCGAAGTTAACACATTAAGCAT<br>TCCGCCTGGGGAGTACGGTCGCAAGACTGAAACTCAAAGGAATTGACGGGGACC<br>CGCACAAGCAGTGGAGTATGTGGTTTAATTCGAAGCAACGCGAAGAACCTTACCA<br>GGTCTTGACATCCCTCTGACCGGTCTAGAGATAGACCTTTCCTTCGGGACAGAGG<br>AGACAGGTGGTGCATGGTTGTCGTCAGCTCGTGTCGTGAGATGTTGGGTTAAGTC<br>CCGCAACGAGCGCAACCCTTATGCTTAGTTGCCAGCAGGTCAAGCTGGGCACTCT<br>AAGCAGACTGCCGGTGACAAACCGGAGGAAGGTGGGGATGACGTCAAATCATCA<br>TGCCCCTTATGACCTGGGCTACACACGTACTACAATGGCCGGTACAACGGGAAGC<br>GAAATCGCGAGGTGGAGCCAATCCTAGAAAAGCCGGTCTCAGTTCGGATTGTAG<br>GCTGCAACTCGCCTACATGAAGTCGGAATTGCTAGTAATCGCGGATCAGCATGCC<br>GCGGTGAATACGTTCCCGGGTCTTGTACACACCGCCCGTCACACCACGAGAGTTT<br>ACAACACCCGAAGTCGGTGG (SEQ ID NO: 4) |
| HCA1273 | GATGAAGCCCTTCGGGGTGGATTAGTGGCGAACGGGTGAGTAACACGTGGGCAA<br>TCTGCCCTGCACTCTGGGACAAGCCCTGGGAAACGGGGTCTAATACCGGATATGAG<br>TCTCCACCGCATGGTGGGGGCTGTAAAGCTCCGGCGGTGCAGGATGAGCCCGCG<br>GCCTATCAGCTTGTTGGTGAGGTAACGGCTCACCAAGGCGACGACGGGTAGCCG<br>GCCTGAGAGGGCGACCGGCCACACTGGGACTGAGACACGGCCCAGACTCCTACG<br>GGAGGCAGCAGTGGGGAATATTGCACAATGGGCGCAAGCCTGATGCAGCGACGC<br>CGCGTGAGGGATGACGGCCTTCGGGTTGTAAACCTCTTTCAGCAGGGAAGAAGC<br>GAAAGTGACGGTACCTGCAGAAGAAGCGCCGGCTAACTACGTGCCAGCAGCCGC<br>GGTAATACGTAGGGCGCAAGCGTTGTCCGGAATTATTGGGCGTAAAGAGCTCGT<br>AGGCGGCTTGTCGCGTCGGTTGTGAAAGCCCGGGGCTTAACCCCGGGTCTGCAGT<br>CGATACGGGCAGGCTAGAGTTCGGTAGGGGAGATCGGAATTCCTGGTGTAGCGG<br>TGAAATGCGCAGATATCAGGAGGAACACCGGTGGCGAAGGCGGATCTCTGGGCC<br>GATACTGACGCTGAGGAGCGAAAGCGTGGGGAGCGAACAGGATTAGATACCCTG<br>GTAGTCCACGCCGTAAACGGTGGGCACTAGGTGTGGGCGACATTCCACGTCGTCC<br>GTGCCGCAGCTAACGCATTAAGTGCCCCGCCTGGGGAGTACGGCCGCAAGGCTA<br>AAACTCAAAGGAATTGACGGGGGCCCGCACAAGCGGCGGAGCATGTGGCTTAAT<br>TCGACGCAACGCGAAGAACCTTACCAAGGCTTGACATACACCGGAAAACCCTGGA<br>GACAGGGTCCCCCTTGTGGTCGGTGTACAGGTGGTGCATGGCTGTCGTCAGCTCG<br>TGTCGTGAGATGTTGGGTTAAGTCCCGCAACGAGCGCAACCCTTGTCCCGTGTTG<br>CCAGCAGGCCCTTGTGGTGCTGGGGACTCACGGGAGACCGCCGGGGTCAACTCG<br>GAGGAAGGTGGGGACGACGTCAAGTCATCATGCCCCTTATGTCTTGGGCTGCACA<br>CGTGCTACAATGGCCGGTACAATGAGCTGCGATACCGTGAGGTGGAGCGAATCTC<br>AAAAAGCCGGTCTCAGTTCGGATTGGGGTCTGCAACTCGACCCCATGAAGTCGGA<br>GTCGCTAGTAATCGCAGATCAGCATTGCTGCGGTGAATACGTTCCCGGGCCTTGT<br>ACACACCGCCCGTCACGTCACGAAAGTCGGTAACACCCGAAGCCGGTGGCCCAAC<br>CCC (SEQ ID NO: 5) |
| BD141 | AGTCGAACGATGAAGCCTTTCGGGGTGGATTAGTGGCGAACGGGTGAGTAACAC<br>GTGGGCAATCTGCCCTTCACTCTGGGACAAGCCCTGGGAAACGGGGTCTAATACCG<br>GATAACACTCTGTCCCGCATGGGACGGGGTTAAAAGCTCCGGCGGTGAAGGATG<br>AGCCCGCGGCCTATCAGCTTGTTGGTGGGGTAATGGCCTACCAAGGCGACGACG<br>GGTAGCCGGCCTGAGAGGGCGACCGGCCACACTGGGACTGAGACACGGCCCAG<br>ACTCCTACGGGAGGCAGCAGTGGGGAATATTGCACAATGGGCGAAAGCCTGATG<br>CAGCGACGCCGCGTGAGGGATGACGGCCTTCGGGTTGTAAACCTCTTTCAGCAGG<br>GAAGAAGCGAAAGTGACGGTACCTGCAGAAGAAGCGCCGGCTAACTACGTGCCA<br>GCAGCCGCGGTAATACGTAGGGCGCAAGCGTTGTCCGGAATTATTGGGCGTAAA<br>GAGCTCGTAGGCGGCTTGTCACGTCGGATGTGAAAGCCCGGGGCTTAACCCCGG<br>GTCTGCATTCGATACGGGCTAGCTAGAGTGTGGTAGGGGAGATCGGAATTCCTG<br>GTGTAGCGGTGAAATGCGCAGATATCAGGAGGAACACCGGTGGCGAAGGCGGA<br>TCTCTGGGCCATTACTGACGCTGAGGAGCGAAAGCGTGGGGAGCGAACAGGATT<br>AGATACCCTGGTAGTCCACGCCGTAAACGTTGGGAACTAGGTGTTGGCGACATTC<br>CACGTCGTCGGTGCCGCAGCTAACGCATTAAGTTCCCCGCCTGGGGAGTACGGCC<br>GCAAGGCTAAAACTCAAAGGAATTGACGGGGGCCCGCACAAGCAGCGGAGCATG<br>TGGCTTAATTCGACGCAACGCGAAGAACCTTACCAAGGCTTGACATATACCGGAA<br>AGCATCAGAGATGGTGCCCCCCTTGTGGTCGGTATACAGGTGGTGCATGGCTGTC<br>GTCAGCTCGTGTCGTGAGATGTTGGGTTAAGTCCCGCAACGAGCGCAACCCTTGT<br>TCTGTGTTGCCAGCATGCCCTTCGGGGTGATGGGGACTCACAGGAGACTGCCGGG<br>GTCAACTCGGAGGAAGGTGGGGACGACGTCAAGTCATCATGCCCCTTATGTCTTG<br>GGCTGCACACGTGCTACAATGGCCGGTACAATGAGCTGCGATGCCGCGAGGCGG<br>AGCGAATCTCAAAAAGCCGGTCTCAGTTCGGATTGGGGTCTGCAACTCGACCCCA<br>TGAAGTCGGAGTTGCTAGTAATCGCAGATCAGCATTGCTGCGGTGAATACGTTCC<br>CGGGCCTTGTACACACCGCCCGTCACGTCACGAAAGTCGGTAACACCCGAAGCCG<br>GTGGCCCAACCCCTTGTGGGAGGGAG (SEQ ID NO: 6) |

Additional gene sequences for strain 9.4E are depicted in Table 22, below.

TABLE 22 additional gene sequences, strain 9.4E

| Gene | Strain 9.4E Sequence |
|---|---|
| atpD | ATACGGGAGCTTGATGCGAGTGGATCAACCGCCGGGTAAATACCCATTTCGGAAA<br>TTTTACGTTCCAGATTCGTTGTAGCATCCAAATGGGCAAACGTCGTAGCAGGAGCC<br>GGGTCAGTGTAGTCATCCGCAGGCACATAGATCGCCTGAATGGAAGTAACAGAAC<br>CTTTTTTAGTAGAAGTAATCCGTTCTTGCAATTGACCCATCTCAGTAGCCAGCGTA<br>GGCTGGTAACCTACTGCTGAAGGCATACGTCCCAACAGAGCCGAAACCTCAGAAC<br>CCGCTTGAGTAAAGCGGAAATGTTATCAATAAAGAGCAACACGTCACGGCCTTC<br>TTGGTCACGGAAGTATTCCGCCATCGTCAGACCTGTGAGAGCTACACGCAAACGT<br>GCACCTGGAGGCTCGTTCATTTGTCCAAACACCATCGCTGTTTTGTTGATAACGCC<br>GGAATCTCTCATTTCATGATACAAGTCATTTCCTTCACGTGTGCGTTCACCTACACC<br>CGCAAATACAGAAATACCACCATGCTCCTGAGCGATATTGTTAATCAATTCTTGAA<br>TGGTTACGGTTTTACCTACACCAGCACCACCAAACAATCCGACTTTACCACCTTTGG<br>CATAAGGAGCTAGCAAGTCGATAACTTTAATACCTGTTTCGAGCATCTC<br>(SEQ ID NO: 7) |
| recA | CCCTGACCAAGGCGCTCACCTTCGTAGGAATACCAGGCTCCGCTCTTGTCGACAAT<br>GTCATGCTCCGTACCGATATCGATCAAGCTACCTTCTTTGGAAATACCCTCACCGTA<br>CATAATATCCACCTCAGCCTGACGGAAAGGAGGGGCAACTTTGTTCTTCACGACTT<br>TAATACGTGTGCGGTTACCCACAATGTCGTTACCCATTTTCAAACTTTCAATACGAC<br>GAACATCCAAACGTACCGTAGAGTAAAACTTCAAGGCACGTCCACCTGGTGTTGT<br>TTCAGGGTTACCGAACATAACACCTACTTTTTCACGTAGCTGGTTAATAAAAATAG<br>CAATGGTTTTCGACTTGTTAATGGCTCCAGAAAGCTTACGCAATGCCTGGGACATC<br>AAACGTGCTTGAAGACCAACGTGGGAATCTCCCATTTCGCCTTCAATCTCTGCCTT<br>GGGCACAAGTGCCGCTACGGAGTCAACAACTACAATGTCTACTGCTCCACTACGT<br>ACAAGGGCTTCGGCAATCTCAAGCGCCTGCTCTCCTGTATCTGGTTGCGATAGTAA<br>CAACTCATCAATATTGACACCCAGCTTGCTTGCATACGACGGATCAAGCGCATGCT<br>CGGCGTCGATAAAGGCGGCTTGTCCGCCTGTTTTTTGCACCTCTGCGATAGCGTGA<br>AGAGCTACTGTCGTTTTACCGGATGATTCCGGTCCGTATATTTCAATAACCCGGCC<br>(SEQ ID NO: 8) |
| trpB | GTCATTGCTGAAACAGGCGCAGGACAGCATGGTGTCGCGACAGCGACTGTGGCT<br>GCGTTGCTCGGATTGGAATGCAAGGTGTTTATGGGCGAAGAGGATACTGTGCGC<br>CAGCAGCTGAACGTCTTTCGGATGCAGCTTTTGGGTGCAGAGGTCATTCCGGTGA<br>CATCAGGTACACGTACACTTAAGGATGCCGGGAATGAAGCTTTGCGTTACTGGGT<br>CAGCCATGTCCATGATACGTTCTATATTTTGGGTTCAGCTGTCGGCCCGCACCCGT<br>ATCCGATGATGGTGCGGGACTTCCAACGTGTGATTGGTGATGAAACACGTCGCCA<br>GATCCTAGAGAAGGAAGGCAGACTTCCGGATGTCATCGTGGCAGCGATCGGTGG<br>CGGAAGCAATGCCATCGGCATGTTTTATCCTTTTATTGAGGATCAGGGTGTCGCAT<br>TGATTGGCGTGGAGGCCGCTGGAAAAGGTGTCGAAACGGAATTCCATGCAGCTA<br>CGATGACCAAGGGAACACAAGGGGTCTTCCAAGGCTCTATGAGTTATCTGCTTCA<br>GGATGAGTATGGACAAGTGCAACCTGCGCATTCCATCTCGGCTGGATTAGATTAT<br>CCAGGTGTTGGACCGGAGCATTCATACCTGAAAGA (SEQ ID NO: 9) |
| gyrB | AGCTTTGTCTTGGTCTGACCCTCAAACTGTGGTTCTGGAATTTTGACGGAGATAAT<br>CGCCGTCAATCCTTCACGCACATCGTCACCGGTCAAGTTGGCGTTGTTGTCCTTAA<br>TCAAGCCATTTTTACGTGCATAATCGTTAATAATCCGGGTTAATGCACTCTTGAAAC<br>CTGATTCGTGAGTTCCGCCCTCATGGGTGTTGATGTTGTTGGCAAAAGAATAAATA<br>TTCTCGGTATAGCTGTCGTTATATTGCAATGCCACTTCGACTTGAATCATATCACGC<br>GAGCCTTCGACATAAATCGGCTGTTCATGCAGCGCTTCTCTTTTTTGATTCAAAAAT<br>TGCACATATTCACTGATTCCGCCCTCGTAGTGAAATGTATCGCTGGCGCCCGTCCG<br>TTCATCAGTCAAGCTGATTGCAATACCTTTGTTCAGGAAAGCCAACTCACGAATCC<br>GTGTCTGGAGCGTATCATAGTCATATACGGTCGTTTCTGTAAAGATTTGATCGTCA<br>GGATAAAAAGTCGTTTGGGTACCCGTCTCGTCTGTGTCACCGATGACTCTGACATC<br>ATACTGCGGAGCACCACGATGATATTCCTGCTCATACAGATGTCCGTCCCGTTTAA<br>CATGCACGATCATTTTGCTGGAGAGGGCATTTACTACGGATACACCAACCCCGTGC<br>AGACCACCGGATACCTTGTACCCTCCGCCTCCAAATTTACCACCTGCGTGAAGCAC<br>GGTCATAACGACTTCCAGCGCAGATTTTTTCATTTTGGCGTGTTCACTTACTGGAAT<br>ACCGCGACCGTTATCTGTAACGGTAATGCTATTGTCTTCGTGAACGACAACTTGAA<br>TGCTGTCACAGTAACCCGCCAGCGCTTCGTCAATGCTGTTGTCCACAACTTCCCAG<br>ACCAAATGATGGAGACCTTTGGCGCTCGTGGAGCCAATATACATCCCGGGACGTT<br>TCCGAACCGCTTCCAGGCCCTCAAGGACCTGAATCTCGCCCGCATCATAAGACGGT<br>TGATTCATAGACATGCCTTTCACCTACTTCTATAGATTCTATGGTTAAGCATTGGCA<br>ACAAACTGGTTTGCCCGCTTTTTGAGTGTTGTTGAGGAGATGGGGGAATAATACA<br>CCGTATTCTGAGTCACTACGATGGACTTGGCTTCCTCTTCGCCAATCATCTCGACAT<br>GCTTCTGCTGTTGGGCGTGGTTCACGTATTGCTTGGAGATTTTAGAGGATTTTTCA<br>ATCGAGATATCGAAAATAGCCACAAGCTCTGAAGAGCGGATGATTTTTTCTCCACC<br>CAGATGAAT (SEQ ID NO: 10) |

Additional gene sequences for strain 10.6D are depicted in Table 23, below.

TABLE 23 additional gene sequences, strain 10.6D

| Gene | Strain 10.6D sequence |
|---|---|
| recA | GCATTCTCCCGTCCCTGACCAAGGCGCTCACCTTCGTAGGAATACCAGGCTCCGCT CTTGTCGACAATGTCATGCTCCGTACCGATATCGATCAAGCTACCTTCTTTGGAAAT ACCCTCACCGTACATAATATCCACCTCAGCCTGACGGAAAGGAGGGGCAACTTTG TTCTTCACGACTTTAATACGTGTGCGGTTACCCACAATGTCGTTACCCATTTTCAAA CTTTCAATACGACGAACATCCAAACGTACCGTAGAGTAAAACTTCAAGGCACGTCC ACCTGGTGTTGTTTCAGGGTTACCGAACATAACACCTACTTTTTCACGTAGCTGGTT AATAAAAATAGCAATGGTTTTCGACTTATTAATGGCTCCAGAAAGCTTACGCAATG CCTGAGACATCAAACGTGCTTGAAGACCAACGTGGGAATCTCCCATTTCGCCTTCA ATCTCTGCMGGGCACAAGTGCCGCTACGGAGTCAACAACTACAATGTCTACTGC TCCACTACGTACAAGGGCTTCGGCAATCTCAAGCGCCTGCTCTCCTGTATCTGGTT GCGATAGTAACAACTCATCAATATTGACACCCAGCTTGCTTGCATACGACGGATCA AGCGCATGCTCGGCGTCGATAAAGGCGGCTTGTCCGCCTGTTTTTTGCACCTCTGC GATAGCGTGAAGAGCTACTGTCGTTTTACCGGATGATTCCGGTCCGTATATTTCAA TAACCCGGCC (SEQ ID NO: 11) |
| atpD | ATACGGGAGCTTGATGCGAGTGGATCAACCGCCGGGTAAATACCCATTTCGGAAA TTTTACGTTCCAGATTCGTTGTAGCATCCAAATGGGCAAACGTCGTAGCAGGAGCC GGGTCAGTGTAGTCATCCGCAGGCACATAGATCGCCTGAATGGAAGTAACAGAAC CTTTTTTAGTAGAAGTAATCCGTTCTTGCAATTGACCCATCTCAGTAGCCAGCGTA GGCTGGTAACCTACTGCTGAAGGCATACGTCCCAACAGGGCTGAAACCTCAGAAC CCGCTTGAGTAAAGCGGAAAATGTTATCAATAAAGAGCAACACGTCACGGCCTTC TTGGTCACGGAAGTATTCCGCCATCGTCAGACCTGTGAGAGCTACACGCAAACGT GCACCCGGAGGCTCGTTCATTTGTCCGAACACCATCGCTGTTTTGTTGATAACGCC GGAATCTCTCATTTCATGATACAAGTCATTTCCTTCACGTGTGCGTTCACCTACACC CGCAAATACAGAAATACCACCATGCTCCTGAGCGATATTGTTAATCAATTCTTGAA TGGTTACGTTTTACCTACACCAGCACCACCAAACAATCCGACTTTACCACCTTTGG CATAAGGAGCTAGCAAGTCGATAACTTTAATACCTGTTTCGAGCATCTCTGCTTGA GTTGTCAGCTCATCGAAAGAAGGAGCTTGACGGTGAATCGG (SEQ ID NO: 12) |
| trpB | GTCATTGCTGAAACAGGCGCAGGACAGCATGGTGTCGCGACAGCGACTGTGGCT GCGTTGCTCGGATTGGAATGCAAGGTGTTTATGGGCGAAGAGGATACTGTGCGC CAGCAGCTGAACGTCTTTCGGATGCAGCTTTTGGGTGCAGAGGTCATTCCGGTGA CATCAGGTACACGTACACTTAAGGATGCAGGGAATGAAGCTTTGCGTTACTGGGT CAGCCATGTCCATGATACGTTCTATATTTTGGGTTCAGCTGTCGGCCCACATCCGT ATCCGATGATGGTGCGGGACTTCCAACGCGTGATTGGTGATGAAACACGTCGCCA GATCCTAGAGAAGGAAGGCAGACTTCCGGATGTCATCGTGGCAGCGATCGGTGG CGGAAGCAATGCCATCGGAATGTTTTATCCTTTTATTGAGGATCAGGGTGTCGCAT TGATTGGCGTGGAGGCCGCTGGAAAAGGTGTCGAAACGGAATTCCATGCAGCTA CGATGACCAAGGGAACACAAGGGGTCTTCCAAGGCTCTATGAGTTATCTGCTTCA GGATGAGTACGGACAAGTGCAACCTGCGCATTCCATCTCGGCTGGATTAGATTAT CCAGGTGTTGGACCGGAGCATTCATACCTGAAAGA (SEQ ID NO: 13) |
| GyrB | AAGTTGGCGTTGTTGTCCTTAATCAAGCCATTTTTACGTGCATAATCGTTAATAATC CGGGTTAATGCACTCTTGAAACCTGATTCGTGAGTTCCGCCCTCATGGGTGTTGAT GTTGTTGGCAAAAGAATAAATATTCTCGGTATAGCTGTCGTTATATTGCAATGCCA CTTCGACTTGAATCATATCACGCGAGCCTTCGACATAAATCGGCTGTTCATGCAGC GCTTCTCTTTTTTGATTCAAAAATTGCACATATTCACTGATTCCGCCCTCGTAGTGA AATGTATCGCTGGCGCCCGTCCGTTCATCAGTCAAGCTGATTGCAATACCTTTGTT CAGGAAAGCCAACTCACGAATCCGTGTCTGGAGCGTATCATAGTCATATACGGTC GTTTCTGTAAAGATTTGATCGTCAGGATAAAAAGTCGTTTGGGTACCCGTCTCGTC TGTGTCACCGATGACTCTGACATCATACTGCGGAGCACCACGATGATATTCCTGCT CATACAGATGTCCGTCCCGTTTAACATGCACGATCATTTTGCTGGAGAGGGCATTT ACTACGGATACACCAACCCCGTGCAGACCACCGGATACCTTGTACCCTCCGCCTCC AAATTTACCACCTGCGTGAAGCACGGTCATAACGACTTCCAGCGCAGATTTTTCA TTTTGGCGTGTTCACTTACTGGAATACCGCGACCGTTATCTGTAACGGTAATGCTA TTGTCTTCGTGAACGACAACTTGAATGCTGTCACAGTAACCCGCCAGCGCTTCGTC AATGCTGTTGTCCACAACTTCCCAGACCAAATGATGGAGACCTTTGGCGCTCGTGG AGCCAATATACATCCCGGGACGTTTCCGAACCGCTTCCAGGCCCTCAAGGACCTG AATCTCGCCCGCATCATAAGACGGTTGATTCATAGACATGCCTTTCACCTACTTCTA TAGATTCTATGGTTAAGCATTGGCAACAAACTGGTTTGCCCGCTTTTTGAGTGTTG TTGAGGAGATGGGGAATAATACACCGTATTCTGAGTCACTACGATGACTTGGC TTCCTCTTCGCCAATCATCTCGACATGCTTCTGCTGTTGGGCGTGGTTCACGTATTG CTTGGAGATTTTAGAGGATTTTCAATCGAGATATCGAAAATAGCCACAAGCTCTG AAGAGCGGATGATTTTTTCTCCACCCAGATG (SEQ ID NO: 14) |

Phylogenetic trees were generated as described above, using 16S, atpD, gyrB, recA, and trpB genes.

FIG. 1 depicts a phylogenetic tree visualizing the phylogenetic relationship between strain 9.4E, strain 10.6D, and other *Paenibacillus* strains.

Figure 2:
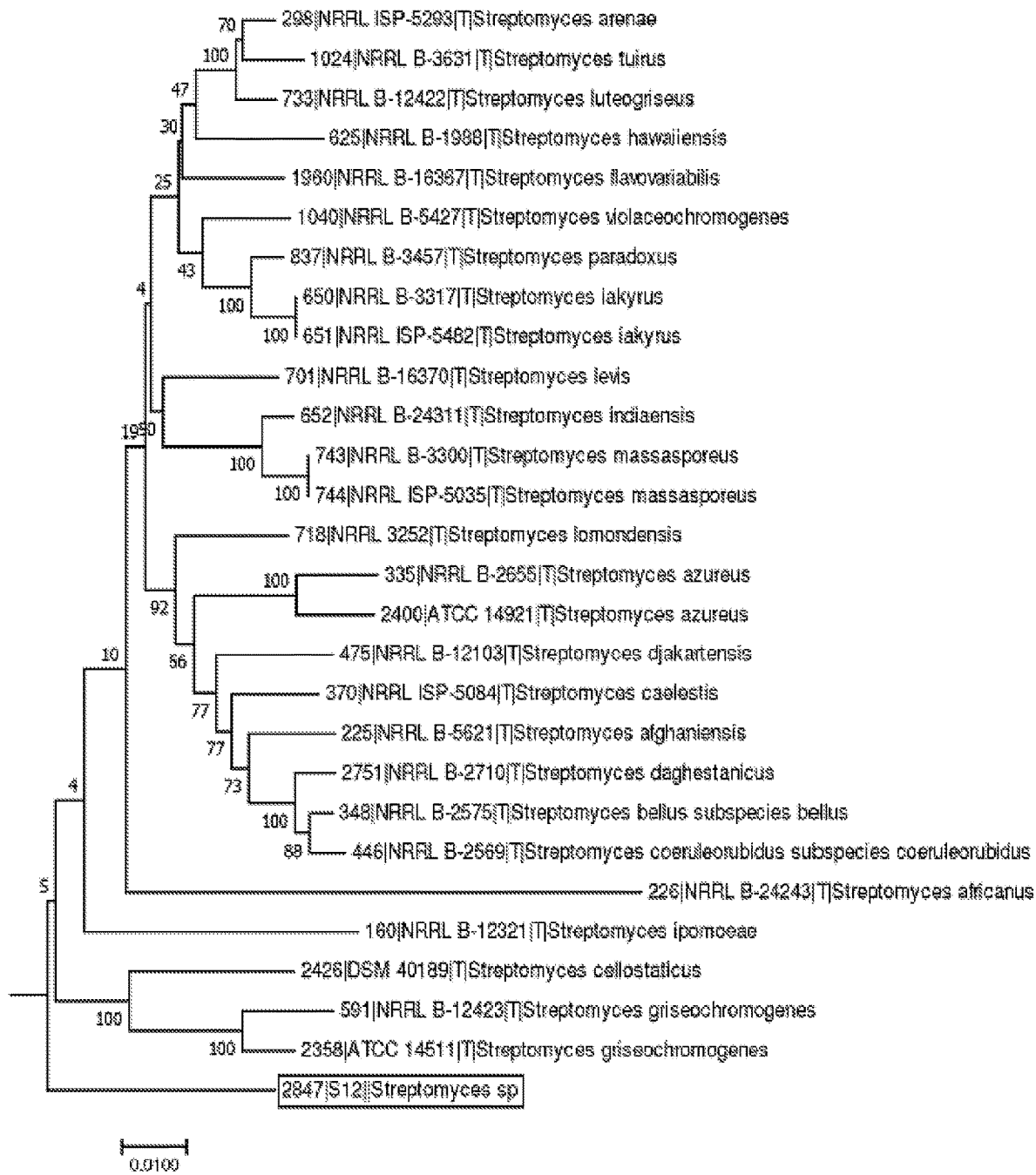
FIG. 2 depicts a phylogenetic tree visualizing the phylogenetic relationship between strain HCA1273 (S12), and other *Streptomyces* strains.

FIG. 2 depicts a phylogenetic tree visualizing the phylogenetic relationship between strain HCA1273, and other *Streptomyces* strains.

Figure 3:
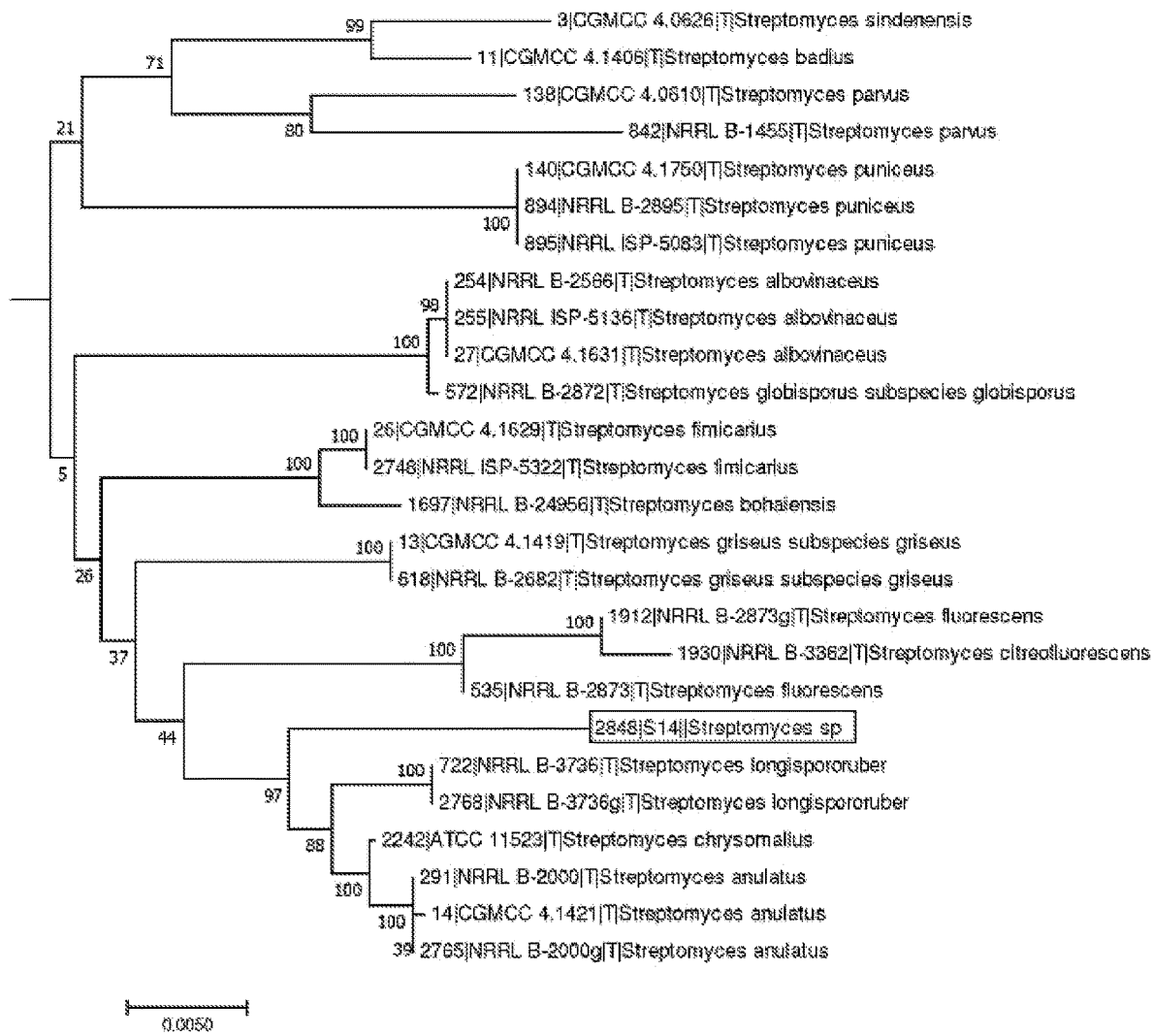
FIG. 3 depicts a phylogenetic tree visualizing the phylogenetic relationship between strain BD141 (S14), and other *Streptomyces* strains.

FIG. 3 depicts a phylogenetic tree visualizing the phylogenetic relationship between strain BD141, and other *Streptomyces* strains.

A comparison of the 16S, atpD, gyrB, recA, and trpB genes between P9 and P10 strains confirm that the isolates are distinct isolates but are closely related. For example, while sequences for 16S and gyrB are completely similar, recA sequences have 2 SNPs between P9 and P10, trpB sequences have 6 SNPs between P9 and P10, and atpD sequences have 4 SNPs between P9 and P10.

EXAMPLE 3

Screening for *Rhizoctonia* Control

All bioassays were conducted in a controlled envi9ronment room at 15° C., 12 hr day/night cycle. Wheat cv. Yitpi was used for all assays. For each assay there were three control treatments, (1) no-pathogen control (2) pathogen only control and (3) positive control of current best biocontrol strain, either *Trichoderma* strain TB or *Streptomyces* strain EN16. Bioassays were conducted in soils collected from fields with continuing *Rhizoctonia* problems. Soils were from Netherton SA (grey siliceous sand) or Waikerie SA (Red calcareous sand).

Primary Tube *Rhizoctonia* Bioassay

This assay consisted of 50 ml tube with 60 g Netherton soil at 8% moisture content with two *Rhizoctonia solani* infested millet seeds added and incubated 2 weeks at 15° C. Two pregerminated wheat seeds were planted and microbial inoculum added as suspension (150 ul) directly onto the seeds and incubated for 2 wks. Plants were assessed by shoot height and number of roots reaching the bottom of the tube. Two replicates were used per treatment. Results are shown in Table 4.

TABLE 4

Primary Rhizoctonia assay results of 10.6D and HCA1273, n = 2.

| Strain | Treatment | Mean shoot height (cm) | Mean number of roots to bottom of tube |
|---|---|---|---|
| 10.6D | Control | 12.75 | 9 |
|  | Disease control | 7.5 | 0 |
|  | 10.6D | 9.5 | 0.5 |
| HCA1273 | Control | 8.75 | 4 |
|  | Disease control | 6.75 | 0 |
|  | HCA1273 | 8.75 | 0.5 |

Secondary *Rhizoctonia* Pot Bioassay

To confirm efficacy, strains were assessed in a pot bioassay containing 300 g Waikerie soil at 8% moisture. Six *Rhizoctonia solani* infested millet seeds were added to the soil and incubated 2 weeks at 15° C. For seed inoculation, microbes were harvested from agar plates, diluted to absorbance of 0.5 at 550 nm in 3 ml dilute sticker solution (0.005% Na Alginate, 0.03% xantham gum) and 1.5 g wheat seed added and soaked for 1 hr. The microbial suspension was drained and 7 seeds planted and later thinned to 5 after germination. Inoculum concentration was determined by dilution plate counts. Plants were grown for 4 wks. Plants were assessed for root disease as Percentage of Roots Infected (% RI) and on a Root Disease Score (RDS) on a 0-5 scale (0=no disease, 5=max disease). The length of seminal and nodal roots were measured and dry weights of roots and shoots obtained after drying at 60° C. for 4 days. There were 4 replicates in a randomised complete block design. Data was analysed as ANOVA, RCBD. Results are shown in Tables 5 and 6.

TABLE 5

Results of secondary assay for strain 10.6D. Inoculum suspension 10.6D, 2.0 × 10⁶ cfu/ml.

| Treatment | Shoot DW mg/pot | Root DW mg/pot | % RI | Total Root Length (cm) | Length seminal roots (cm) | Length nodal roots (cm) | Root Disease Score (0-5) |
|---|---|---|---|---|---|---|---|
| No pathogen control | 381* | 364* | 18* | 59* | 45* | 13.5 | 0.8* |
| Pathogen only control | 316 | 211 | 82 | 35 | 28 | 7.1 | 3.1 |
| TB | 311 | 270 | 73 | 40 | 29 | 11.8 | 2.1* |
| 10.6D | 313 | 301* | 72 | 43 | 30 | 13.1 | 2.4* |
| Fprob | 0.006 | 0.020 | <0.001 | 0.003 | <0.001 | 0.351 | <0.001 |
| LSD(0.05) | 39.8 | 87.6 | 12.6 | 9.9 | 5.6 | ns | 0.70 |

*= significantly different from pathogen only control at P = 0.05

TABLE 6

Results of secondary assay for strain HCA1273. Inoculum suspension $6.0 \times 10^8$ cfu/ml. Treatment

| | Shoot DW mg/pot | Root DW mg/pot | % RI | Total Root Length (cm) | Length seminal roots (cm) | Length nodal roots (cm) | Root Disease Score (0-5) |
|---|---|---|---|---|---|---|---|
| No pathogen control | 165 | 155* | 64* | 41* | 39* | 2.2 | 0.2* |
| Pathogen only control | 169 | 107 | 86 | 24 | 23 | 1.7 | 2.6 |
| EN16 | 166 | 117 | 83 | 28 | 25 | 2.4 | 2.2 |
| HCA 1273 | 161 | 136 | 80 | 30 | 28 | 3.0 | 1.5* |
| Fprob | 0.846 | 0.022 | 0.001 | 0.004 | 0.002 | 0.163 | 0.003 |
| LSD(0.05) | ns | 30.8 | 9.3 | 8.1 | 7.0 | ns | 0.98 |

*= significantly different from pathogen only control at P = 0.05

Tertiary *Rhizoctonia* Pot Bioassay

A tertiary assay was conducted on selected strains based on results of the secondary assay. The tertiary pot bioassay was conducted the same as for the secondary *Rhizoctonia* pot assay except that microbes were inoculated at 3 rates to indicate the most appropriate inoculation level. Seed cfu levels were measured on seeds at the highest inoculation rate by extracting cells from 5 seeds in 1 ml phosphate buffered saline (PBS) after shaking for 30 minutes, serially diluting the suspension and plating onto agar. Seed cfu levels at the lower rates were estimated from the highest rate. Results are shown in Tables 7 and 8.

TABLE 7

Results of tertiary assay for strain 10.6D.

| Treatment | Inoculum (cfu/seed) | Shoot DW mg/pot | Root DW mg/pot | % RI | Total Root Length (cm) | Length seminal roots (cm) | Length nodal roots (cm) | Root Disease Score (0-5) |
|---|---|---|---|---|---|---|---|---|
| No pathogen control | | 330* | 268* | 11* | 61* | 45* | 15.8 | 0.6* |
| Pathogen only control | | 135 | 63 | 100 | 11 | 6 | 4.8 | 4.2 |
| TB | $2.0 \times 10^4$ | 191* | 80 | 100 | 13 | 9 | 3.7 | 4.1 |
| 10.6D | $3.3 \times 10^4$ | 210* | 100 | 93 | 22* | 16* | 6.1 | 3.1* |
| 10.6D | $6.7 \times 10^4$ | 146 | 72 | 93 | 14 | 9 | 5.2 | 4.6 |
| 10.6D | $1.3 \times 10^5$ | 157 | 93 | 90 | 22* | 14* | 8.2 | 3.4* |
| Fprob | | 0.006 | 0.020 | <0.001 | 0.003 | <0.001 | 0.351 | <0.001 |
| LSD(0.05) | | 39.8 | 87.6 | 12.6 | 9.9 | 5.6 | ns | 0.70 |

*= significantly different from pathogen only control at P = 0.05

TABLE 8

Results of tertiary assay for strain HCA1273.

| Treatment | Inoculum (cfu/seed) | Shoot DW mg/pot | Root DW mg/pot | % RI | Total Root Length (cm) | Length seminal roots (cm) | Length nodal roots (cm) | Root Disease Score (0-5) |
|---|---|---|---|---|---|---|---|---|
| No pathogen control | | 258.2 | 155.5 | 69 | 35.1 | 16 | 1.7 | 0.5 |
| Pathogen only control | | 173.5 | 82.5 | 89 | 17.7 | 30.15 | 5 | 3.2 |
| EN16 | $1.5 \times 10^6$ | 205.2 | 108.2 | 85 | 19 | 17.75 | 1.25 | 2.3 |
| HCA1273 | $5.9 \times 10^4$ | 198.2 | 114.2 | 78.5 | 28.8 | 23.9 | 4.9 | 1.85 |
| HCA1273 | $3.0 \times 10^5$ | 192 | 99 | 84 | 23.4 | 21.88 | 1.5 | 2.58 |
| HCA1273 | $3.0 \times 10^6$ | 185 | 106.2 | 82 | 21.3 | 19.75 | 1.55 | 2.35 |
| Fprob | | 0.144 | 0.453 | 0.387 | 0.660 | 0.564 | 0.750 | 0.200 |
| LSD(0.05) | | ns | ns | ns | ns | ns | ns | ns |

*= significantly different from pathogen only control at P = 0.05

*Rhizoctonia* Field Trials: Microplots

All *Rhizoctonia* field trials were carried out in fields used for commercial cereal production in South Australia with a continuing *Rhizoctonia* problem, with natural levels of *Rhizoctonia solani* AG8 DNA>100 pg/g soil (as measured by SARDI Root Disease Testing Service).

Selected strains were first assessed in the field in 1 m long single row microplots in 2012 and 2013. Wheat cv. Grenade seeds were coated with microbes as a concentrated suspension in a sticker solution (0.3% xanthan gum, 0.05% Na alginate). Seeds were hand planted at 4 cm spacing using a seeding template. Microplot trials were a split plot design, with each treated row paired with an untreated row in a randomised complete block design, 6 replicates. *Rhizoctonia* root rot is a patchy disease, so a split-plot design with paired treated and untreated rows was used to measure disease in the same disease space. Plants (10) were harvested at 8 wks and assessed for root disease score (0-5 scale) caused by *Rhizoctonia* on seminal and nodal roots and for dry weights of roots and shoots. Each strain was assessed at 2 sites. In 2013, Chemical seed treatments (Vibrance, Syngenta; Ever-Gol Prime, Bayer) and *Streptomyces* strain EN16 were included for comparison. Results are shown in Tables 9 and 10.

TABLE 9

Combined results for 2012 microplot trials at Karoonda (SA, Mallee) and Port Julia (SA, Yorke Peninsula) at 8 wks, n = 12. Seed inoculation, 10.6D 4.3 × 10$^5$ cfu/seed.

| | | |
|---|---|---|
| Shoot DW (mg/plant) | Treated | 272 |
| | Un-treated | 244 |
| | % change from untreated[1] | 11 |
| Root DW (mg/plant) | Treated | 55 |
| | Un-treated | 52 |
| | % change from untreated | 6 |
| Nodal Root Disease Score (0-5) | Treated | 1.5** |
| | Un-treated | 2 |
| | % change from untreated | −23 |
| Seminal Root Disease Score (0-5) | Treated | 0.9* |
| | Un-treated | 1.2 |
| | % change from untreated | −23 |

*significantly different from un-treated control at P = 0.05
**significantly different from un-treated control at P = 0.01
[1]percent change of treated rows from untreated rows

TABLE 10

Combined results for 2013 microplot trials at Wynarka (SA, Mallee) and Lamaroo (SA, Mallee) at 8 wks, n = 12. Seed inoculation, HCA1273 2.4 × 10$^5$ cfu/seed; EN16 2.4 × 10$^4$ cfu/seed.

| | | HCA1273 | EN16 | EverGol Prime | Vibrance |
|---|---|---|---|---|---|
| Shoot DW (mg/plant) | Treated | 880* | 876 | 829 | 854 |
| | Un-treated | 725 | 793 | 793 | 747 |
| | % change from untreated[1] | 21 | 10 | 5 | 14 |
| Root DW (mg/plant) | Treated | 120* | 123 | 126 | 124* |
| | Un-treated | 101 | 105 | 114 | 105 |
| | % change from untreated | 18 | 17 | 11 | 18 |
| Nodal Root Disease Score (0-5) | Treated | 2.7* | 2.3* | 2.1 | 2.2 |
| | Un-treated | 3.1 | 2.8 | 2.3 | 2.4 |
| | % change from untreated | −23 | −18 | −8 | −6 |
| Nodal Root Disease Score (0-5) | Treated | 1.4* | 1.2* | 1.3 | 1.3 |
| | Un-treated | 1.9 | 1.8 | 1.4 | 1.3 |
| | % change from untreated | −27 | −34 | −8 | 0 |

*significantly different from un-treated control at P= 0.05
[1]percent change of treated rows from untreated rows

*Rhizoctonia* Field Trials: 20 m 3+3 Row Plots

Strains selected from microplot trials and characterisation were assessed as seed coatings in larger field trials in 2013 and 2014 with 20 m plots, six replicates. Three rows of each plot were treated and three rows untreated in a split-plot randomised complete block design to allow comparison in the same disease space due to the patchy nature of *Rhizoctonia* root rot. Wheat cv. Grenade seeds were coated with microbes as a concentrated suspension in a sticker solution (0.3% xanthan gum, 0.05% Na alginate). Seeds were planted with a plot scale seeder and herbicide and fertilisers applied as per local best practice. Plants (21) from each split-plot were assessed at 8 wks (2013) or 11 wks (2014) and assessed for root disease score (0-5 scale) caused by *Rhizoctonia* on seminal and nodal roots and for dry weights of roots and shoots. Seeds were harvested at the end of season with a plot scale header. In 2014, *Streptomyces* strain EN16 and an in-furrow chemical treatment, Uniform (Syngenta) were included as controls. Results are shown in Table 11.

TABLE 11

Results for 2013 and 2014 3 + 3 row 20 m plots field trials at Wynarka (SA, Mallee) and Lameroo (SA, Mallee) in 2013 and at Lameroo (SA, Mallee) in 2014 at 8 wks and yield, n = 6. Percent change (% change) = [(Microbe treated/untreated) × 100] − 100

| | | 2013 Lameroo | 2013 Wynarka | 2014 Lameroo | | | |
|---|---|---|---|---|---|---|---|
| | | 10.6D (9.6 × 10$^4$) | 10.6D (1.1 × 10$^5$) | 10.6D 4.8 × 10$^4$ | HCA1273 4.2 × 10$^4$ | EN16 4.5 × 10$^5$ | Uniform |
| Shoot DW (mg/plant) | Treated | 455 | 242 | 719 | 847 | 765 | 730 |
| | Un-Treated | 431 | 213 | 751 | 746 | 652 | 747 |
| | % change from untreated[1] | 6 | 13 | −4 | 14 | 17 | −2 |
| Root DW (mg/plant) | Treated | 52 | 39 | 94 | 105 | 100 | 104 |
| | Un-Treated | 51 | 35 | 102 | 97 | 92 | 96 |
| | % change from untreated | 2 | 12 | −8 | 8 | 9 | 9 |
| Nodal Root Disease Score (0-5) | Treated | 2.1 | 2.4 | 2.1* | 2.5* | 1.9* | 1.7* |
| | Un-Treated | 1.8 | 2.7 | 2.6 | 3.2 | 2.4 | 2.2 |
| | % change from untreated | 14 | −9 | −20 | −23 | −21 | −21 |

TABLE 11-continued

Results for 2013 and 2014 3 + 3 row 20 m plots field trials at Wynarka (SA, Mallee) and Lameroo (SA, Mallee) in 2013 and at Lameroo (SA, Mallee) in 2014 at 8 wks and yield, n = 6. Percent change (% change) = [(Microbe treated/untreated) × 100] − 100

|  |  | 2013 Lameroo | 2013 Wynarka | 2014 Lameroo | | | |
|---|---|---|---|---|---|---|---|
|  |  | 10.6D ($9.6 \times 10^4$) | 10.6D ($1.1 \times 10^5$) | 10.6D $4.8 \times 10^4$ | HCA1273 $4.2 \times 10^4$ | EN16 $4.5 \times 10^5$ | Uniform |
| Seminal Root Disease Score (0-5) | Treated | 1.0* | 1.2 | 2.1* | 1.9* | 2 | 1.4* |
|  | Un-Treated | 1.4 | 1.3 | 2.5 | 2.8 | 2.4 | 2.2 |
|  | % change from untreated | −27 | −12 | −17 | −32 | −15 | −35 |
| Yield (t/ha) | Treated | 2.86 | 2.23 | 2.68* | 2.6 | 2.63 | 2.56* |
|  | Un-Treated | 2.75 | 2.14 | 2.57 | 2.52 | 2.56 | 2.49 |
|  | % change from untreated | 4.1 | 3.8 | 4.2 | 2.8 | 2.5 | 3 |

*significantly different from un-treated control at P = 0.05
[1]percent change of treated rows from untreated rows

EXAMPLE 4

Screening for *Pythium* Control on Wheat

Primary *Pythium* Tube Bioassay

The primary *Pythium* tube assay was set up as for the *Rhizoctonia* tube assay with 60 g washed sand at 11% moisture with 3 g/L Miracle Gro soluble fertiliser. *Pythium irregulare* strain 89 was added as one 11 mm agar plug, with no pre-incubation prior to seeding with two pre-germinated wheat cv. Yitpi seeds. For seed inoculation, microbes were harvested from agar plates, diluted to absorbance of 0.8 at 550 nm in a dilute sticker solution (0.005% Na alginate, 0.03% xanthan gum) and 150 ul added directly to seeds. Plants were assessed by shoot height and number of roots reaching the bottom of the tube. Two replicates per treatment. Results are shown in Table 12.

TABLE 12

Primary Pythium assay results of 9.4E, and BD141, n = 2

| Assay-strain | Treatment | Mean shoot height (cm) | Mean number of roots to bottom of tube |
|---|---|---|---|
| 9.4E | Control | 20.5 | 6 |
|  | Disease control | 13.5 | 1 |
|  | 9.4E | 17.5 | 3 |
| BD141 | Control | 8.0 | 6 |
|  | Disease control | 5.3 | 0.5 |
|  | BD141 | 7.75 | 2 |

Secondary *Pythium* Pot Bioassay

Washed sand (200 g/pot) at 11% moisture with 1.5 g/L Miracle Grow fertiliser was used. Pathogen was added as 3x8 mm agar plugs of *Pythium irregulare* strain 89. Wheat cv. Yitpi seeds (2.2) were inoculated with a microbial suspension diluted to absorbance of 0.8 at 550 nm in 3 ml dilute sticker solution (0.005% Na Alginate, 0.03% xanthan gum) and soaked for 1 hr prior to planting. Microbial suspension was drained and 7 seeds sown and thinned to 5 after 14 days. Plants were grown for 4 weeks and assessed for root disease on a 0-5 scale and for dry weight of shoots and roots. Results are shown in Tables 13 and 14.

TABLE 13

Results of secondary assay for strain 9.4E.

| Treatment | Inoculum (cfu/seed) | No. plants emerged (7 d) | Shoot DW mg/plant | Root DW mg/plant | Root Disease Score (0-5) |
|---|---|---|---|---|---|
| No pathogen control |  | 5.8* | 35* | 26* | 0.4* |
| Pathogen only control |  | 3.8 | 27 | 21 | 2.7 |
| EN27 | $3.5 \times 10^5$ | 3.5 | 25 | 19 | 2.0 |
| 9.4E | $1.7 \times 10^5$ | 3.3 | 24 | 10 | 1.4* |
| Fprob |  | 0.004 | 0.002 | 0.003 | <0.001 |
| LSD (0.05) |  | 2.01 | 4.9 | 3.9 | 0.95 |

*significantly different from pathogen only control at P = 0.05

TABLE 14

Results of secondary assay for strain BD141.

| Treatment | Inoculum (cfu/seed) | No. plants emerged (6 d) | Shoot DW mg/plant | Root DW mg/plant | Root Disease Score (0-5) |
|---|---|---|---|---|---|
| No pathogen control |  | 6.8* | 35 | 26 | 0.2* |
| Pathogen only control |  | 2.3 | 32 | 17 | 2.3 |
| EN27 | $3.5 \times 10^6$ | 3.5 | 29 | 19 | 1.8 |
| BD141 | $5.3 \times 10^5$ | 4.0* | 35 | 22 | 1.3* |
| Fprob |  | 0.020 | 0.581 | 0.795 | 0.006 |
| LSD(0.05) |  | 1.43 | ns | 12.6 | 0.74 |

*significantly different from pathogen only control at P = 0.05

Tertiary *Pythium* Tub Bioassay

An emergence assay in 100 ml tubs with 140 g Waikerie sand at 13% moisture was used to assess pre and post emergence damping off control. Twenty wheat cv. Yitpi seeds were planted, and covered with 1 g *Pythium irregulare* strain 89 sand-polenta inoculum. Plants were grown for 14 d at 15° C., 12 hr day/night cycle, 4 replicates in randomised complete block design. EN27 was included as a positive control. The number of plants emerged was counted at 7, 11, and 14 days after planting. A chemical control (Dividend, difanconazole and metalaxyl) for *Pythium* was included in the assay with 9.4E assay. Results are shown in Tables 15 and 16.

TABLE 15

Results of secondary assay for strain 9.4E.

| Treatment | Inoculum (cfu/seed) | No. plants Emerged (7 d) | No. plants Emerged (11 d) |
|---|---|---|---|
| No pathogen control | | 12.8* | 18.8* |
| Pathogen only control | | 2.5 | 7.3 |
| Dividend | | 8.0* | 14.5* |
| EN27 | $2.3 \times 10^6$ | 4.8 | 10.5* |
| 9.4E | $8.9 \times 10^4$ | 4.5 | 8.0 |
| 9.4E | $1.8 \times 10^5$ | 4.0 | 7.0 |
| 9.4E | $3.5 \times 10^5$ | 7.5* | 12.3* |
| Fprob | | <0.001 | <0.001 |
| LED(0.05) | | 3.1 | 3.1 |

*significantly different from pathogen only control at P = 0.05

TABLE 16

Results of secondary assay for strain BD141.

| Treatment | Inoculum (cfu/seed) | No. plants Emerged (7 d) | No. plants Emerged (11 d) | No. plants Emerged (14 d) |
|---|---|---|---|---|
| No pathogen control | | 6.5 | 18.3* | 18.3* |
| Pathogen only control | | 0.5 | 8.5 | 10.0 |
| EN27 | $7.1 \times 10^5$ | 3.0 | 13.3* | 14.5* |
| BD141 | $1.9 \times 10^5$ | 3.0 | 12.8* | 13.5* |
| BD141 | $3.8 \times 10^5$ | 2.3 | 11.8* | 12.3 |
| BD141 | $7.7 \times 10^5$ | 2.5 | 13.0* | 14.5* |
| Fprob | | 0.096 | <0.001 | <0.001 |
| LSD(0.05) | | ns | 3.2 | 3.0 |

*significantly different from pathogen only control at P = 0.05

*Pythium* Field Trials

All *Pythium* field trials were carried out in fields used for commercial cereal production in South Australia with a continuing *Pythium* problem, with natural levels of *Pythium* group F DNA>100 pg/g soil (as measured by SARDI Root Disease Testing Service).

Seed coated microbes were assessed at two *Pythium* infested sited in 2015 and 2016 (Table 17). Plant establishment was increased in both years with microbial inoculation compared to controls, but this was only significantly different at the Conmurra sites. Significant yield responses of 4.6 to 6.3% increase were evident in 2015 at Turretfield with non-significant increases at Conmurra. Yield responses in 2016 were probably masked by nearly double the rainfall compared to 2015. Significant reductions in root disease were evident at Turretfield in 2015 and Conmurra in 2016.

TABLE 17

Results from control of Pythium root rot on wheat field trials. Data is the mean plants/m at 3-4 wks, shoot dry weight (DW) mg per plant and seminal root disease score (DS, 0-5) at eight weeks and final grain yield, six replicates. Control treatment contains no fungicide or microbial inoculation. Microbes were applied as seed coatings. % increase in yield is relative to untreated Control.

| Site Year Treatment | Establishment plants/m | Shoot DW mg/plant | Seminal root DS (0-5) | Yield t/ha | % increase in yield |
|---|---|---|---|---|---|
| Turretfield 2015 | | | | | |
| Control | 36 | 892 | 3.1 | 2.51 | 0 |
| Apron | 38 | 872 | 2.7 | 2.49 | −1.00 |
| *Paenibacillus* 9.4E | 37 | 960 | 2.4* | 2.63* | 4.63 |
| *Streptomyces* BD141 | 39 | 870 | 2.8 | 2.67* | 6.27 |
| *Streptomyces* EN27 | 37 | 953 | 2.6* | 2.51 | 0.06 |
| Conmurra 2015 | | | | | |
| Control | 24 | 655 | 2.6 | 4.13 | 0 |
| Apron | 27 | 628 | 2.6 | 4.24 | 2.48 |
| *Paenibacillus* 9.4E | 30* | 603 | 2.6 | 4.31 | 4.39 |
| *Streptomyces* BD141 | 29* | 579 | 2.6 | 4.01 | −2.95 |
| *Streptomyces* EN27 | 28* | 638 | 2.7 | 3.97 | −3.89 |
| Turretfield 2016 | | | | | |
| Control | 37 | 2161 | 2.9 | 4.93 | |
| Apron | 40 | 2476 | 2.8 | 5.08 | 3.0 |
| *Paenibacillus* 9.4E | 39 | 2081 | 2.7 | 4.94 | 0.1 |
| *Streptomyces* BD141 | 37 | 2359 | 2.6 | 5.17 | 4.9 |
| *Paenibacillus* 10.6D | 39 | 2181 | 2.9 | 4.86 | −1.4 |
| *Streptomyces* HCA1273 | 39 | 2200 | 2.6 | 4.75 | −3.7 |
| *Streptomyces* EN27 | 40 | 2220 | 2.7 | 4.77 | −3.3 |

TABLE 17-continued

Results from control of Pythium root rot on wheat field trials.
Data is the mean plants/m at 3-4 wks, shoot dry weight (DW) mg
per plant and seminal root disease score (DS, 0-5) at eight weeks and
final grain yield, six replicates. Control treatment contains no fungicide
or microbial inoculation. Microbes were applied as seed coatings.
% increase in yield is relative to untreated Control.

| Site Year Treatment | Establishment plants/m | Shoot DW mg/plant | Seminal root DS (0-5) | Yield t/ha | % increase in yield |
|---|---|---|---|---|---|
| Conmurra 2016 | | | | | |
| Control | 22 | 688 | 1.8 | 4.16 | 0 |
| Apron | 29* | 582 | 1.5 | 4.17 | 0.4 |
| *Paenibacillus* 9.4E | 32* | 641 | 1.3* | 4.07 | −2.1 |
| *Streptomyces* BD141 | 30* | 616 | 1.5* | 4.12 | -0.9 |
| *Paenibacillus* 10.6D | 30* | 641 | 1.4* | 4.04 | −2.8 |
| *Streptomyces* HCA1273 | 31* | 647 | 1.3* | 4.20 | 1.1 |
| *Streptomyces* EN27 | 22* | 688 | 1.8 | 4.16 | 0 |

*Treatment significantly different from untreated control at P = 0.05 by Fisher's LSD

EXAMPLE 5

Microbial Inoculum Survival on Wheat Seeds

Microbial survival on seeds was assessed on 20 g seed lots (wheat cv. Yitpi) after inoculation and at 1, 2 and 7 days. Concentrated microbial suspensions were made in a sticker solution (0.3% xanthan gum, 0.05% Na alginate) at various concentrations depending on results of tertiary assays and 626 ul added to each 20 g seed lot and mixed until even coverage of seeds. To assess seed colony forming units (cfu), 5 seeds were placed in 1.5 ml tubes, 1 ml phosphate buffered saline added, vortexed 15 sec and shaken for 15 min on orbital shaker at maximum speed. The suspension was sampled, serially diluted, plated onto agar media and cfu/seed calculated. There were two replicates for strains 10.6D and HCA1273, three replicates for 9.4E and BD141 at each time point. Percent survival was calculated based on initial population at t=0. Results are shown in Table 18.

TABLE 18

Log10 cfu/seed and percent survival on seeds at t = 0, 1, 2, and 7 days after
inoculation. Values mean of two (10.6D, HCA1273) or three (9.4E, BD141) replicates.

| Strain | t = 0 Log10 (cfu/seed) | t = 1d Log10 (cfu/seed) | t = 2d Log10 (cfu/seed) | t = 7d Log10 (cfu/seed) | % survival t = 1d | % survival t = 2d | % survival t = 7d |
|---|---|---|---|---|---|---|---|
| 10.6D | 4.50 | 4.56 | 4.30 | 4.32 | 116 | 63 | 65 |
| HCA1273 | 3.54 | 3.64 | 3.42 | 3.71 | 124 | 75 | 148 |
| 9.4E | 5.46 | 5.66 | 5.61 | 5.70 | 161 | 142 | 173 |
| BD141 | 5.75 | 5.80 | 5.90 | 5.91 | 112 | 141 | 145 |

EXAMPLE 6

In Vitro Inhibition of Fungal Pathogens

Strains identified for *Rhizoctonia* control were assessed for in vitro inhibition of four fungal pathogens, R. solani AG8 strain W19, *Pythium irregulare* strain 89 isolated from lucerne roots, *Gaeumannomyces graminis* var. *tritici* (Ggt) strain C3 isolated from wheat roots and *Fusarium pseudograminearum* strain B4a isolated from wheat crowns. Fungi were grown on PDA/4 for between 2 and 7 d depending on strain prior to use. Test fungal pathogens were added to the centre of 9 cm agar plates as 8 mm agar and test strains added as 2×20 μl spots ($10^7$ cfu/ml) on opposite sides of the plate 30 mm from the centre. Inhibition zones were recorded at 2 d for *P. irregulare*, 4 d for *R. solani* and 7 d for Ggt and *F. pseudograminearum*. There were three replicate plates for each pathogen-test strain combination in a randomised complete block design. Results are shown in Table 19.

TABLE 19

In vitro inhibition of root pathogens *Rhizoctonia solani* AG8, *Fusarium pseudograminearum*, *Pythium irregulare* and *Gaeumannomyces graminis tritici* (Ggt) by strains isolated for *Rhizoctonia* control. Response of fungal pathogen to test strains are given as: —— no sign of inhibition; + hyphal avoidance but no clear zone of inhibition; ++ inhibition zone 1-2 mm; +++ inhibition zone > 3 mm.

| Strain | Rhizoctonia solani | Fusarium pseudo-graminearum | Pythium irregulare | Ggt |
|---|---|---|---|---|
| 10.6D | +++ | +++ | +++ | ++ |
| 9.4E | +++ | +++ | +++ | ++ |
| 8D141 | + | — | — | ++ |
| HCA1273 | +++ | +++ | — | +++ |

EXAMPLE 7

Seed Dressing Compatibility

Compatibility of strains with a subset of common seed dressings was assessed by adding the seed dressings at 8 times the recommended application rate per seed to a 5 mm antibiotic disk and applying the disk to a lawn of bacteria ($10^5$ cfu/plate) on an agar plate. Zones of inhibition were measured after 3 days. Results are shown in Table 20. Where a zone of inhibition of greater than 4 mm was observed, this was indicative of an inhibitory effect on the growth of the inoculant.

TABLE 20

Inhibition of strains identified for *Rhizoctonia* control by common seed dressings. Data shows size of inhibition zones in mm surrounding the seed dressing soaked disk in the bacterial lawn, n = 3.

| Seed dressing (manufacturer) | 10.6D | HCA 1273 | EN16 | EN27 |
|---|---|---|---|---|
| Vitaflo C (Chemtura) | 0 | 0 | 0 | 0 |
| Rancona dimension (Chemtura) | 2-8 | 2 | 7 | 12 |
| Proleaf T (Chemtura) | 0 | 0 | 0 | 0 |
| Rancona C (Chemtura) | 0-4 | 2 | 7 | 10 |
| Raxil T (Bayer) | 0-5 | 1 | 8 | >10 |
| Lamardor FS400 (Bayer) | 1-4 | 4 | 6 | 12 |
| Jockey Stayer (Bayer) | 0-5 | 0 | 5 | 10 |
| Vibrance (Syngenta) | 0 | 0 | 3 | 4 |
| Dividend M (Syngenta) | 0 | 1 | 5 | 5 |

EXAMPLE 8

Enhanced Canola Germination and Growth Under Water Limited Conditions

Seed coated microbes were assessed in field trials in a low rainfall zones in Parilla (Murray Mallee) in Australia. *Paenibacillus* 9.4E and *Streptomyces* BD141 had increased establishment growth (plants per meter), and significantly increased the number of secondary roots per plant (Table 21).

TABLE 21

Results from field trials assessing microbial inoculants for increasing establishment, growth and yield of canola in the low rainfall zone. Data is the mean plants/m at 6 wks (Parilla), shoot dry weight (DW) g per plant and number of secondary roots at 13 wks and final grain yield, six replicates. Control treatment contains no fungicide or microbial inoculation. Microbes were applied as seed coatings.

| Site Year Treatment | Establishment Plants/m | Shoot DW g/plant | Secondary roots per plant |
|---|---|---|---|
| Control | 8 | 4.12 | 10.8 |
| *Paenibacillus* 9.4E | 10* | 3.80 | 11.9 |
| *Streptomyces* BD141 | 11* | 5.06 | 14.6* |

*Treatment significantly different from untreated control at P = 0.05 by Fisher's LSD

EXAMPLE 9

Canola Growth Under *Pythium* Root Rot Stress

Strains were assessed as seed coatings on canola at three sites with *Pythium* infested soil. There was no impact on grain yield at the two Spalding sites in 2015 or 2016, however *Streptomyces* BD141 and *Paenibacillus* 9.4E significantly increased the percentage of roots with root hairs at the 2016 Spalding site (Table 22). *Paenibacillus* 9.4E significantly increased grain yield at Turretfield in 2016 by 11.4%.

TABLE 22

Results from control of Pythium root rot on canola field trials. Data presented is the mean plants/m at 3-4 wks, shoot dry weight (DW) mg per plant, root disease score (DS, 0-10), % of root system with root hairs at eight weeks and final grain yield, six replicates. Control treatment contains no fungicide or microbial inoculation. Microbes were applied as seed coatings. % increase in yield is relative to untreated Control.

| Site Year Treatment | Establishment plants/m | Shoot DW mg/plant | Root DS (0-10) | % Root hairs | Yield t/ha | % increase in yield |
|---|---|---|---|---|---|---|
| Spalding 2015 | | | | | | |
| Control | 14 | 1184 | 2.2 | 64 | 2.00 | 0.0 |
| Apron | 15 | 1310 | 2.1 | 66 | 1.94 | −2.8 |
| Paenibacillus 9.4E | 15 | 1344 | 2.3 | 64 | 1.96 | −1.8 |
| Streptomyces BD141 | 15 | 1177 | 2.1 | 66 | 2.01 | 0.5 |
| StreptomycesEN27 | 15 | 1158 | 2.1 | 68 | 1.97 | −1.5 |
| Spalding 2016 | | | | | | |
| Control | 14 | 878 | 0.4 | 80 | 2.91 | 0 |
| Apron | 15 | 899 | 0.3 | 82 | 2.90 | −0.5 |
| Paenibacillus 9.4E | 15 | 890 | 0.2 | 86* | 2.83 | −3.0 |
| Streptomyces BD141 | 13 | 905 | 0.3 | 86* | 2.86 | −1.9 |
| Streptomyces EN27 | 15 | 1061 | 0.2 | 87 | 2.85 | −2.2 |
| Turretfield 2016 | | | | | | |
| Control | 15 | 1210 | <0.1 | 41 | 2.37 | 0.0 |
| Apron | 16 | 1368 | <0.1 | 45 | 2.47 | 4.2 |
| Paenibacillus 9.4E | 17 | 1162 | <0.1 | 44 | 2.65* | 11.4 |
| Streptomyces BD141 | 18 | 1236 | <0.1 | 40 | 2.48 | 4.4 |
| Streptomyces EN27 | 18* | 1275 | <0.1 | 38 | 2.68* | 12.8 |

*Treatment significantly different from untreated control at P = 0.05 by Fisher's LSD Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a microorganism" includes a single microorganism as well as two or more microorganisms; "a wheat plant" includes a single wheat plant as well as two or more wheat plants; and so forth.

Reference to any prior art in this specification is not, and should not be taken as, an acknowledgment or any form of suggestion that this prior art forms part of the common general knowledge in any country.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference is made to standard textbooks of molecular biology that contain methods for carrying out basic techniques encompassed by the present invention, including DNA restriction and ligation for the generation of the various genetic constructs described herein. See, for example, Maniatis et al, Molecular Cloning: A Laboratory Manual (Cold Spring Harbor Laboratory Press, New York, 1982) and Sambrook et al. (2000, supra).

Additional Sheet for Biological Material

Identification of Deposits:

1) The Name and Address of depositary institution for the deposits are:

National Measurement Institute

1/153 Bertie Street

Port Melbourne

Victoria, Australia, 3207

| Date of deposits | Accession Numbers | Identification Reference |
|---|---|---|
| 9 Mar. 2017 | V17/004921 | Paenibacillus sp. 9.4e |
| 9 Mar. 2017 | V17/004922 | Paenibacillus sp. 10.6D |
| 9 Mar. 2017 | V17/004923 | Streptomyces sp. BD141 |
| 9 Mar. 2017 | V17/004924 | Streptomyces sp. HCA1273 |

2) Depositor:

All above mentioned depositions were made by:

Professor Chris Franco

Flinders University

Room 4.19

Level 4 Health Sciences Building

Registry Road, Bedford Park, SA

Australia

SEQUENCE LISTING

The patent contains a lengthy sequence listing. A copy of the sequence listing is available in electronic form from the USPTO web site (https://seqdata.uspto.gov/?pageRequest=docDetail&DocID=US11882838B2). An electronic copy of the sequence listing will also be available from the USPTO upon request and payment of the fee set forth in 37 CFR 1.19(b)(3).

What is claimed is:

1. A composition comprising a wheat seed and a bacterial inoculant for controlling a fungal root disease on a wheat plant, wherein the bacterial inoculant includes a Paenibacillus microorganism at a concentration of at least $3.3 \times 10^4$ CFU/seed, the Paenibacillus microorganism having a 16S rRNA gene nucleotide sequence comprising a sequence that is 100% identical to SEQ ID NO: 3 or SEQ ID NO: 4, and wherein the bacterial inoculant enhances a growth parameter of the wheat plant of mean establishment plants per meter relative to an untreated control, and wherein the bacterial inoculant comprises at least one element selected from the group consisting of one or more gums, one or more clay or peat based carriers, one or more nutrients including carbon or nitrogen sources, one or more antifungal or antibacterial agents, one or more seed coating agents, and one or more wetting agents.

2. The composition according to claim 1, wherein the fungal root disease is caused by a pathogen of the genus Rhizoctonia or by a pathogen of the genus Pythium.

3. The composition according to claim 1, wherein the bacterial inoculant includes the microorganism of the *Paenibacillus* sp. 10.6D as deposited under NMI accession number V17/004922 or the microorganism of the *Paenibacillus* sp. 9.4E as deposited under NMI accession number V17/004921.

4. The composition according to claim 1, further comprising a seed dressing.

5. A method for controlling a fungal root disease on a wheat plant, the method comprising inoculating a wheat plant with the composition according to claim 1.

6. The method according to claim 5 wherein the fungal root disease is caused by a pathogen of the genus Rhizoctonia.

7. The method according to claim 5 wherein the fungal root disease is caused by a pathogen of the genus Pythium.

8. The method according to claim 5 wherein the bacterial inoculant or inoculant composition are inoculated onto a wheat or canola seed.

9. A composition comprising a canola seed and a bacterial inoculant for improving growth of a canola plant under water limited conditions, wherein the bacterial inoculant includes a microorganism of the genus Paenibacillus at a concentration of at least $3.3 \times 10^4$ CFU/seed, the microorganism having a 16S rRNA gene nucleotide sequence comprising a sequence that is 100% identical to SEQ ID NO: 4 wherein the bacterial inoculant enhances a growth parameter of a mean establishment plants per meter relative to an untreated control, and wherein the bacterial inoculant comprises at least one element selected from the group consisting of one or more gums, one or more clay or peat based carriers, one or more nutrients including carbon or nitrogen sources, one or more antifungal or antibacterial agents, one or more seed coating agents, and one or more wetting agents.

10. The composition according to claim 9, wherein the bacterial inoculant includes the microorganism of the *Paenibacillus* sp. 9.4E as deposited under NMI accession number V17/004921.

11. A method for improving growth of a canola plant under water limited conditions, the method comprising inoculating a canola seed with a bacterial inoculant or inoculant composition comprising a microorganism of the genus Paenibacillus at a concentration of at least $3.3 \times 10^4$ CFU/seed, the microorganism having a 16S rRNA gene nucleotide sequence comprising a sequence that is 100% identical to SEQ ID NO: 4; wherein the improved growth comprises an improved mean establishment plants per meter relative to an untreated control.

12. The method according to claim 11, wherein the bacterial inoculant or inoculant composition comprises the microorganism of the Paenibacillus sp. 9.4E as deposited under NMI accession number V17/004921.

13. The composition of claim 1, wherein the Paenibacillus microorganism comprises a sequence that is 100% identical to SEQ ID NO: 3 and further comprises one or more sequences having at least 97% identity to one or more sequences selected from SEQ ID NOs: 11, 12, 13, and 14.

14. The composition of claim 1, wherein the Paenibacillus microorganism comprises a sequence that is 100% identical to SEQ ID NO: 4 and further comprises one or more sequences having at least 97% identity to one or more sequences selected from SEQ ID NOs: 7, 8, 9, and 10.

15. The composition of claim 9, wherein the microorganism of the genus Paenibacillus further comprises one or more sequences having at least 97% identity to one or more sequences selected from SEQ ID NOs: 7, 8, 9, and 10.

16. The method of claim 11, wherein the microorganism of the genus Paenibacillus further comprises one or more sequences having at least 97% identity to one or more sequences selected from SEQ ID NOs: 7, 8, 9, and 10.

* * * * *